(12) United States Patent
Noyes et al.

(10) Patent No.: US 12,336,694 B2
(45) Date of Patent: Jun. 24, 2025

(54) ORTHOPEDIC ARTHROSCOPIC OPTICAL CANNULA SYSTEM

(71) Applicant: ResnENT, LLC, Bloomington, IL (US)

(72) Inventors: Willard S. Noyes, Bloomington, IL (US); Benjamin J. Gray, Portland, ME (US); Philip J. Simpson, Solana Beach, CA (US)

(73) Assignee: ResnENT, LLC, Bloomington, IL (US)

( * ) Notice: Subject to any disclaimer, the term of this patent is extended or adjusted under 35 U.S.C. 154(b) by 0 days.

(21) Appl. No.: 18/907,272

(22) Filed: Oct. 4, 2024

(65) Prior Publication Data
US 2025/0113992 A1    Apr. 10, 2025

Related U.S. Application Data

(60) Provisional application No. 63/588,130, filed on Oct. 5, 2023.

(51) Int. Cl.
*A61B 1/00* (2006.01)
*A61B 1/05* (2006.01)
*A61B 1/317* (2006.01)

(52) U.S. Cl.
CPC .......... *A61B 1/317* (2013.01); *A61B 1/00068* (2013.01); *A61B 1/05* (2013.01)

(58) Field of Classification Search
CPC ....... A61B 1/317; A61B 1/00068; A61B 1/05; A61B 1/015; A61B 1/051; A61B 1/00137; A61B 5/0235

(Continued)

(56) References Cited

U.S. PATENT DOCUMENTS

| | | | |
|---|---|---|---|
| 5,303,735 A | * | 4/1994 | Cerola .................... F16K 11/22 251/285 |
| 6,068,641 A | | 5/2000 | Varsseveld |

(Continued)

FOREIGN PATENT DOCUMENTS

| | | |
|---|---|---|
| EP | 3 076 852 | 4/2019 |
| EP | 3530298 | 8/2024 |

(Continued)

OTHER PUBLICATIONS

International Search Report and Written Opinion issued in PCT Application No. PCT/US2022/023055, mailed Jul. 4, 2022, in 24 pages.

(Continued)

*Primary Examiner* — Timothy J Neal
*Assistant Examiner* — James Edward Boice
(74) *Attorney, Agent, or Firm* — Knobbe, Martens, Olson & Bear, LLP

(57) ABSTRACT

An optical cannula system can include a cannula, a body, a first tube, a second tube, and a valve assembly. An outer cannula wall can define an interior space extending along an axis of the cannula. One or more inner cannula walls within the outer cannula wall can divide the interior space into a first channel and a second channel. A proximal portion of the cannula can be received within the body. The first and second tubes can extend from the body. The valve assembly can have a first configuration in which the first tube is in fluid communication with the first channel and the second tube is in fluid communication with the second channel. The valve assembly can have a second configuration in which the first tube is in fluid communication with the second channel and the second tube is in fluid communication with the first channel.

30 Claims, 39 Drawing Sheets

(58) Field of Classification Search
USPC .................................................. 600/109, 159
See application file for complete search history.

(56) References Cited

U.S. PATENT DOCUMENTS

| | | | |
|---|---|---|---|
| 6,394,998 | B1 | 5/2002 | Wallace |
| 6,638,289 | B1 | 10/2003 | Johnson et al. |
| 8,870,748 | B2 | 10/2014 | Kucklick |
| 10,271,869 | B2 | 4/2019 | McGuckin, Jr. |
| 11,707,190 | B1 | 7/2023 | Truckai |
| 2007/0010823 | A1 | 1/2007 | Kucklick |
| 2008/0294192 | A1 | 11/2008 | Stefan |
| 2011/0015487 | A1* | 1/2011 | Matasov ............ A61B 1/00128 |
| | | | 600/153 |
| 2011/0270293 | A1 | 11/2011 | Malla et al. |
| 2013/0085498 | A1 | 4/2013 | Matusaitais et al. |
| 2013/0310647 | A1 | 11/2013 | Milton et al. |
| 2014/0005555 | A1 | 1/2014 | Tesar |
| 2015/0196314 | A1 | 7/2015 | Brannon |
| 2015/0216393 | A1 | 8/2015 | Toyoda |
| 2017/0238903 | A1* | 8/2017 | Wood ............... A61B 17/3478 |
| 2017/0265879 | A1 | 9/2017 | Washburn, II et al. |
| 2018/0000321 | A1* | 1/2018 | Wales ............... A61B 17/1285 |
| 2018/0214171 | A1 | 8/2018 | Ryan, Jr. |
| 2019/0328217 | A1 | 10/2019 | Moreau et al. |
| 2020/0359879 | A1 | 11/2020 | Cahill et al. |
| 2020/0359996 | A1 | 11/2020 | Walsh et al. |
| 2021/0100542 | A1 | 4/2021 | Magno |
| 2022/0110516 | A1* | 4/2022 | Mazhar ................ A61M 1/774 |
| 2022/0322927 | A1 | 10/2022 | Noyes et al. |
| 2023/0404617 | A1 | 12/2023 | Noyes et al. |
| 2024/0008719 | A1* | 1/2024 | Wales ................ A61B 1/00128 |
| 2024/0099738 | A1 | 3/2024 | Browne et al. |

FOREIGN PATENT DOCUMENTS

| | | |
|---|---|---|
| WO | WO 2022/212846 | 10/2002 |
| WO | WO 2005/023084 | 3/2005 |
| WO | WO 2006/026236 | 3/2006 |
| WO | WO 2014/065901 | 5/2014 |
| WO | WO 2019/040888 | 2/2019 |

OTHER PUBLICATIONS

International Search Report and Written Opinion for Application No. PCT/US2024/049985, mailed Dec. 23, 2024, in 12 pages.

* cited by examiner

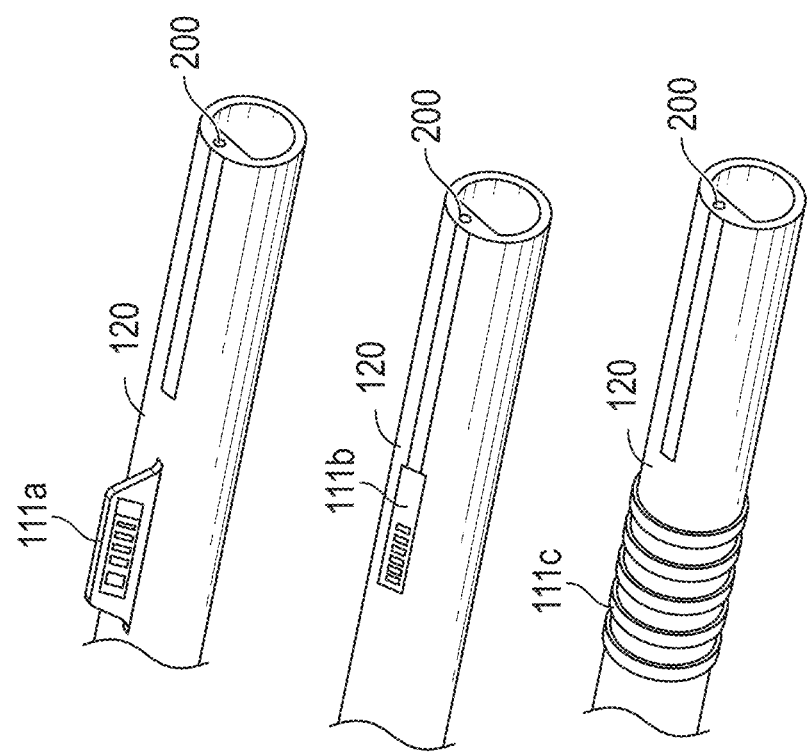
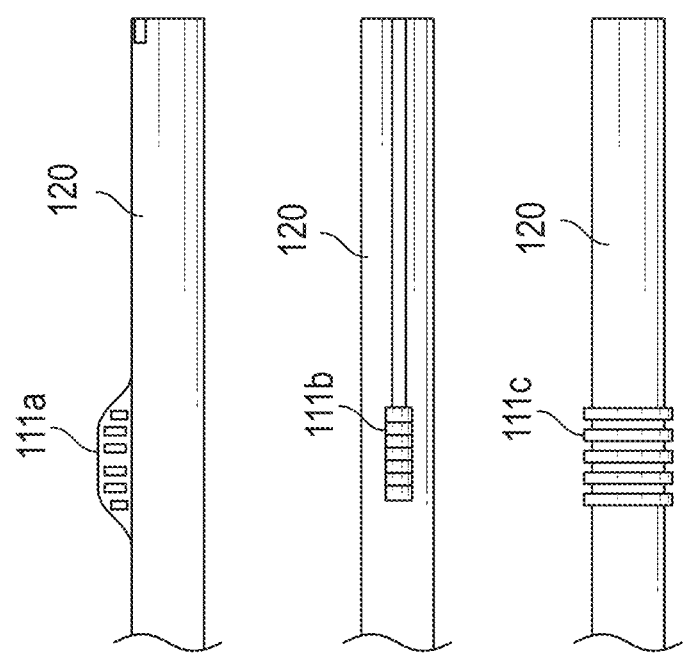
FIG. 6

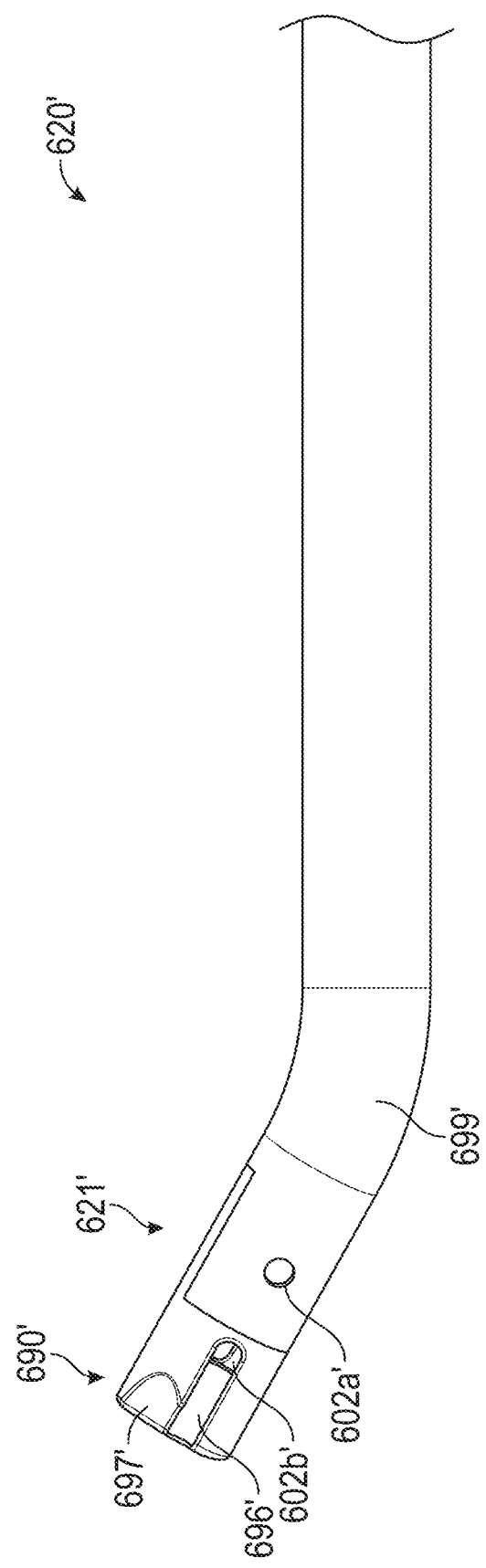

ORTHOPEDIC ARTHROSCOPIC OPTICAL CANNULA SYSTEM

INCORPORATION BY REFERENCE TO ANY PRIORITY APPLICATIONS

This application claims the benefit of priority under 35 U.S.C. § 119 (e) to U.S. Provisional Patent Application No. 63/588,130, filed Oct. 5, 2023, which is hereby incorporated by reference herein in its entirety. Any and all applications for which a foreign or domestic priority claim is identified in the Application Data Sheet as filed with the present application are hereby incorporated by reference under 37 CFR 1.57.

BACKGROUND

Field

This disclosure generally relates to devices, systems, and methods for arthroscopic procedures.

Related Arts

Arthroscopy is a procedure for diagnosing and treating joint problems. A surgeon inserts a small tube or cannula into a joint space through a small incision or portal. A fiberoptic or endoscopic camera is then passed through the portal and used to transmit a high-resolution image of the joint space to a video monitor. Arthroscopy allows the surgeon to see inside your joint without making a large incision. Arthroscopy is used to visualize many joints including the knee, hip, shoulder, ankle, spine, and wrist. Traditional arthroscopy uses a single portal for the endoscope and a second portal to pass instrumentation used for manipulating tissue within the joint space.

SUMMARY

Implementations described herein are directed toward improved orthopedic arthroscopy systems that reduce the number of necessary arthroscopic portals while at the same time improving endoscopic visualization and instrumentation capability within the joint space. Main embodiments of the disclosed systems replace the traditional rod endoscope with a rotatable, optical cannula through which instruments can be used to manipulate tissue and perform surgery. Reusable and disposable implementations of such a system are envisioned. By adding the cannula rotation capability, visualization of instrument tool tip can be easily adjusted by rotation about a longitudinal axis of the cannula. Conventional optically enabled spinal cannulas cannot be rotated independent of the handle. The disclosed system would eliminate the need for unnecessary wrist rotation by the surgeon thereby making it easier to coordinate hand position while performing surgical tasks. Features and aspects of the disclosed technology permit mechanized operation of instrument tools through an endoscope handle that is operated and held with the same hand. This capability frees up the other hand to rotate the cannula via rotation assembly, thus allowing the surgeons tool operating grip and wrist position to remain stationary in a comfortable ergonomic position.

In certain implementations, the electrical wire carrying the camera signal from the cannula tip through the length of the cannula would interface via an electrical coupler (e.g., electrical commutator or service loop) that would allow at least 90 degrees of cannula rotation (or alternatively at least 360 degrees of cannula rotation or unlimited cannula rotation) without interruption of the electrical connection.

In conventional arthroscopic systems, the smaller the endoscope tip diameter, the less optical fibers are dedicated to image capture and the more are required for light delivery. Additionally, conventional spinal arthroscope technology keeps the LED light source and camera chip separate from the arthroscope handle. Light is transferred from an LED source contained within an external box through a long fiberoptic cable to the cannula. In some implementations described herein, the optical camera chip (e.g., complementary metal oxide semiconductor (CMOS), charge coupled device (CCD), lens, or other type of image sensor) is placed at the tip of the arthroscopic cannula. Placement of the optical camera chip at the distal tip can enhance image resolution. This implementation-includes a LED light source contained either within the arthroscope handle or located at the tip of the cannula, thus negating the need for a standalone video rack to hold a stand-alone light source which occupies operating room space and increases equipment expense. Other embodiments provide for a multi-camera chip design with camera sensors angled apart from one another in a divergent fashion. Although the angle of divergence and number of CMOS chips could vary, by utilizing this design, an instrument shaft placed through the cannula working channel can be digitally subtracted from the overall image thereby improving joint space visualization without the need for instrument shaft removal. Alternatively or additionally, integrating multiple camera chips at different angles could allow for a split screen image of the joint space to be presented on the monitor, head mounted display, or portable display device. In other embodiments, through the use of AI (artificial intelligence) technology, multiple 2D images obtained from multiple cameras located at the tip of the cannula could be used to create 3D image or virtual reality representations of an anatomic joint space.

The disclosed embodiments herein allow for at least two types of instrumentation approaches through the optical cannula. The first method involves passing an instrument through the optical cannula from proximal-to-distal. The tool tip in this scenario must remain smaller than the working channel diameter in order to effectively advance the instrument through the cannula. The second method allows for a removable instrument shaft (with distally attached tool tip) to be advanced distal-to-proximal through the cannula. In both scenarios, the proximal end of the tool shaft could be made to engage a portion of a mechanized handle in a manner that permits the surgeon to operate the tool tip attached the distal end of the instrument shaft by squeezing a lever incorporated into the design of the endoscope handle. For those instrument shafts passed from distal-to-proximal, the tool tip can remain larger than the working channel of the cannula thus allowing for greater tool options for a particular surgical application. In some embodiments, the mechanized endoscopic handle would remain in a straight-line orientation to the instrument shaft and allow for an overhand surgeon grip. In other implementations, the endoscope handle may be offset from the long axis of the optical cannula and instrument shaft thereby allowing a surgeon to hold the device in for more of a "pistol grip" fashion. In certain instances, it may be advantageous to utilize traditional arthroscopic forceps (with handles already attached and tool tip size small enough to pass through the disclosed optical cannula). In these scenarios, there would be no need for the mechanized handle portion of the disclosed device. Although most arthroscopic systems currently on the market enable instruments to be passed therethrough, current systems, however, do not have the option of both a passive and active method for instrument engagement and are therefore limited in their surgical application.

Another feature of systems disclosed herein involves a means by which to maintain the ordered, stationary positioning of the electrical, suction, and irrigation hoses off the back of the endoscope handle during surgery. Embodiments of this system utilize a disposable suction/irrigation harness that removably or permanently fits around the cannula in a watertight fashion. Within this harness are circumferential fluid and/or suction chambers that line up with corresponding holes or ports placed through the outer wall of the optical cannula. Inside the cannula, these holes communicate with the suction and irrigation spaces or channels formed between the instrument shaft and cannula wall. In some embodiments, the holes are offset from one another along the circumference of the outer cannula so as to separate the two fluid channels as much as possible. Cannula embodiments that use the inserted instrument shaft rather than an integrated working channel within the cannula to form the fluid channels would maximize the inner diameter of the cannula for passage of larger, rigid or flexible instrument tips, shafts, and micro-debriders. Applying these or similar implementations allow suction and irrigation capabilities to remain constant even during cannula rotation. The perpendicular or angled orientation of traditional side suction/ irrigation ports seen with existing arthroscopic cannula systems would therefore be eliminated. By utilizing this methodology, all hoses and the endoscope cord would remain in stable position even while the cannula is rotated. The hoses and cords could therefore be grouped together and secured in a streamlined bundle off the back of the device thereby improving clutter within the operative field.

In some implementations, the endoscope handle and cannula along with incorporated optics and irrigation/suction channels may be disposable. In these implementations, the electrical coupler connecting the cannula camera wire to the endoscope handle might be housed or included within the suction/irrigation harness along with slack wire (i.e., service loop) to permit rotation of the cannula. In other implementations, the endoscope handle may be reusable, but encased in a manner that would allow for easy cleaning and sterilization. In other embodiments, individual system parts and optical interfaces may be either disposable or reusable. If the optical cannula and endoscope handle are configured for reusable use, the electrical connection might utilize circumferential electrical contact leads or bands around the outer cannula perimeter (i.e., commutators). Still other electrical contact methods to allow free rotation are contemplated. Regardless of reusability, all individual components of the disclosed system would combine in a manner that is intuitive and easy to assemble, disassemble, and clean/ sterilize.

In still other embodiments, the optical, rotatable cannula could be articulating. The direction and angle of articulation could vary, but may be uni-directional or multi-directional with angulation anywhere between zero and 180 degrees. Activation of the articulation might involve a dial, a lever, a telescoping mechanism, a robotic mechanism, or some other integrated means incorporated within or attached to the endoscope handle or optical forceps system. Such a mechanism would nearly eliminate the need to lever the cannula in order to access poorly visualize areas of the joint space. This in turn would serve to minimize tissue damage and instrument breakage. An articulating cannula would further enable and expand the use of flexible instrument shafts and micro-debriders. Such an advancement could be applied to other surgical specialties including but not limited to ENT, neurosurgery, general surgery, urology, OB/GYN, plastic surgery, podiatry, veterinary, etc. In some implementations one or more notches might be incorporated into the side or tip of the cannula to permit facilitated articulation of the instrument shaft as it exits the distal cannula.

In some implementations, an optical cannula system including a cannula (e.g., curved or straight), a body, a first tube, a second, tube, and a valve assembly is disclosed. The cannula includes a proximal portion, a distal end, and an axis extending between the proximal portion and the distal end. The cannula further includes an outer cannula wall and one or more inner cannula walls. The outer cannula wall defines an interior space extending along the axis. The one or more inner cannula walls are disposed within the outer cannula wall and extend along the axis. The one or more inner cannula walls divide the interior space into a first channel and a second channel. The body is configured to receive the proximal portion of the cannula. The first tube and the second tube extend from the body. The valve assembly is connected to the body. The valve assembly has a first configuration in which the first tube is in fluid communication with the first channel and the second tube is in fluid communication with the second channel. The valve assembly has a second configuration in which the first tube is in fluid communication with the second channel and the second tube is in fluid communication with the first channel.

In some implementations, an optical cannula system including a cannula, and a body is disclosed. The cannula, which can be either straight or curved, includes an outer cannula wall having a proximal portion and a distal end, a first channel, a second channel, and one or more internal walls. The body is configured to receive the proximal portion of the cannula. The first channel is within the outer cannula wall. The first channel is configured for suction in a first configuration of the optical cannula system and configured for irrigation in a second configuration of the optical cannula system. The second channel is within the outer cannula wall. The second channel is configured for irrigation in the first configuration and suction in the second configuration. The one or more internal walls are within the outer cannula wall. The one or more internal walls extend at least partially along a length of the outer cannula wall between the proximal portion and the distal end. The one or more internal walls at least partially define the first channel and the second channel.

In some implementations, an optical cannula system including a handle, and a cannula is disclosed. The handle includes a body, a first port, and a second port. The first port extends at least partially through the body. The first port is configured to connect to a first hose. The second port extends at least partially through the body. The second port is configured to connect to a second hose. The cannula includes an outer cannula wall, a first channel, and a second channel. The outer cannula wall has a proximal portion and a distal end. The proximal portion is configured to be disposed within the body of the handle. The first channel is within the outer cannula wall. The first channel is configured to be in fluid communication with the first port in a first configuration and the second port in a second configuration. The second channel is within the outer cannula wall. The second channel is configured to be in fluid communication with the second port in the first configuration and the first port in the second configuration.

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such vies as "top," "bottom," "front," "rear," or "side" views, such references are merely descriptive and do not imply or require that the disclosed technology be implemented or used in a particular special orientation unless explicitly stated otherwise.

FIG. 6 shows examples of electrical couplers for image data transmission in accordance with implementations of the disclosure.

FIG. 40 shows a curved distal end of the cannula of the endoscope of FIG. 33, in accordance with implementations of the disclosure.

DETAILED DESCRIPTION

Figure 1:
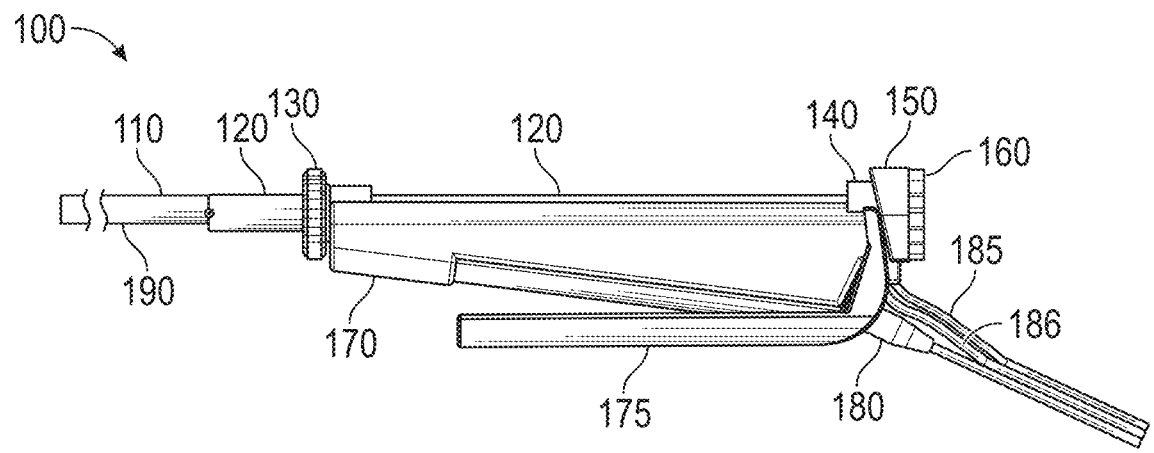
FIG. 1 shows a side view of an optical cannula system, in accordance with implementations of the disclosure.

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Arthroscopy is a procedure for diagnosing and treating joint problems. A surgeon inserts a small tube or cannula into a joint space through a small incision or portal. A fiberoptic or endoscopic camera is then passed through the portal and used to transmit a high-resolution image of the joint space to a video monitor. Arthroscopy allows the surgeon to see inside a patient's joint without making a large incision. Arthroscopy is used to visualize many joints including the knee, hip, shoulder, ankle, spine, and wrist. Traditional arthroscopy uses a single portal for the endoscope (with or without irrigation and suction) and a second portal to pass instrumentation used for manipulating tissue within the joint space. A current trend in the surgical orthopedic marketplace is the miniaturization of arthroscopes and associated instrument forceps. Newer arthroscopic systems such as the Nanoscope system produced by Arthrex uses a very small endoscope cannula in one portal and a second portal to pass miniaturized forceps used for tissue manipulation through a second portal.

Smaller incisions and fewer portals allow for improved patient comfort, lower cost, decreased operative time, and the capability of performing arthroscopic procedures in the office rather than in the hospital or ambulatory surgery center setting. Until recently, few systems have even contemplated visualizing and manipulating tissue through a single portal. The Stryker SPA system uses a dual cannula device that is inserted through a single portal incision. Unfortunately, that portal is made large to accommodate both cannulas, one for the endoscope and the other for a powered micro-debrider. Having to manipulate two cannulas through a single portal is technically difficult.

Arthroscopy generally requires irrigation fluid and suction in order to clear debris and inflate the joint for improved visualization. Suction and irrigation hoses attach to connectors on the outside of the rigid cannula through which the endoscope is passed. These hoses are oriented perpendicular to the long axis of the cannula and extend sideways off of the cannula thereby adding to surgical clutter on the field and surgeon frustration during the procedure. The camera head cable and fiberoptic light cable further add to the number of cables and hoses intertangled and within the surgical field. When using a powered suction micro-debrider through a second portal, two more cables/hoses are added to the mix. As such, it is not uncommon for there to be six hoses/cords all competing for space within the operative field. Because the surgeon must rotate and twist the scope during the procedure to improve visualization, the hoses often get tangled and twisted making the case more difficult and frustrating for the surgeon and scrub nurse.

Conventional arthroscopy used standard rod fiberoptic endoscopes for visualization. These endoscopes have distal tips that can visualize at different angles depending on the endoscope. Some examples include zero, thirty, seventy-degree rigid endoscopes. When endoscopes having angled fields of view are passed into a joint space, the surgeon must rotate the scope along its horizontal axis in order to visual the entire joint space. The surgeon must also lever the rod of the scope in a multitude of directions in order to capture a larger visual field. This rocking or levered manipulation of the scope as it passes through the portal can result in greater trauma to the incision site and joint space not to mention damage to the scope and increased surgeon fatigue.

Traditionally only a single instrument can be passed through an arthroscopic portal at one time. Some spinal arthroscopic systems are beginning to utilize single, rigid fiberoptic cannulas through which instruments can be passed (JOIMAX® minimally invasive spinal surgery). These systems utilize fiber optic strands to carry the image from the joint space through the cannula to the camera head CMOS chip that is attached to the proximal end of the instrument cannula. This results in an image quality that is potentially limited by the number of optical fibers delivering the image to the CMOS sensor. With the improvements in the miniaturization and resolution of CMOS chip technology, an endoscope camera/CMOS chip that is located at the tip of the cannula would be advantageous. Likewise, these optical spinal cannulas require rotating the entire handle in order to change the viewing angle or view around an instrument shaft. Such an action causes the hoses and cords that come off the handle to flop around the back of the handle while the cannula is being turned. These cannulas are also larger in diameter and in all instances require instruments to be passed through the cannula from proximal-to-distal and be operated by a second hand.

In some orthopedic arthroscopic procedures, a second instrument is required to effectively manage a surgical task. Should a second instrument be required, it becomes necessary to create a third incision/portal to accommodate the second instrument. This adds to surgical time, tissue injury, and patient discomfort. It is apparent that any means by which a surgeon can improve image resolution, limit the number of surgical portals, decrease incision size, reduce the need for endoscope rotation and/or levering, and minimize the number of surgical cords/hoses on the operative field would be a beneficial and welcomed advancement for the worldwide surgical marketplace.

As noted previously, current implementations of orthopedic arthroscopic cannulas, arthroscopic instruments, and arthroscopic endoscopes (arthroscopes) have limitations with respect to the ability to operate and visualize through a single portal and cannula. Current systems are cumbersome, difficult to set-up, require expanded video and stacked accessory components to operate, and are not integrated in a user-friendly manner. Other limitations of current arthroscopic systems include limited visualization within the joint space, need for levering of the arthroscope to access different portions of the joint space, need for a second or third incision/portal for instrument access, suction hose, irrigation tubing, and electrical cable management, awkward hand/wrist positioning for the surgeon, and the inability to rotate the camera orientation with respect to the instrument shaft and tool tip (and vice-versa).

To this end, implementations of this disclosure are directed to an improved arthroscopic system design that corrects these current deficiencies while at the same time reducing the number of necessary portals required for a particular procedure. In effect, implementations of this disclosure allow the surgeon to free-up one hand and at least one surgical portal. In so doing, the surgeon can manipulate the extremity with one hand while visualizing and using mechanical instrumentation with the other. The rotational cannula design enables the image angle to be changed without having to turn the whole wrist or endoscopic handle. In this simplified and ergonomic manner, physician fatigue is improved and tasks that usually require a second assistant are minimized. Additionally, operative time is decreased, patient comfort is increased, fewer parts require sterilization, optical clarity is improved, and the overall cost of the procedure is reduced. Implementations of the disclosed system also allow the surgeon to perform instrumentation with tools that are larger than the diameter on the optical cannula while at the same time maintaining optical visualization of the tool tip. The disclosed implementations herein present a better "mouse trap" and improved options for surgical instrumentation and visualization during arthroscopy. Importantly, implementations of this device will make it easier to transition surgical procedures out of the hospital and ambulatory care centers and into the physician office, thereby decreasing facility and anesthesia costs and improving surgeon efficiency and patient satisfaction.

Figure 2:
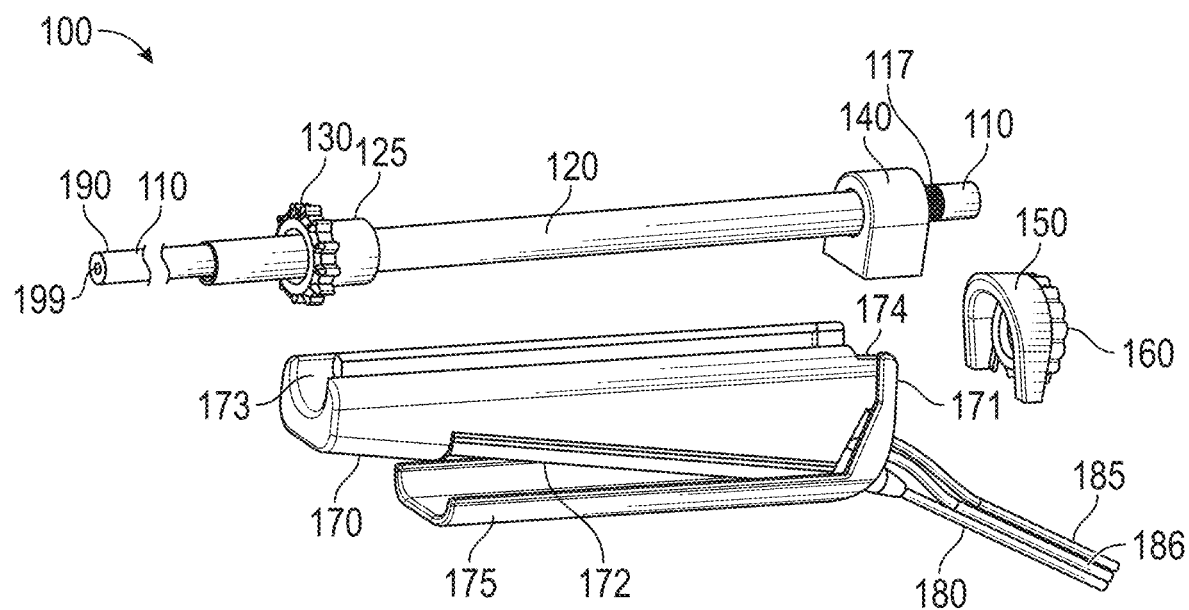
FIG. 2 shows an exploded view of the optical cannula system shown in FIG. 1, in accordance with implementations of the disclosure.

FIGS. 1-2 illustrate implementations of a rotatable, optical cannula system 100 in accordance with the disclosure. As illustrated in FIG. 1-2, the optical cannula system 100 may include a reusable or disposable cannula 120 with an outer turn dial 130. The cannula fits into an elongate, semicircular indentation (FIG. 10A, 178) located on the top surface of the endoscope handle 170. The turn dial 130 has a collar extension 125 that likewise snaps into a molded indentation (FIG. 2, 173) within the inner surface of the distal endoscope handle 170. When attached to the endoscope handle, rotation of the turn dial 130 causes the optical cannula to turn in either clockwise or counterclockwise in a circumferential fashion. On the proximal end of the cannula 120 there is a suction/irrigation harness 140 that is permanently or removably attached to the optical cannula 120. The cannula 120 can turn freely within the irrigation harness 140 when secured to the endoscope handle 170. Within the proximal aspect of the endoscope handle 170 there is a molded indentation designed to receive the irrigation harness 140 utilizing a "snap-in" mechanism or alternative means such as magnets, clips, clamps, grooves, or other means not limited to the implementations described herein. Not depicted in FIG. 1-2 is an electrical coupler located along the bottom surface of the irrigation harness 140 and a separate mating electrical coupler within the proximal molded indentation 174 of handle 170 (see FIG. 10A, endoscope coupler 177).

In certain implementations, a removable lever 175 is attached to the endoscope handle 170. Along the proximal aspect of the lever there are bilateral extensions 171. These lever extensions engage a removable locking key 150 that is designed to integrate with the back end of an instrument shaft 110. The instrument shaft 110 is comprised of an inner shaft 199 and an outer shaft 190. Movement of the inner instrument shaft 199 within the outer shaft 190 causes the mechanized movement of the tool tip attached to the end of the instrument shaft 110 (not depicted). Hinged movement of the lever against the endoscope body causes the locking key to reversibly move the inner instrument shaft in a direction opposite from the outer instrument shaft. In so doing, the tool tip is actuated. In certain scenarios when the mechanized aspects of the endoscope handle are not required, the instrument lever can be removed or snapped into a conforming indentation molded into the body of the endoscope handle 170. Securing the lever 175 into the handle indentation 172 could be facilitated by a magnet or alternative mechanism depending on the implementation.

On the back of the locking key 150 there is a rotatable instrument shaft turn dial 160 that engages internally with a small circular gear 117 formed within a small horizontal segment of the outer instrument shaft 110. The instrument shaft turn dial 160 rotates independently from the locking key 150. When the locking key 150 is fully engaged, the gear projections within the inner circumference of the turn dial engage the gear projections on the outer instrument shaft in a manner that allows for easy rotation of the instrument shaft as it exits the proximal end of the optical cannula. Rotation of the instrument shaft is thereby independent of the optical cannula rotation performed by rotating a separate turn dial 130 located on the opposite, more distal end of the cannula.

Figure 11:
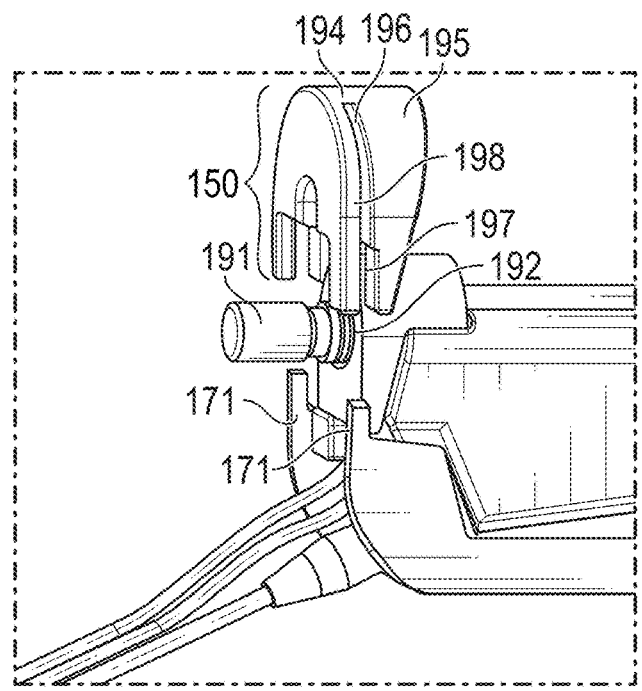
FIG. 11 shows the instrument locking key prior to its engagement with the instrument shaft and lever component of the endoscope handle, in accordance with implementations of the disclosure.

A removable endoscope electrical cable 180 is shown to connect to the proximal undersurface of the endoscope handle 170. Suction and irrigation hoses 185, 186 attach to the undersurface of the suction/irrigation harness (FIG. 11). Various embodiments of how the suction and irrigation hoses interact with the suction/irrigation harness 140 are envisioned and described later herein. It is apparent however that the streamlined orientation of all electrical cables and suction/irrigation hoses is favorable when compared to current systems.

Figure 3:
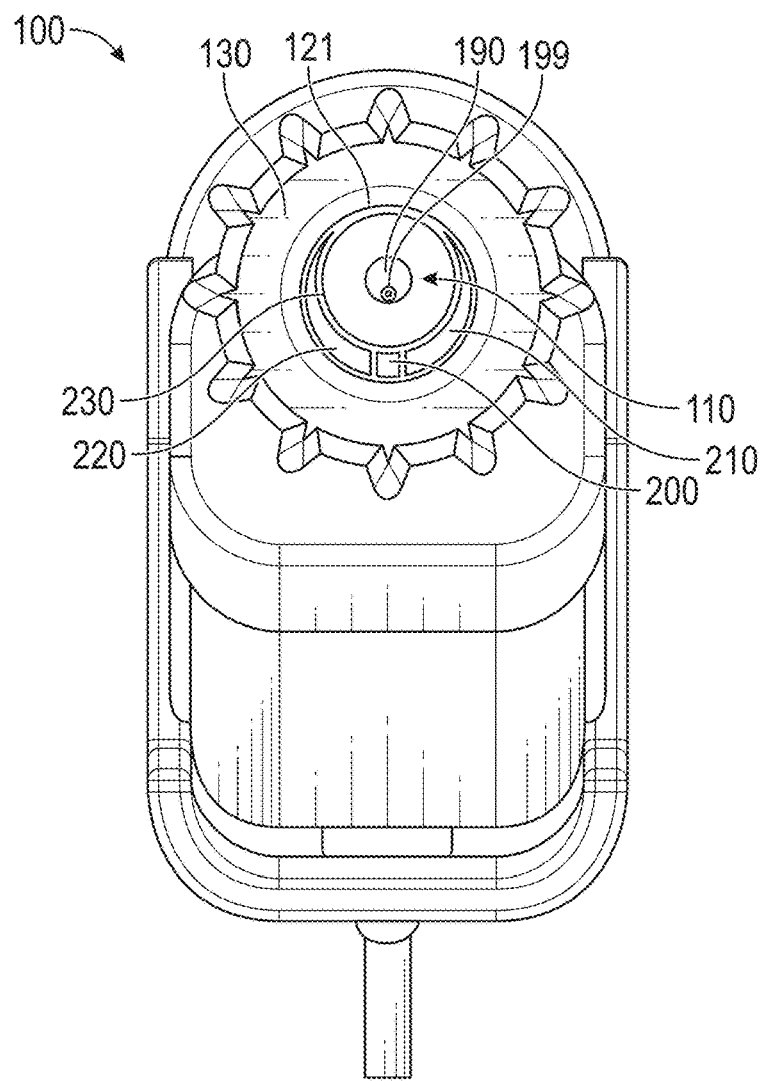
FIG. 3 shows a front view of the optical cannula system of FIG. 1, in accordance with implementations of the disclosure.

FIG. 3 shows a front view of the disclosed optical cannula system 100. FIG. 3 highlights the internal features of the optical cannula 120. In this implementation, a single camera CMOS chip 200 is seen just inside the periphery of the cannula. It is important to note that in these implementations the camera chip is located at the distal tip of the cannula and not inside a separate camera head attached to the proximal end of the cannula or endoscope handle. Positioning of the CMOS sensor at the tip of the cannula negates any loss of image resolution seen with conventional systems that use limited optical fibers to carry the image to a distal sensor. As imaging technology advances and the size of CMOS chips get smaller and resolution improves, the implementations of the disclosed system will show progressive quality improvement of displayed images when compared to systems that use conventional fiberoptic technology.

FIG. 3 shows irrigation 210 and suction 220 channels oriented peripherally within the lumen or cannula 120. These irrigation and suction channels are carried horizontally along the length of the cannula and eventually end in holes in the outer cannula that communicate with fluid chambers located within the irrigation/suction harness 140 situated along the back end of the cannula. The optical cannula irrigation and suction channel borders are formed by the instrument shaft 110 and/or instrument working channel 230 internally, the optical cannula wall 121 externally, and the CMOS chip and optical light fibers centrally. In other implementations, an LED emitter placed next to the CMOS chip might be used instead of optical fibers. In some implementations, there may not be a discrete internal working cannula that is incorporated into the central lumen of the outer cannula and in other implementations the instrument shaft alone could act as the internal border for the cannulas' irrigation and suction channels.

Figure 4:
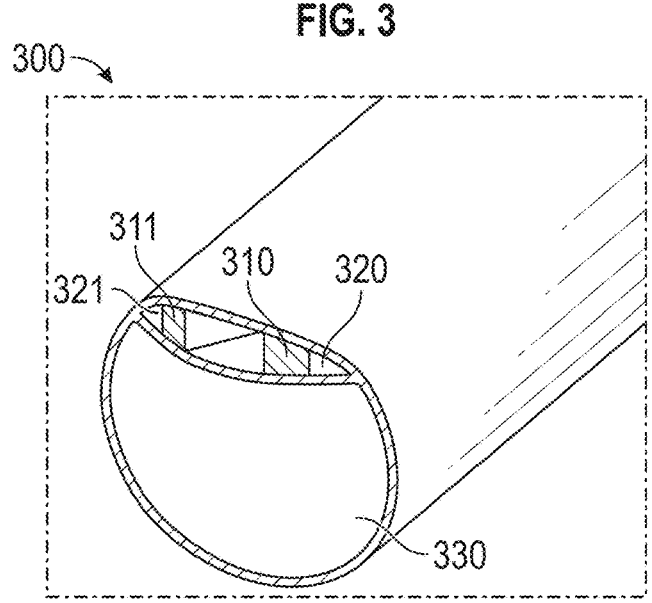
FIG. 4 shows a perspective view of a dual camera cannula embodiment of FIG. 1, in accordance with implementations of the disclosure.

FIG. 4 shows a perspective view of a dual camera chip optical cannula 300, which can be one implementation of the cannula 120. Small gaps 320, 321 laterally adjacent to the CMOS chips 310, 311 could be used to accommodate the optical light fibers or LED emitters necessary for joint illumination. By utilizing two separate CMOS chips in a divergent orientation, both camera images could be displayed individually or side by side on a split image monitor. Each image would provide a different viewing angle of the anatomical landscape. Alternatively, the images could be digitally combined or "stitched" together in a manner that would create a larger, panoramic field of view. In this implementation, the CMOS chips of optical cannula embodiment 300 are oriented 30 degrees divergent from center. Cannula systems with varying angles of camera chip divergence using two or more camera CMOS chips are envisioned. By incorporating multiple camera chips into the tip of the cannula, multiple areas of the joint space could be visualized simultaneously and displayed in a compartmentalized, 3D, or panoramic fashion on a monitor display. Conventional arthroscopic systems have limited fields of view confined by the angulation of the rigid scope lens.

Figure 5:
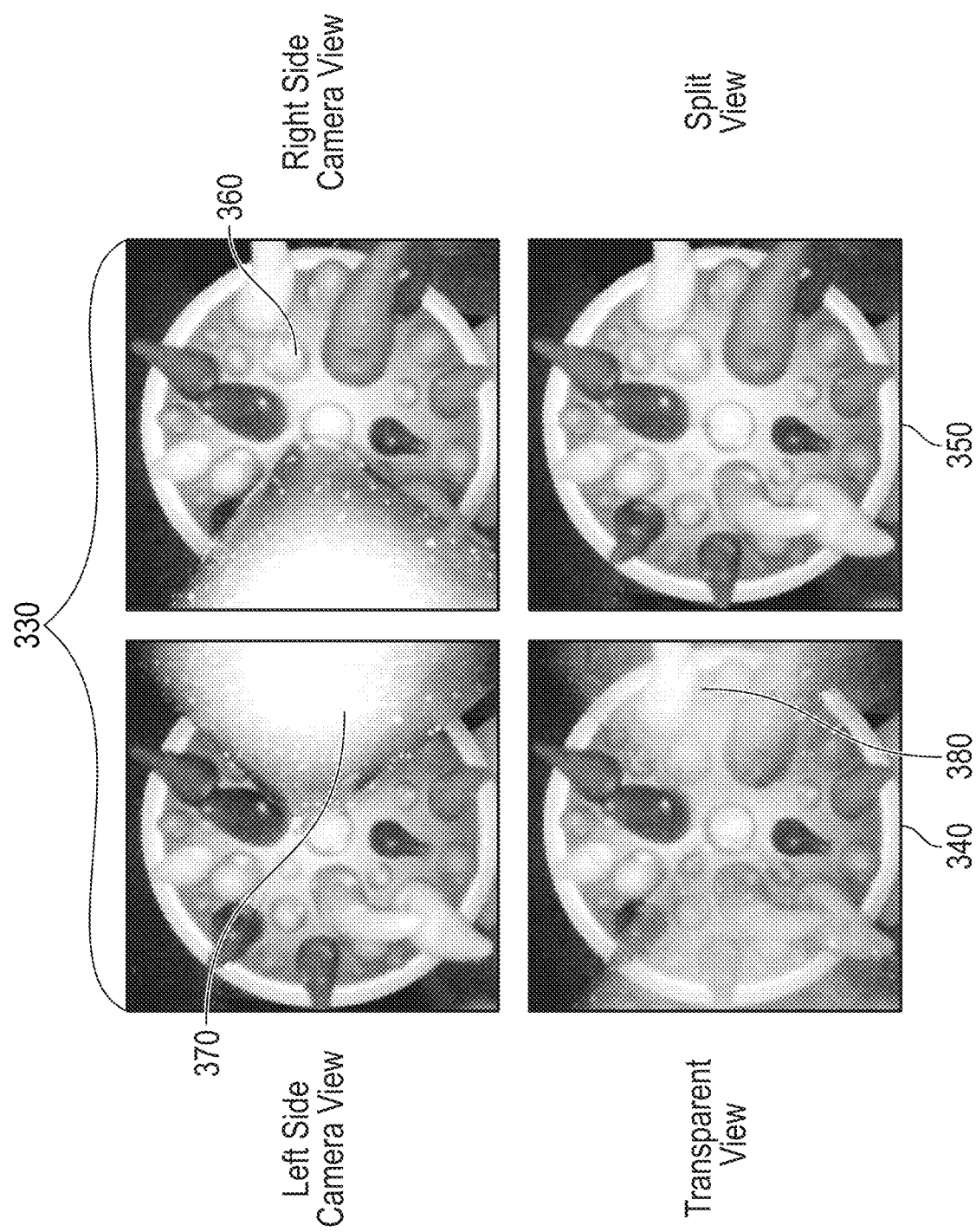
FIG. 5 shows examples of image cancellation obtained from the dual camera cannula of FIG. 2, in accordance with implementations of the disclosure.

FIG. 5 shows an example diagrammatic representation of image cancellation using a dual camera chip cannula configuration. In this application, computerized digital manipulation of the combined CMOS camera images allows for display cancellation/removal of the instrument shaft occupying the central aspect of the operative view. Split screen images 330 of two unaltered pictures created by divergent CMOS sensors are located on the top of the diagram. The visualized object 360 is obscured by the instrument shaft 370 noted centrally along the inner aspect of each top picture. The lower left picture 340 combines the digitally manipulated pictures into a single picture in a manner that shows a transparent, but still visible outline of the instrument shaft 380. The lower right picture 350 shows a digitally enhanced image with the instrument shaft completely removed from the scene. The photographed object remains visually complete as if the instrument shaft was never there. One can see how image cancellation technology could be used to improve joint space visualization during a reduced portal surgical procedure by digitally removing and reinserting the instrument shaft from the displayed image without actually removing the instrument shaft from the joint space.

FIG. 6 shows various implementations of how the rotatable, optical cannula 120 could interact with a stationary electrical couplers 111a, 111b, 111c embedded within an endoscope handle 170. The stationary electrical couplers 111a, 111b can include contacts to which wires can be attached (e.g., with a service loop connection with the cannula 120) to provide continuous electrical contact with the shaft 110 and camera chip 200. The stationary electrical coupler 111c can include circumferential contacts which form part of a commutator. Another portion of the cannula system (e.g., endoscope handle 170) can include contacts aligned with each of the circumferential contacts to provide continuous electrical contact with the shaft 110 and camera chip 200.

Figure 7:
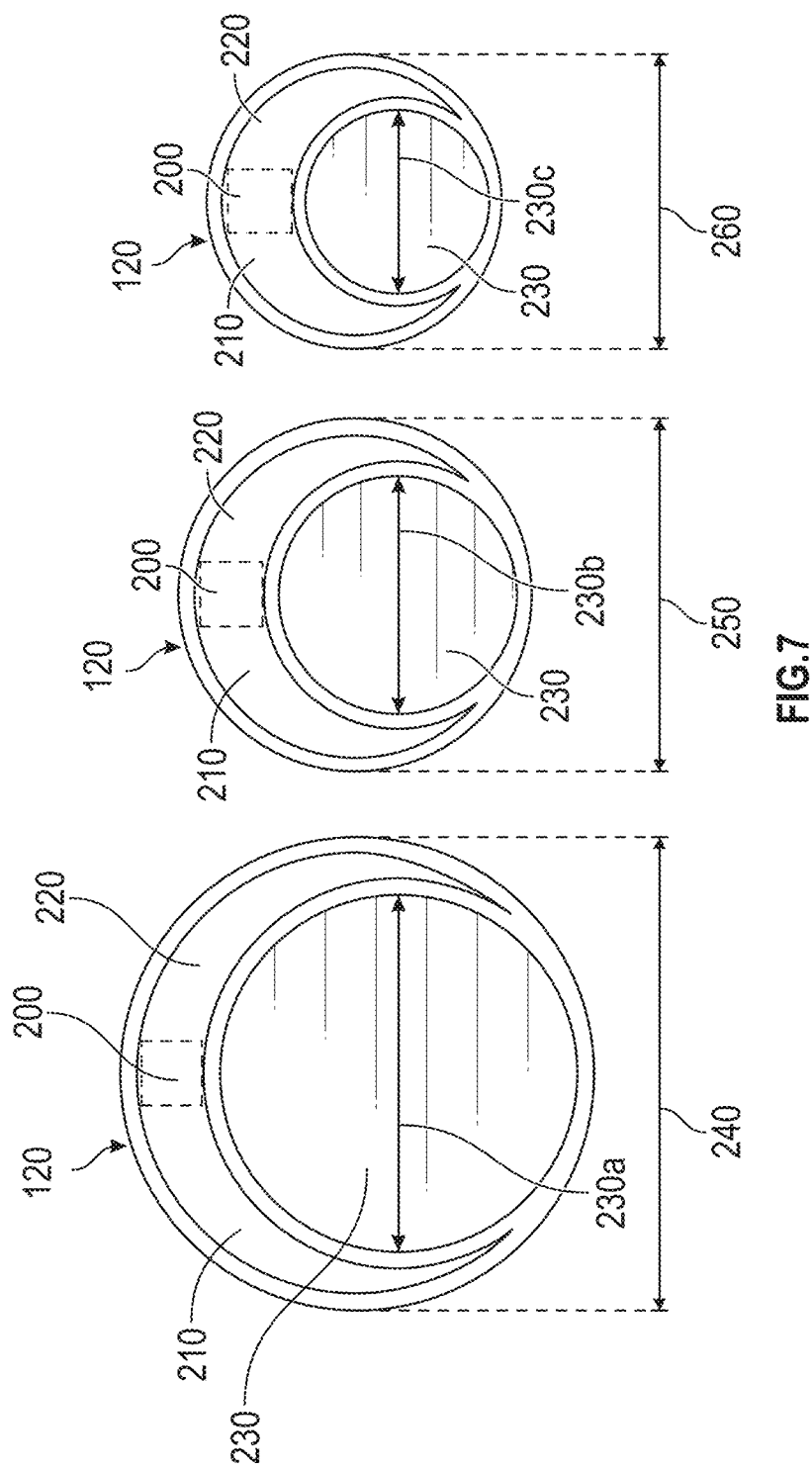
FIG. 7 shows a front view of an optical cannula containing a camera chip and the resultant spatial relationships from its position with the cannula, in accordance with implementations of the disclosure.

FIG. 7 shows a visual representation of how a one-millimeter camera chip 200 can affect the size of the inner working channel 230, irrigation channel 210, and suction channel 220 of an optical cannula. A cannula 120 with outer diameters 240a of 8 mm, a working channel 230 with diameter 230a of 6.1 mm, an outer diameter 250 of 6 mm, a working channel 230 with diameter 230b of 4.1 mm, an outer diameter 260 of 4 mm, and a working channel 230 with diameter 230c of 2.1 mm are respectively included for comparison.

Figure 8:
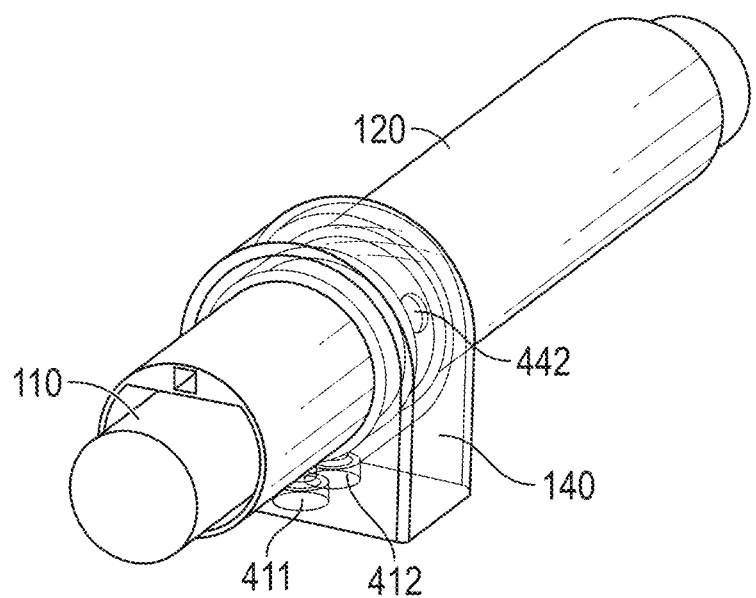
FIG. 8 shows a perspective view of the optical cannula of FIG. 1 attached to a suction/irrigation harness, in accordance with implementations of the disclosure, in accordance with implementations of the disclosure.
Figure 9:
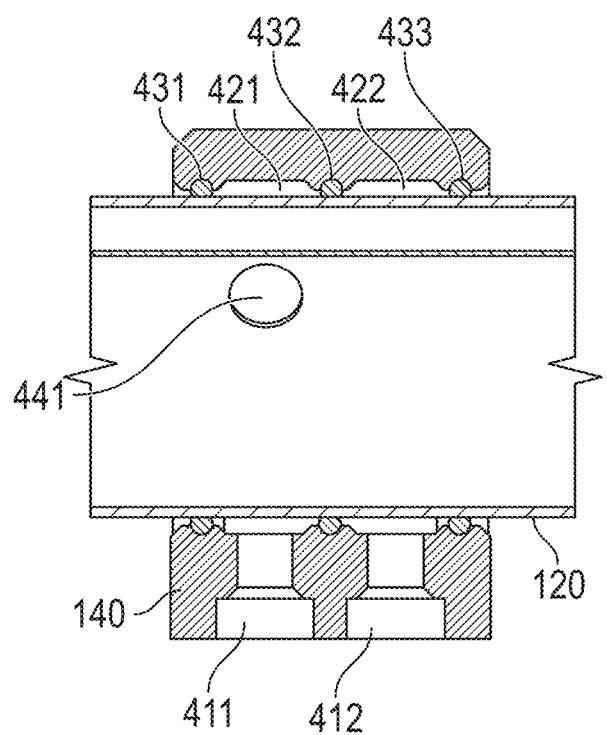
FIG. 9 shows a sagittal view through the cannula and suction/irrigation harness depicted in FIG. 8, in accordance with implementations of the disclosure.

Conventional arthroscopic cannulas typically require suction and/or irrigation ports that are integrated into the side wall of the cannula. These ports typically have shut-off valves/levers that regulate the flow of fluid through the cannula. Often these ports are oriented between 30 and 90 degrees away from the longitudinal axis of the cannula. Implementations of the disclosed system use an alternative means for directing suction and irrigation into and out of the cannula. FIGS. 8-9 show respective transparent and sagittal views of a suction/irrigation harness 140 interacting with the optical cannula 120.

Instead of using fixated ports on the sides of the cannula, the disclosed cannula system 100 takes advantage of the rotational nature of the cannula and uses two independent fluid ports 411, 412 to drain two separate fluid or suction channels 421, 422, respectively, located within the interior circumference of the harness 140. A series of rubber seals 431, 432, 433 separate the two harness channels from one another and maintain a watertight seal against the cannula wall. A first port 441 within the outer cannula wall lines up with one of the channels inside of the suction/irrigation harness 140 and provides fluid or suction access between either the suction channel 220 or the irrigation channel 210 spaced within the cannula interior. A second port 442, which may be offset longitudinally and/or circumferentially from the first port 441, provides access to the second harness chamber 422. By offsetting the ports within the cannula wall and separating the harness channels, the suction and irrigation channels remain separate from one another. When the optical cannula 120 is rotated, ports 441, 442 maintain communication with the corresponding interior fluid channels 421, 422 of the harness 140 during the rotation.

In some embodiments, there may be a rubber seal or projection attached to the outer cannula wall that lines up with one or more of the channels within the suction/irrigation harness. When the cannula is rotated into a specific circumferential position, these projections/seals could be used to seal the irrigation or suction ports 411, 412 and prevent further fluid movement through that respective port. Alternatively, a more traditional valve mechanism could be incorporated into or just outside of the harness ports 411, 412 perhaps by a mechanical extension off of the port opening thus regulating fluid inflow or egress in a more traditional manner. Other methods of regulating fluid and suction flow through the harness ports are contemplated.

Figure 10A:
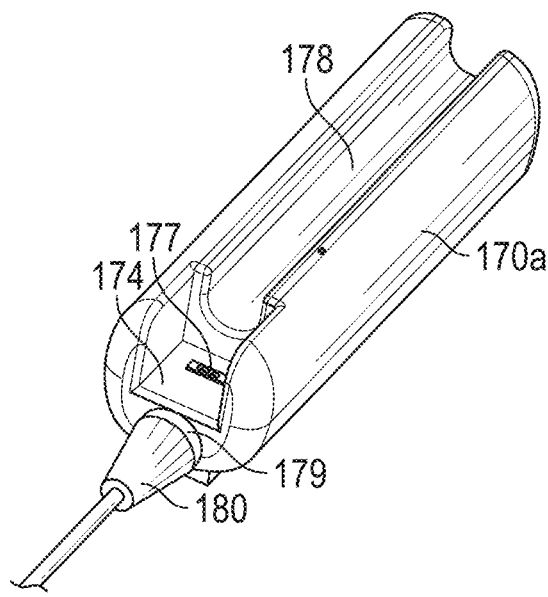
FIG. 10A shows a perspective view of an endoscope implementation with an electrical cable attached, in accordance with implementations of the disclosure.

One aspect of the optical cannula system 100 described herein is unique when compared to conventional arthroscopic systems because it combines rotational cannula optics, mechanical activation of tool tips, suction irrigation, and a fully integrated endoscope into a single hand-held device. FIG. 10A shows a simplified schematic highlighting of one alternative endoscope handle 170a with an electrical cable 180 attached to a receiving coupler 179. The endoscope handle 170a has a molded cutout 174 (e.g., rectangular) incorporated into the endoscope housing meant to receive the irrigation/suction harness 140 described in FIGS. 8-9. An electrical pathway may be provided for transmitting the image data from the camera chip located at the distal end of the cannula, through the length of the cannula to a slack wire within the suction/irrigation harness (not shown). The slack wire (not shown) connects to an electrical coupler located on the flat undersurface of the harness which contacts an endoscope coupler 177 located on the bottom of the endoscope harness cutout 174. The electrical coupler can include an image processing module that receives the signal through the slack wire (or commutator). The image processing module can be disposed within the handle 170a (e.g., internally). The electrical coupler can also be connected with the endoscope coupler 177. Accordingly, the handle 170a can be reusable to reduce costs of the assembly. Alternatively, the image data then transmits through the endoscope coupler 177 to the electrical cable 180 receiving coupler 179 and then to the endoscope cord which transmits the signal to an image processing control board located off of the operative field.

Figure 10B:
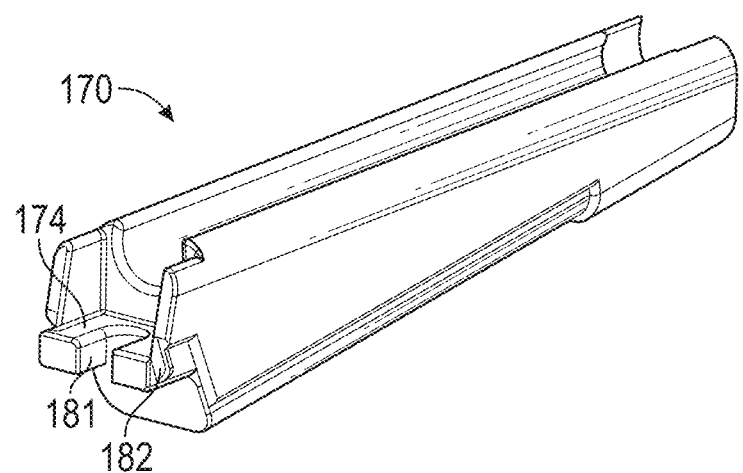
FIG. 10B shows a perspective view of an endoscope handle illustrating the various cutouts and indentations designed to fit various other components of the optical cannula system of FIG. 1, in accordance with implementations of the disclosure.
Figure 12:
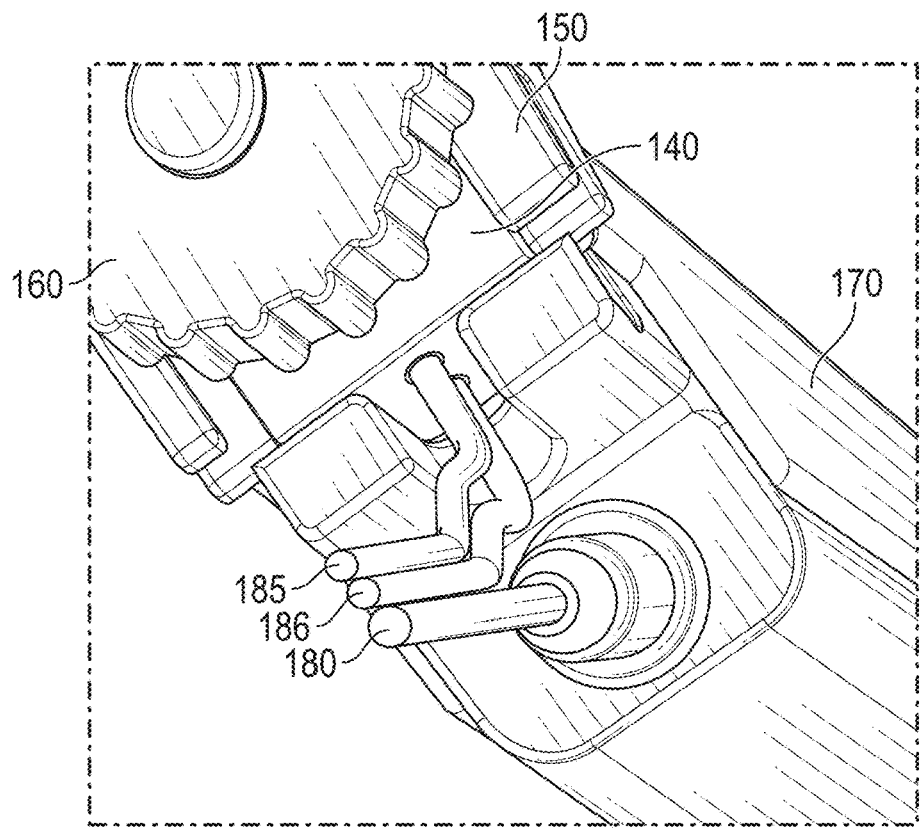
FIG. 12 shows a bottom view of the optical cannula system of FIG. 1 illustrating a streamlined design of the endoscope cord and suction/irrigation hoses as they exit the device, in accordance with implementations of the disclosure.

FIG. 10B shows a more detailed representation of an endoscope handle embodiment shown without the electrical connectors. A curvilinear cutout 181 is seen within the base of the harness indentation 174 that allows suction and irrigation tubes to pass through the bottom of the endoscope handle. This spatial relationship between the endoscope handle and the cords exiting the suction/irrigation harness is better appreciated in FIGS. 11-12. The suction/irrigation tubes 185, 186 can depart the endoscope handle in an orientation that allows for the tubes and electrical cable 180 to exit the device in a parallel, streamlined fashion (FIG. 12, 186). In one implementation, two semicircular indentations 182 may be incorporated into side projections along the outer base of the harness indentation 174. These indentations would receive small circular projections (not shown in the diagram) located along the medial aspect of the lever extensions (FIG. 2, 171) along the back end of the endoscope lever 175. The projections would be located in the mid aspect of the lever extension and not at the very end of the extension. Small circular projections would act to anchor the lever to the endoscope handle while at the same time allowing the lever 175 to hinge off of the proximal aspect of the endoscope handle.

Certain implementations and embodiments of the disclosed system allow for mechanical activation of instrument tool tips. Any of a variety of tool tips may be attached to an instrument shaft. For instrument tool tips that are too large to pass through the inner diameter of the optical cannula working channel, shafts could be inserted from distal-to-proximal into the optical cannula. Conversely, if the instrument tool tip is small enough to pass through the cannula, then the instrument shaft could be passed from either proximal-to-distal, or distal-to-proximal. In either instance, the intent is to work the instrument tool tip by the lever mechanism incorporated into the endoscope handle. Prior art has demonstrated means by which a mechanized handle can operate interchangeable tool tips and instrument shafts in a manner utilizing two integrated sliding instrument shafts, one inside the other. The outer circular shaft has a central channel through which a smaller diameter shaft can move back and forth. The movement interaction between the two instrument shaft components enables the tool tip to be opened and closed.

Figure 13:
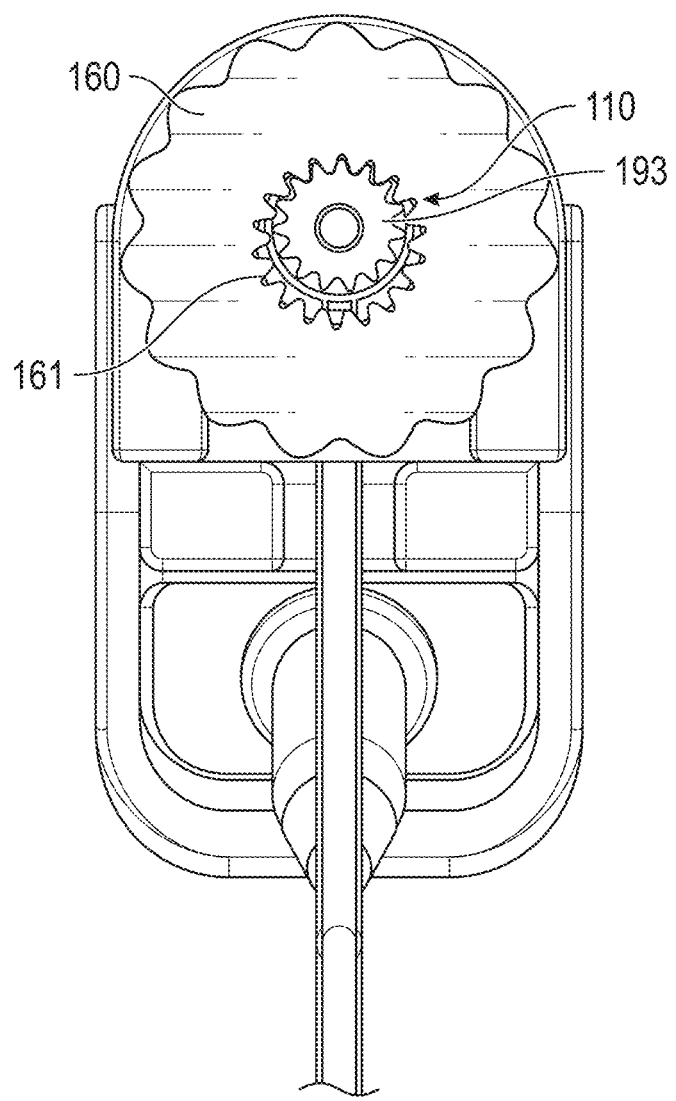
FIG. 13 shows a coronal, cut-away rear view of the optical cannula system of FIG. 1, in accordance with implementations of the disclosure.
Figures 14, 15:
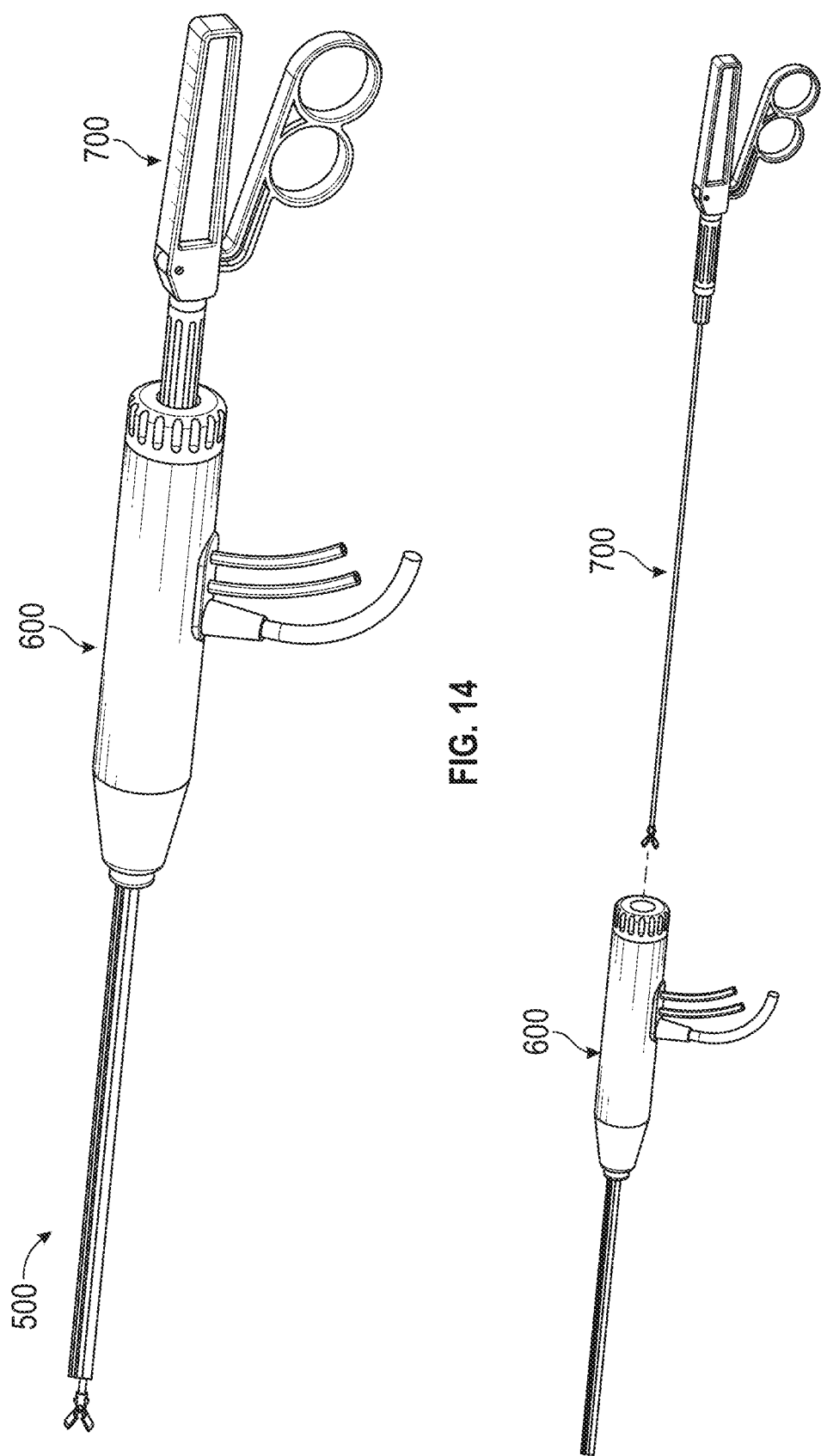
FIG. 14 illustrates an embodiment of an optical cannula system, in accordance with implementations of the disclosure.
FIG. 15 shows the optical cannula system of FIG. 14 including an endoscope and a tool, in accordance with implementations of the disclosure.
Figure 16:
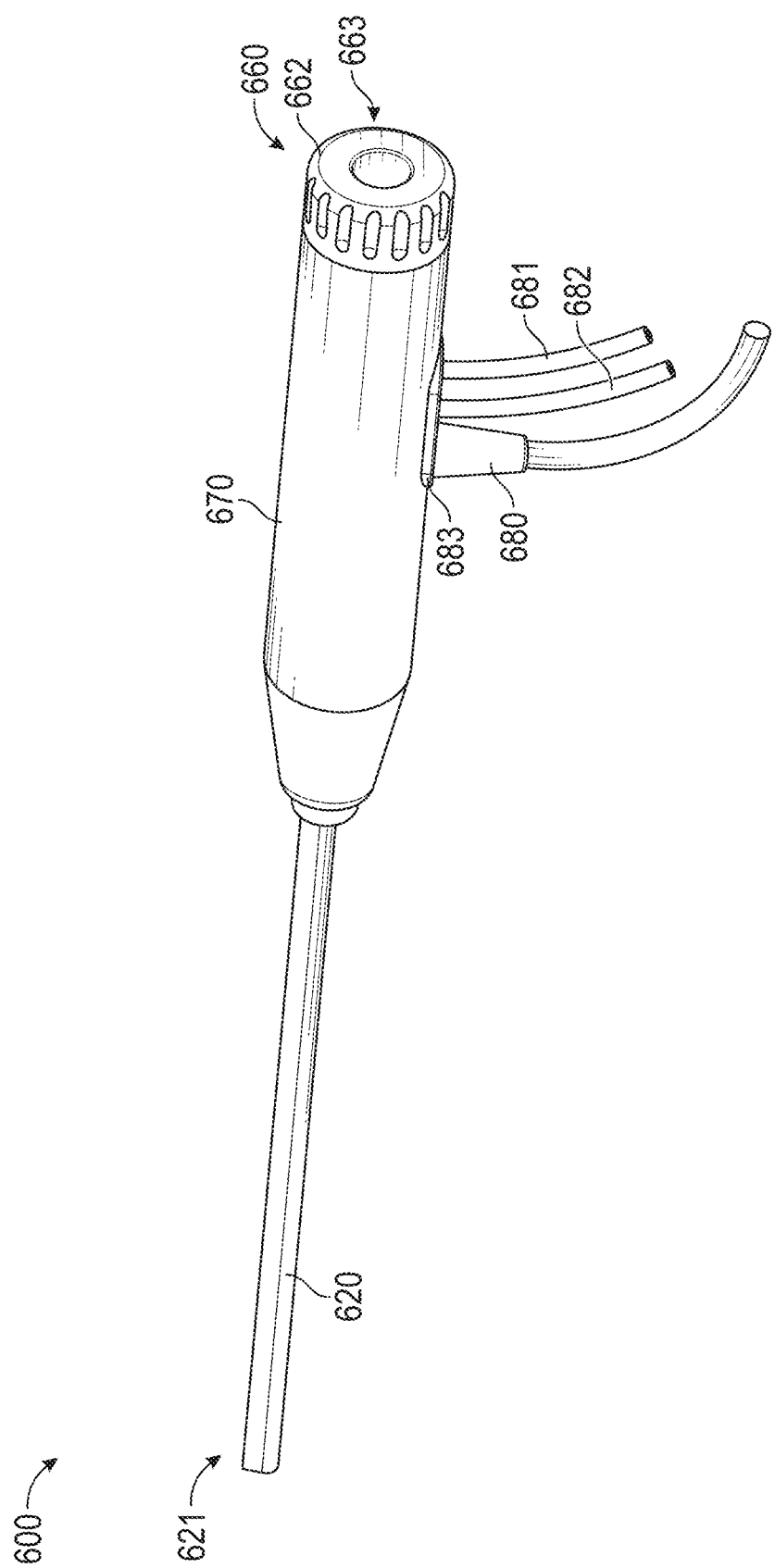
FIG. 16 shows the endoscope of the optical cannula system of FIG. 14, in accordance with implementations of the disclosure.

FIG. 11 shows an instrument shaft protruding out the proximal end of the optical cannula. In this implementation, the back end of the inner shaft 191 has an enlarged posterior extension attached to the inner instrument shaft component. The implementation diagramed in FIG. 13, shows this widened shaft segment fashioned into a gear type configuration 193. Such a configuration would facilitate precise rotation of the instrument shaft 110 within the cannula 120. In these and other envisioned implementations, the gear teeth 193 located on the back end of the instrument shaft 110 could integrate with gear teeth 161 located within the central opening of a rotatable, instrument shaft turn dial 160. The ability to independently rotate the instrument shaft and corresponding tool tip in a manner independent from the position of the optical camera chip (which itself is independently rotatable) would provide surgeons expanded visualization capabilities beyond that offered by traditional arthroscopic systems. Additionally, the ability to load instrument shafts with tool tips that are larger or otherwise configured in a manner that inhibit passing through a cannula inner diameter, expands the tool options available to the surgeon. Adding articulation capabilities to the cannula would even further improve surgical access and visualization especially when combined with the other features of the disclosed system.

Just distal to segment 191 is a segment of instrument shaft containing a small circumferential central groove 192. This groove is embedded into the contour of the outer instrument shaft component 110. FIG. 11 highlights a removable instrument shaft locking key 150. The key is shown prior to engagement with the instrument shaft and bilateral endoscope handle lever extensions 171. The locking key interacts with the instrument shaft, suction/irrigation harness, endoscope handle, and handle lever extensions in a manner that secures all items into position along the back end of the endoscope handle. The locking key 150 has front 195 and back 198 sections connected by a semi-flexible bridge 194 and separated by a slot 196. This bridge 194 acts as a tension hinge to allow the front and back components of the locking key to spread apart from one another. When the locking key is fully engaged, lever extensions 171 project into gaps 197 within the lower sides of the locking key.

When the instrument lever 175 is squeezed against the endoscope handle 170, the superior most aspect of the lever extensions rotate counterclockwise along the pivot point thereby displacing the back section of the locking key 150 away from the front section 195. In this implementation, the front section 195 of the locking key 150 is fixed into position against the irrigation/suction harness, outer instrument shaft, and endoscope handle while the back section of the locking key only engages the proximal shaft extension 191. Counterclockwise movement of the back segment of the locking key causes the inner instrument shaft to move posteriorly in relation to the outer instrument shaft thus activating the distal tool tip mechanism.

FIGS. 14-32 illustrate an optical cannula system 500. The optical cannula system 500 can include the structures and functionalities as the optical cannula system 100 as shown and described in relation to FIGS. 1-13 with the differences noted below. The optical cannula system 500 can include an endoscope 600 and a surgical tool assembly 700. The endoscope 600 can provide physical access to a surgical site for the surgical tool assembly 700, visual images, irrigation, suction and/or other surgical functionalities. The surgical tool assembly 700 can be insertable and removable from the endoscope 600. Although illustrated as a pair of grippers, the tool assembly 700 can include any of a variety of different surgical tools. Alternatively, the tool assembly 700 includes cutting tools, debriding tools, grasping tools, grinding tools, cauterizing tools, drilling tools, tissue sampling tools or other types of surgical tools. For example, any and/or all of the implementations and/or features of the tools and instruments described and/or illustrated in U.S. patent application Ser. No. 18/210,590, filed Jun. 15, 2023, titled SINGLE PORTAL, SURGICAL APPARATUS, such as the surgical microdebriders, can be utilized with the optical cannula systems and/or endoscopes described and/or illustrated herein. The entire contents of U.S. patent application Ser. No. 18/210,590 are hereby incorporated by reference in its entirety.

The endoscope 600 can include a body 670, a cannula 620, a rotation mechanism or assembly 660, an entry hub 683, an electrical cable 680, a first tube 681, and/or a second tube 682. The body 670 can include a distal end 671 and proximal end 672. The proximal end 672 can include an aperture providing access through an outer wall into an interior 673. The body 670 be generally cylindrically shaped between the distal end 671 and the proximal end 672. The distal end 671 can be tapered toward the cannula 620. The body 670 can include the entry hub 683. The electrical cable 680, the first tube 681 and/or the second tube 682 can enter into the body 670 through the entry hub 683. The electrical cable 680, the first tube 681 and/or the second tube 682 can extend outwardly in a parallel manner to prevent excessive interference or tangling when the endoscope 600 is in use. The electrical cable 680 can be removably connected or permanently connected with the entry hub 683. The electrical cable 680 can be removably connected or permanently connected with the entry hub 683. In disposable handle implementations, it might be simpler to have the electrical cable 680 permanently attached to the endoscope 600 so as to eliminate the need to stock separate cables. Having the electrical cable 680 configured to be removably connected to the entry hub 683, such as in the endoscope 600' of FIGS. 42A and 42B can provide advantages, such as facilitating transportation and sterilization of the handle 670' with the cable 680 detached as well as allowing the endoscope 600 to be independently maneuverable before connecting the electrical cable 680. Additionally, in disposable implementations, the removable electrical cable 680 can be a reusable component for use with multiple different endoscopes 600, minimizing the waste produced by the endoscope 600.

The cannula 620 can include a distal end 621 and a proximal end 622. The cannula 620 can extend along an axis between the distal end 621 and the proximal end 622. The cannula 620 can have an outer wall that extends from the distal end 621 to the proximal end 622. The outer wall can have a cross-sectional shape extending from the distal end 621 to the proximal end 622. The cannula 620 can include a first channel 623. The first (working) channel 623 can extend from the proximal end 622 to the distal end 621. The cannula 620 can include a second channel 624. The second channel 624 can extend from the proximal end 622 to the distal end 621. An inner wall 629 can separate the first channel 623 from the second channel 624. The inner wall 629 can extend from the proximal end 622 to the distal end 621. The first and second channels 623, 624 can have substantially the same cross-sectional shapes from the proximal end 622 to the distal end 621 (e.g., the cross-sectional shapes of both the first channel 623 and the second channel 624 can be independently consistent along the lengths of the channels). The second channel 624 may include a cutout section 625. The cutout section 625 can extend along a portion of the proximal end 622 (e.g., within the body 670). The cannula 620 can comprise a metal alloy, medical grade polymer, or other material. In certain examples, the cannula 620 can comprise a polyether ether ketone (PEEK), liquid crystal polymer (LCP) material, carbon-reinforced nylon, glass-reinforced nylon, or other composite material. The cannula 620 can comprise a unitary structure of a single material.

The cannula 620 can include a first port 626. The first port 626 can be through an outer wall of the cannula 620. The first port 626 can be in communication with the first channel 623. A second port 627 can be spaced from the first port 626. The second port 627 can extend through the outer wall of the cannula 620. The second port 627 can be in communication with the first channel 623. The first and second ports 626, 627 can extend through both sides of the outer wall of the cannula 620. Alternatively, the first and second ports 626, 627 can each extend through one side of the outer wall of the cannula 620, which can be on opposite sides of the first channel 623 (e.g., the first port 626 can be located on a first side of the outer wall and the second port 627 can be located on the opposite side of the outer wall). In another alternative the first and/or second ports 626, 627 can be in communication with the second channel 624. The first and second ports 626, 627 can each extend through one side of the outer wall of the cannula 620, which can be on opposite sides of the second channel 624. In another alternative, the first port 626 is in communication with the first channel 623 and the second port 627 is in communication with the second channel 624.

The proximal end 622 of the cannula 620 can be received within the interior 673 of the body 670 through the distal end 671 of the body 670. The distal end 621 of the cannula 620 can protrude from the distal end 671 of the body 670. The cutout section 625 can be within the body 670. The distal end 671 of the body 670 can include an aperture for receiving the cannula 620.

Figure 20:
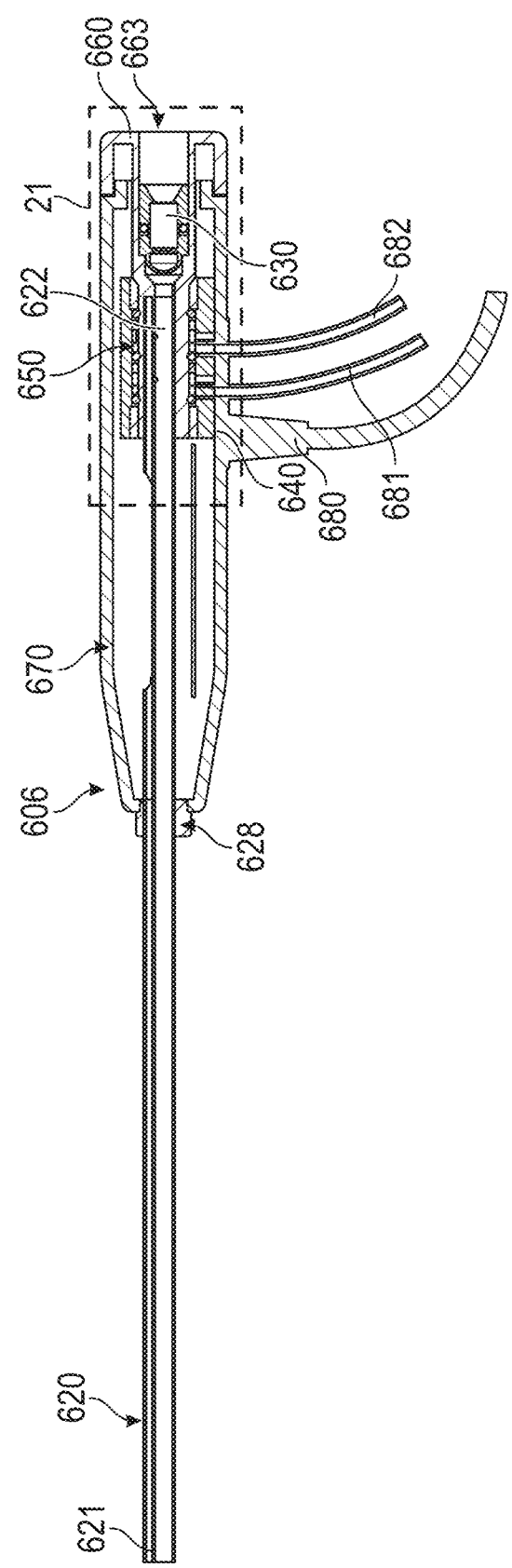
FIG. 20 shows a section view taken on the line 20-20 in FIG. 18, in accordance with implementations of the disclosure.

As shown in at least FIG. 20, the endoscope 600 can include a forward seal 628. The forward seal 628 can be formed of an elastic material. Forward seal 628 can include a central aperture. The central aperture of the forward seal 628 can be sized to receive the cannula 620 and seal against the outer wall thereof. The forward seal 628 can include a portion that is at least partially received within the distal end 671 of the body 670. The forward seal 628 can provide a liquid-tight seal between the cannula 620 and an inner wall of the central aperture of the forward seal 628 and between the portion and the distal end 671 of the body 670.

Referring back to FIGS. 16 and 17, the rotation assembly 660 can include a rotation handle 662, an insertion portion 661, and/or an aperture 663. In the illustrated example, the rotation handle 662 is configured as a dial portion 662 having a circumferential outer perimeter. The dial portion 662 can have a diameter similar to or greater than a diameter of the body 670 at the proximal end 672. The insertion portion 661 can be cylindrical in shape. The insertion portion 661 can extend in a distal direction from the dial portion 662. A distal end of the insertion portion 661 can have a reduced diameter relative to a proximal portion of the insertion portion 661. An aperture 663 can extend through the dial portion 662 and the insertion portion 661. Accordingly, the aperture 663 may be referred to herein as the "channel 663". The aperture 663 can include an inner wall sized to receive the proximal end 622 of the cannula 620.

The insertion portion 661 can include a first aperture 664 and a second aperture 665 spaced from the first aperture 664. The first and second apertures 664, 665 can extend through the outer wall of the insertion portion 661 to provide communication within the aperture 663.

The rotation assembly 660 can be assembled with the body 670. The rotation assembly 660 can be assembled with the proximal portion 672 of the body 670. The insertion portion 661 can be inserted within the interior space 673. The dial 662 can abut the proximal end 672. The rotation assembly 660 can be rotatable relative to the body 670, similar to the dial 160 of the system 100. The proximal end 622 of the cannula 620 can be received within the insertion portion 661. The proximal end 622 of the cannula 620 can be rotationally fixed with the insertion portion 661 such that rotation of the dial 662 rotates the cannula 620. The apertures 664, 665 can align with and/or be in communication with the ports 626, 627 of the cannula 620, respectively. As explained herein, such an arrangement can provide a benefit of allowing the cannula 620 to maintain fluid communication with the tubes 681, 682 while being rotated and at various rotational positions.

Figure 21:
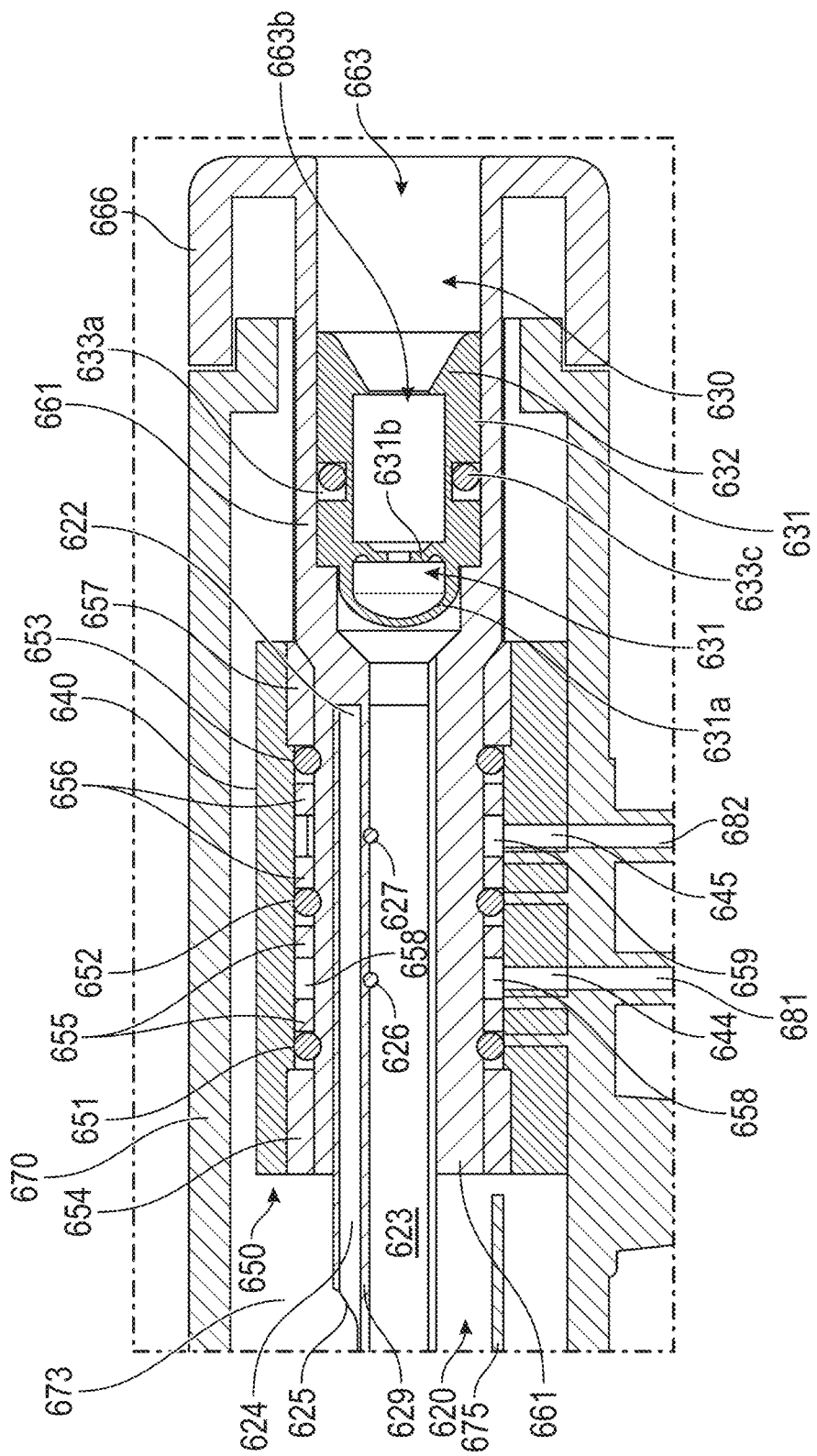
FIG. 21 shows a detail of FIG. 20, in accordance with implementations of the disclosure.
Figure 32:
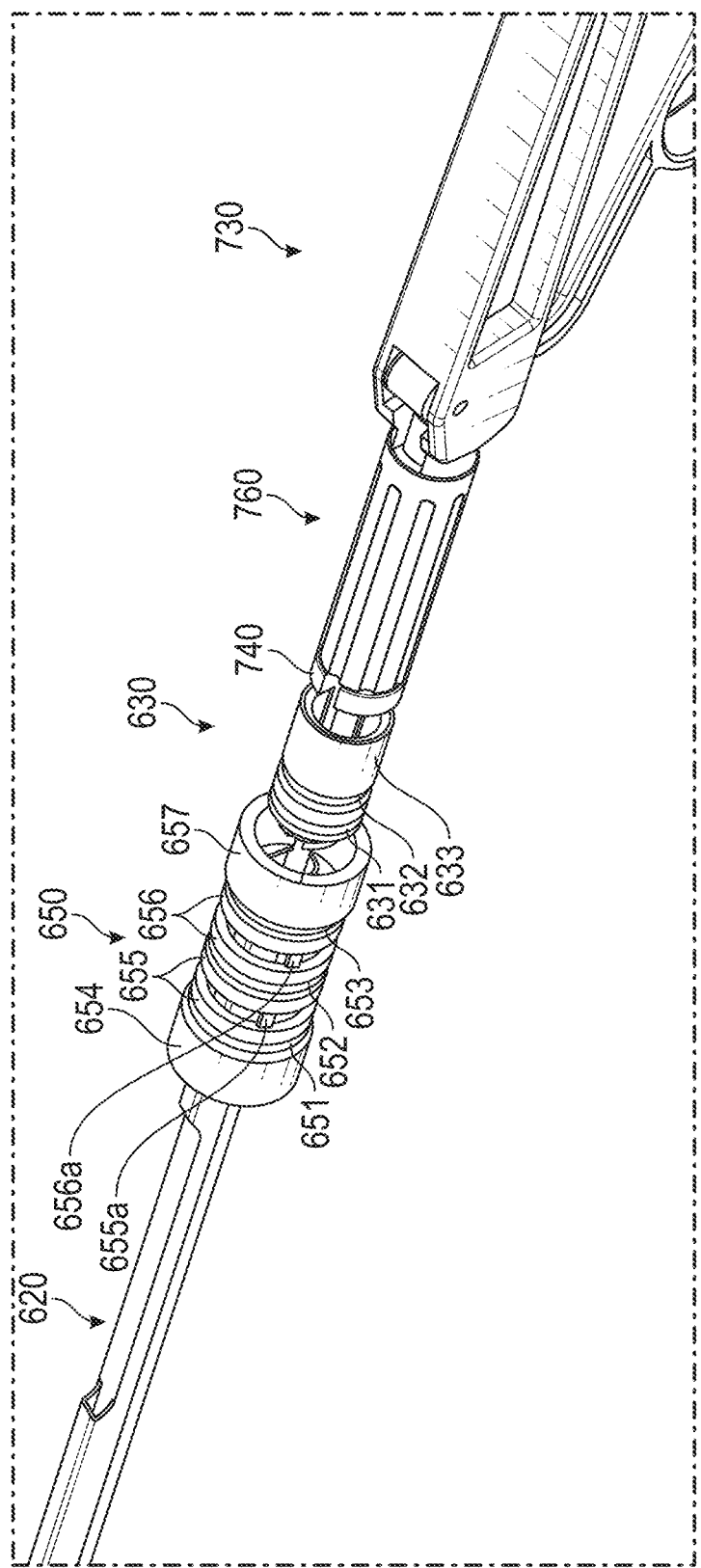
FIG. 32 shows the optical cannula system of FIG. 14 with the body, a harness block, and a rotation member of the endoscope removed for clarity, in accordance with implementations of the disclosure.

Referring now to FIG. 21, the endoscope 600 can include a harness assembly 650. The harness assembly 650 can provide communication between the tubes 681, 682 and the cannula 620, including when rotated. The harness assembly 650 can include a plurality of spacers and seals that are configured to create one or more circumferential pathways for providing irrigation and/or suction to the cannula 620 (e.g., through the respective first and second ports 626, 627 as will be discussed further below). The harness assembly 650 can include first, second, and/or third seals 651, 652, 653. The seals 651-653 can be in the form of O-rings. The harness assembly 650 can include a first spacer 654, a second spacer 655, a third spacer 656, and/or a fourth spacer 657. The first and fourth spacers 654, 657 can be cylindrical in shape. The second and third spacers 655, 656 can include dual rings that are spaced apart by extension members 655*a*, 656*a* (FIG. 32). Circumferential fluid pathways 658, 659 (FIG. 21) can be located between the dual rings created by the extension bars. A central aperture or channel can extend through the harness assembly. The central channel can extend through the first, second, and third seals 651, 652, 653 and the first, second, third, and fourth spacers 654, 655, 656, 657.

Figure 17:
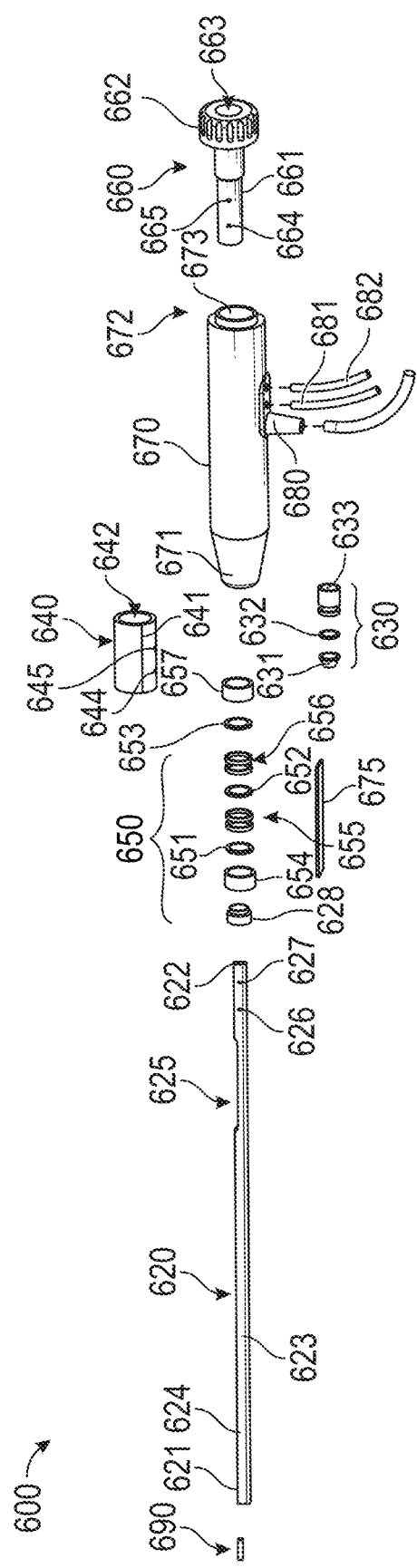
FIG. 17 shows an exploded view of the endoscope of FIG. 16, in accordance with implementations of the disclosure.
Figure 19:
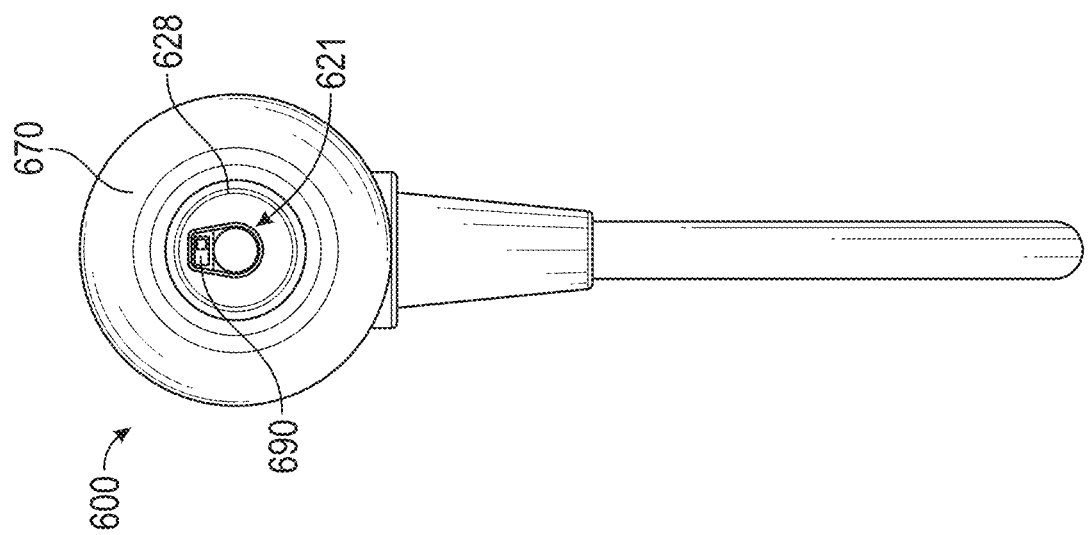
FIG. 19 shows a front view of the endoscope of FIG. 16, in accordance with implementations of the disclosure.
Figure 18:
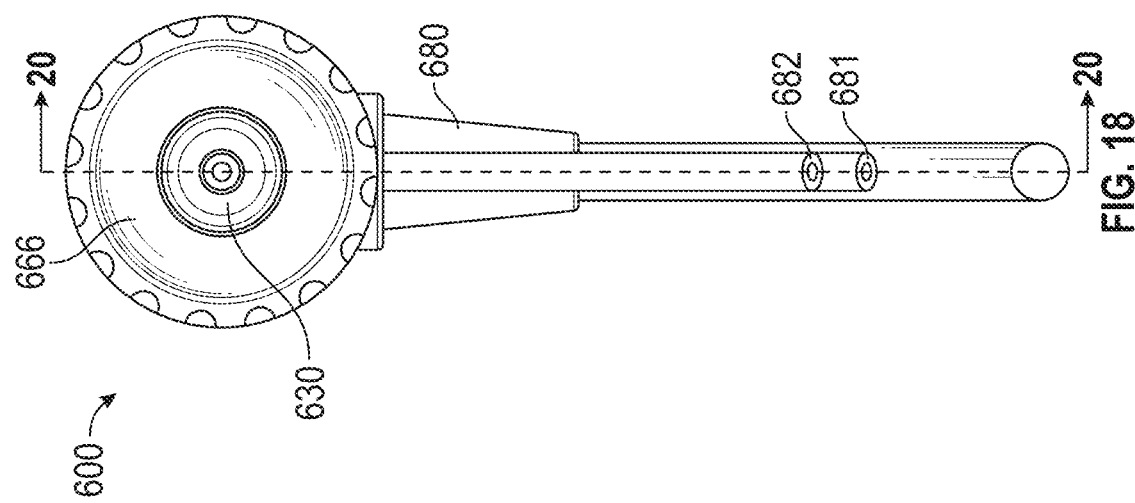
FIG. 18 shows a rear view of the endoscope of FIG. 16, in accordance with implementations of the disclosure.

The endoscope 600 can include a harness block 640, shown at least in the exploded view of FIG. 17. The harness block 640 can fit around the harness assembly 650 to form the circumferential pathways 658, 659. The harness block 640 can include a central aperture or channel 642. The central channel 642 can have an inner diameter and inner surface. The harness assembly 650 can be assembled within the central channel 642. The seals 651, 652, 653 can engage with the inner surface of the central channel 642. The harness block 640 can include a tab portion 641. The tab portion 641 can be located on one side of the harness block 640 to provide a noncylindrical cross-sectional shape thereto (i.e., to prevent rotation within the body 670). A first aperture (also referred to herein as the "first harness port") 644 can extend through an outer wall of the harness block 640 and provide fluid communication with the central channel 642. A second aperture (also referred to herein as the "second harness port") 645 can be spaced from the first aperture 644 and extend through the outer wall and provide fluid communication with the central channel 642.

With continued reference to FIG. 17, the endoscope 600 can include a tool seal 630. The tool seal 630 can be configured to engage and seal against a shaft of a tool. Accordingly, the tool seal 630 may also be referred to herein at a "shaft seal 630". The tool seal 630 can include a first seal 631. The first seal 631 can include flaps or slits that can pass a shaft of a tool (e.g., the shaft 710 of tool assembly 700 of FIGS. 24-27) therethrough. The tool seal can include a seal body 633. The seal body 633 can be a cylindrically shaped member with an aperture therethrough (e.g., sized to receive the tool shaft 710). The seal body 633 can include a circumferential recess 633*a*. The recess 633*a* can be sized to fit an O-ring 632. The O-ring 632 can be assembled within the recess 633*a*. A proximal end of the seal body 633 can include a tapered recess opening. In some implementations, the tool seal 630 may be configured to be reversible.

Figure 22:
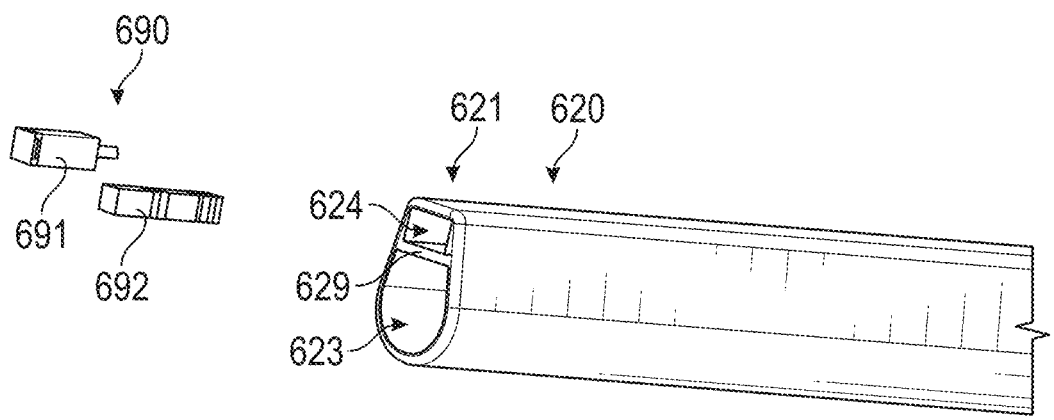
FIG. 22 shows a distal tip of a cannula of the endoscope of FIG. 16, in accordance with implementations of the disclosure.

As shown at least in FIG. 22, the endoscope 600 can include a camera assembly 690. The camera assembly 690 may include a camera chip like the camera chip 200 and/or additional camera chips. The camera assembly 690 can include a light source (e.g., LED or fiberoptic filament). The camera assembly 690 can be assembled within the distal tip 621 of the cannula 620, such as within the second channel 624. A signal wire (not shown) can extend along the second channel 624 between the distal end 621 and the cutout section 625 within the second channel 624. The wire can be attached with an electronic controller (PCB board) 675 within the body 670 (or otherwise connect with the electrical cable 680). The controller 675 can include image processing capabilities and/or other functions. The connection between the signal wire and the electronic controller board 675 can be through a service loop, electrical commutator, or other means.

FIGS. 21-22 show the internal assembly of the endoscope 600. The harness block 640 can be assembled within the interior space 673. The tab 641 can engage an inner surface of the body 670 to prevent rotation of the harness block within the body 670. The harness assembly 650 can be assembled within the interior space or aperture 642 of the harness block 640. The interior space 673 can be shaped such that the harness block 640 is in a fixed position (i.e., rotationally) within the interior space 673 such that the harness block 640 is fixed to the body 670. The first aperture 644 can be aligned with and in fluid communication with the first tube 681 through an outer wall of the body 670. The second aperture 645 can be aligned with and in fluid communication with the second tube 682 through the outer wall of the body 670.

The harness assembly 650 is assembled within the central channel 642 of the harness block 640. The first seal 651 can be located between the first spacer 654 and the second spacer 655. The second seal 652 can be located between the second spacer 655 and the third spacer 656. The third seal can be located between the third spacer 656 and the fourth spacer 657. First spacer 654 can be located on a distal end of the harness assembly 650. The fourth spacer 657 can be located on a proximal end of the harness assembly 650. The second spacer member 655 can form a circumferential fluid pathway 658. The third spacer 656 can form a circumferential fluid pathway 659. The seals 651, 652, 653 can contact the inner surface of the harness block 640 to isolate the pathways 658, 659 from each other. The circumferential pathways 658, 659 can align with and/or be in fluid communication with the respective apertures 644, 645 of the harness block 640. Thereby the circumferential pathways 658, 659 can align with and/or be in fluid communication with the respective tubes 681, 682.

The rotation assembly 660 can be assembled with the body 670. The insertion portion 661 of the rotation assembly 660 can be inserted into the central passage of the harness assembly 650 through the proximal end 672. The seals 651, 652, 653 can contact the outer surface of the insertion portion 661 to isolate the pathways 658, 659 from each other. The first and second apertures (ports) 664, 665 can align with and be in fluid communication with the respective circumferential pathways 658, 659.

The proximal end 622 and the cannula 620 can be received within the interior space 673 such as through the distal end 671 of the body 670. The proximal end 622 can be received within the insertion portion 661 of the rotation assembly 660. The aperture 664 of the rotation assembly 660 can be aligned with and/or in fluid communication with the first port 626 of the cannula 620. Accordingly, the first tube 681, aperture 644, circumferential pathway 658, aperture 664, and port 626 can be in fluid communication. The aperture 665 of the rotation assembly 660 can be aligned with and/or in fluid communication with the second port 627 of the cannula 620. Accordingly, the second tube 682, aperture 645, circumferential pathway 659, aperture 665, and port 627 can be in fluid communication.

The insertion portion 661 of the rotation assembly 660 can be rotatable along a longitudinal axis thereof (e.g., by rotating the dial 662). The cannula 620 can be locked into rotation with the rotation assembly 660. The rotation assembly 660 can rotate relative to the harness assembly 650, the harness block 640, and/or the body 670. Rotation of the insertion portion 661 within the harness assembly 650 can maintain alignment and/or fluid communication between the ports 626, 627 of the cannula 620 and the tubes 681, 682 through the circumferential pathways 658, 659. Rotation of the insertion portion 661 within the harness assembly 650 can be at least 90° or 360° and optionally unlimited (e.g., for a commutator).

The tool seal 630 can be inserted into the insertion portion 661 through the aperture 663. The tool seal 630 can be a uni-directional seal. The tool seal 630 can be inserted into the aperture 663 through the proximal end of the rotation assembly 660. The tool seal 630 and aperture 663 can aligned with the first channel 623. The tool seal 630 (e.g., the O-ring 632) can seal against an inner surface of the aperture 663. A tapered portion of the insertion portion 661 can provide a seat for the tool seal 630. The tool seal 630 can be inserted into a proximal portion of the insertion portion 661. The first seal 631 can include a first seal member 631a and a second seal member 631b. The first seal member 631a can include a dome shape. The second seal member 631b can attach with the first seal member 631a. The first and/or second seal members 631a, 631b can include a central aperture or slit therethrough. Optionally, the tool seal 630 can be inserted in the reverse orientation as illustrated in FIG. 21 (e.g., to accommodate distal-to-proximal loading on an instrument shaft within the cannula). In an alternative embodiment, a rotatable or switchable lever can be included that couples with tool seal 630. The lever can switch between uni-directional seals (e.g., to accommodate distal-to-proximal loading on an instrument shaft within the cannula or differently sized seals) and/or provide an option for no seal at all depending on the instrument inserted into the handle.

Figure 23:
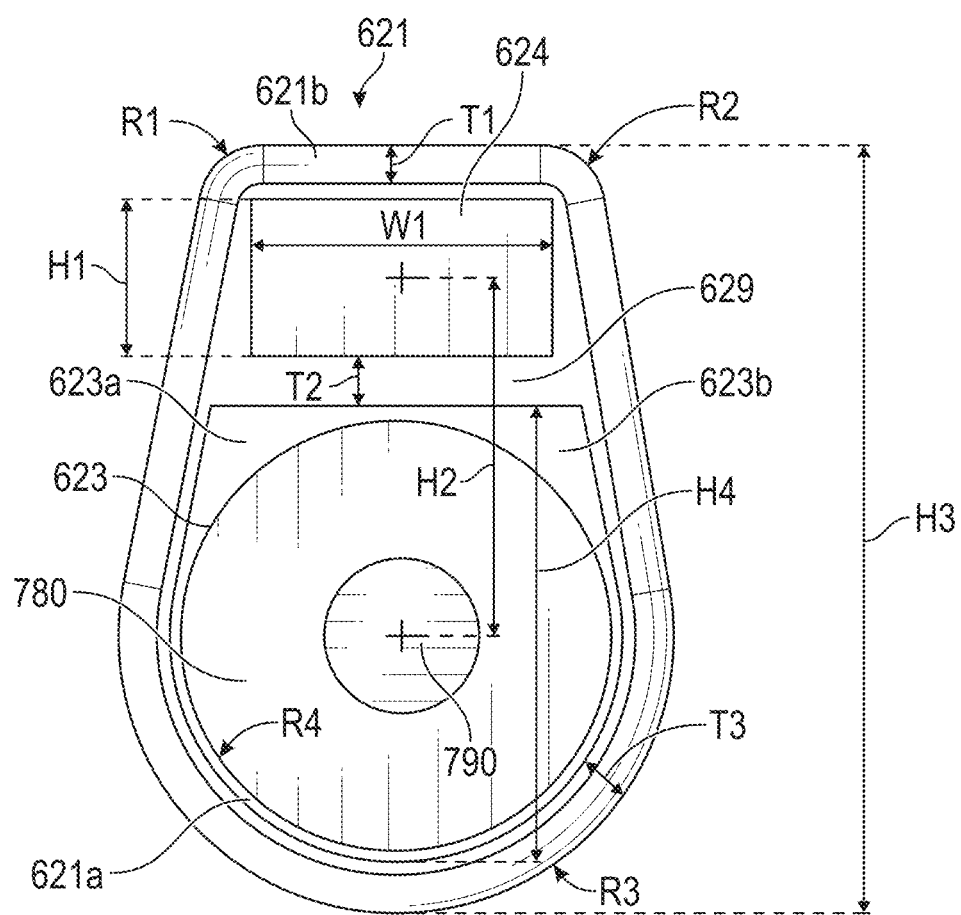
FIG. 23 shows a front view of the distal tip of a cannula of the endoscope of FIG. 16 including a shaft of the tool within a working channel, in accordance with implementations of the disclosure
Figure 24:
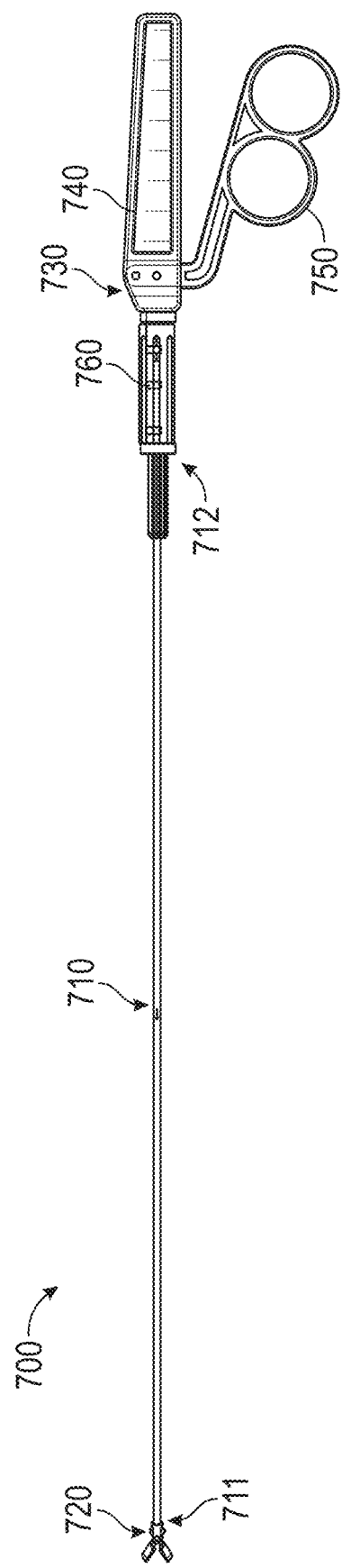
FIG. 24 shows a tool of the optical cannula system of FIG. 14, in accordance with implementations of the disclosure.
Figure 25:
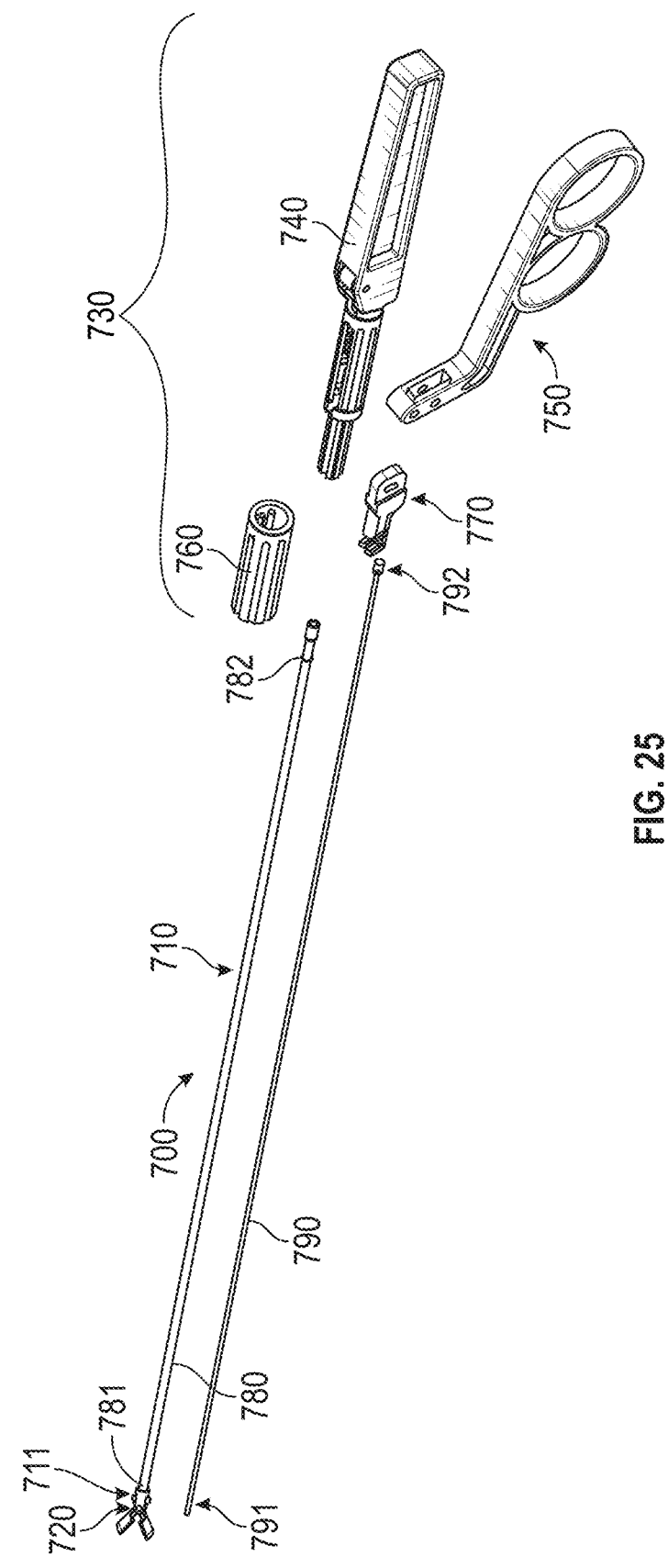
FIG. 25 shows an exploded view of the tool of FIG. 24, in accordance with implementations of the disclosure.
Figure 26:
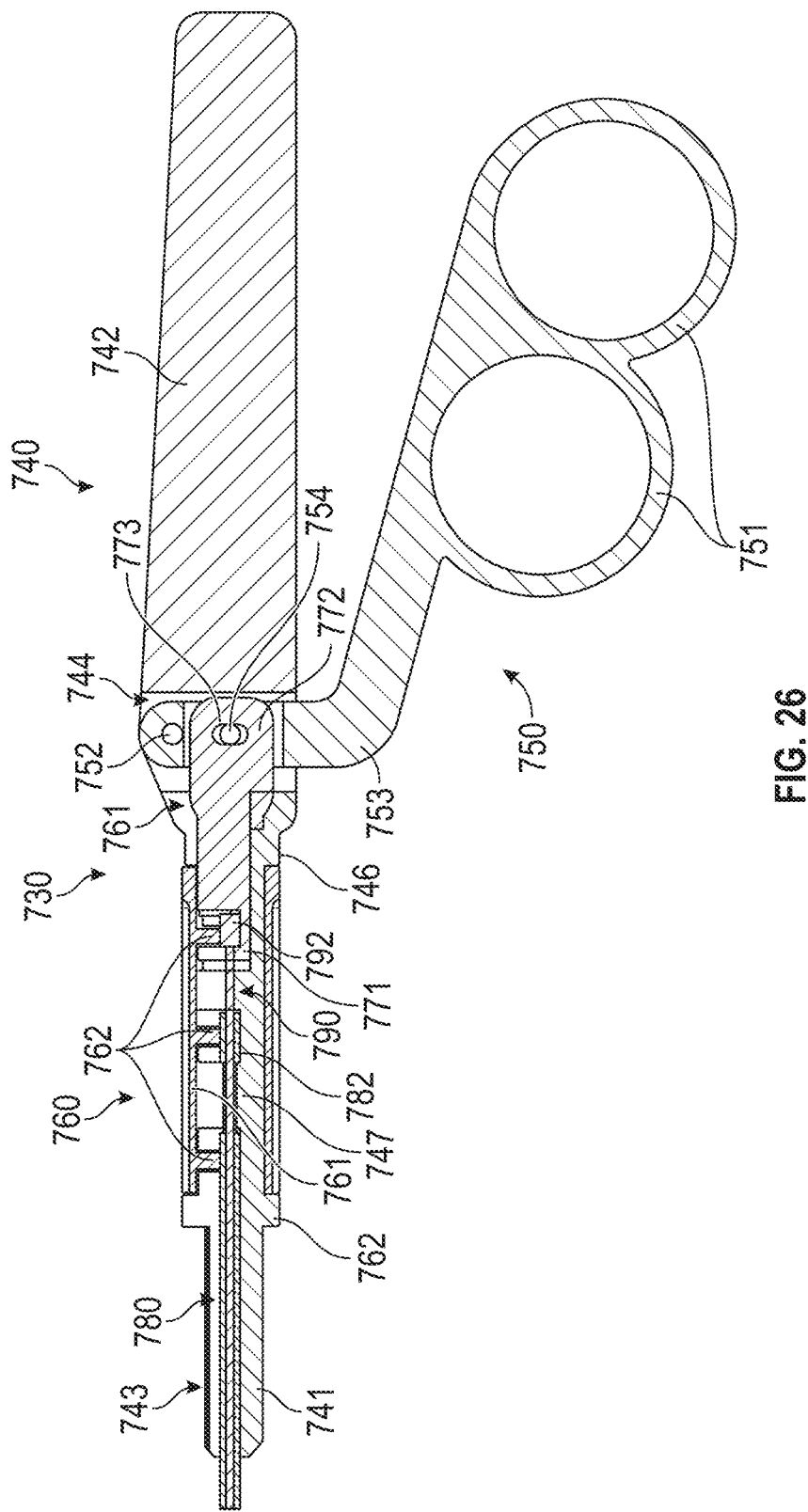
FIG. 26 shows a section view of a grip portion of the tool of FIG. 24, in accordance with implementations of the disclosure.

FIGS. 22-23 shows the distal end 621 of the cannula 620 including the first channel 623 and the second channel 624 that are within an interior space defined by an outer wall of the cannula 620. The outer wall of the cannula 620 can include a curved or circular lower portion 621a. The outer wall of the cannula 620 can include a flat or upper portion 621b. The curved portion 621a can be attached with the flat portion 621b on either side through curved or planar side portion. The first channel 623 can be located within the curved lower portion 621a. Additionally, the first channel 623 can include a first side portion 623a and a second side portion 623b. Optionally, the first and second side portions 623a, 623b can in use be at least partially separated. The first channel 623 can be sized to receive a shaft 710 of the tool assembly 700. The shaft 710 can include an outer shaft 780 and an inner shaft 790. As shown in FIG. 23, the outer shaft 780 and inner shaft 790 of the tool assembly 700 can be positioned within the first channel 623 of the cannula 620. The first channel 623 can be sized such that the shaft 710 generally fills the channel 623. Suction and irrigation can occur along the first and second side portion 623a, 623b or otherwise around the shaft 710. Optionally, the channel 623 and the shaft 710 can be sized such that shaft 710 separates the first side portion 623a from the second side portion 623b which can be located in upper opposite corners of the first channel 623. In one alternative, the first side portion 623a can be aligned with the first port 626 and the second side portion 623b can be aligned with the second port 627 such that irrigation can occur along the first side portion 623a and suction can occur independently along the second side portion 623b.

An inner wall 629 separates the first working channel 623 from the second channel 624. The inner wall 629 can extend from the proximal end 622 to the distal end 621. Alternatively, additional inner walls can be included to further divide the interior space of the cannula 620. The second channel 624 can have a rectangular or trapezoidal cross-sectional shape, in some implementations. The shape of the second channel 624 can be sized such that the camera assembly 690 fits within the distal end of the second channel 624. Alternatively additional camera chips or lights or other instruments can be fit within the second channel 624. The camera assembly 690 can include at least one camera chip 691 and at least one light source 692. The first channel 623 can have an arched cross-sectional shape with a circular portion and a flat portion, in some implementations. The outer wall of the cannula 620 can have a thickness T1 between the flat portion 621b and the second channel 624. The outer wall of the cannula 620 can have a first upper rounded edge R1 and a second upper rounded edge R2. A third curvature R3 can extend below the first channel 623. An inner portion of the outer wall within the first channel 623 can have a curvature R4. The second channel have a height H1 and/or a width W1. The inner wall 629 can have a thickness T2. The outer wall between the third curvature R3 and the fourth curvature R4 can have a thickness T3. The second channel 624 can be spaced from the first channel 623 by a height H2. The outer wall of the cannula 620 can have a height H3 (e.g., centerline-to-centerline). The first channel 623 can have a height H4. The chart below provides certain desirable values and ranges for the dimensions of the cannula 620. Alternatively, other cannula and channel dimensions are within the scope of the present disclosure.

|  | Dimension (mm) | Dimension Range (mm) |
| --- | --- | --- |
| R1/R2 | 0.5 | 0.1-3.0 |
| R3 | 4.4 | 2.5-8.0 |
| R4 | 3.6 | 2.0-7.0 |
| T1/T2/T3 | 0.4 | 0.1-4.0 |
| H1 | 1.3 | 0.5-4.0 |
| W1 | 2.4 | 0.5-8.0 |

-continued

|    | Dimension (mm) | Dimension Range (mm) |
|----|----------------|----------------------|
| H2 | 2.8            | 0.5-8.0              |
| H3 | 6.1            | 4.0-12.0             |
| H4 | 3.6            | 2.0-9.0              |

FIGS. 24-27 show the tool assembly 700 in further detail. The tool assembly 700 can include the shaft 710 with a tool 720 on a distal end 711 of the shaft 710. A proximal end 712 of the shaft 710 can be attached with a grip assembly 730. The grip assembly 730 can include a grip body 740, a lever 750 and/or an assembly sleeve 760.

The shaft 710 can include an outer shaft 780. The outer shaft 780 can include a distal end 781 and a proximal end 782. The distal end 781 can attach with the tool 720. The proximal end 782 can include a proximal portion including a shoulder that aids in assembly with the grip portion 730.

The shaft 710 can include an inner shaft 790. The inner shaft 790 can be a control mechanism for the tool 720. The inner shaft 790 can include a distal end 791. The distal end 791 can be connected with the tool 720 such as for actuating a pair of grippers. A proximal end 792 of the inner shaft 790 can be attached with the grip assembly 730 (e.g., the lever 750) for purposes of actuation.

The grip body 740 includes a distal portion 741 and a proximal portion 742. The distal portion 741 can include a general cylindrical shape with a slot 743 extending from the distal end proximally towards the proximal portion 742. The slot 743 can provide access for assembling the shaft 710 with the grip portion 730. The distal portion 741 can include a distal flange 745. The slot 743 can extend through the distal flange 745. A proximal flange 746 can be located proximal to the distal flange 745. The grip body 740 can include a slot 744 for receiving one end of the grip level 750. The distal portion 741 can include a shoulder or recess 747. The shoulder or recess 747 can engage with the shoulder of the proximal end 782 of the outer shaft 780. The shoulder or recess 747 can be aligned with the slot 743 or accessible therethrough.

The grip assembly 730 can additionally include a catch member 770. The catch member 770 can include a distal end with a catch 771. The catch 771 can be configured to engage the proximal end 792 of the inner shaft 790. The catch 771 can be aligned with the slot 743 or accessible therethrough. The catch member 770 can include a proximal end 772. The proximal end 772 can include a slot 773. The catch member 770 can be assembled within the grip body 740 and held in place by the assembly sleeve 760. The catch member 770 can be attached or connected with the lever 750 for providing actuation of the inner shaft 790. The proximal end of the inner shaft 790 can include a shoulder for attachment of the catch 771.

The lever 750 can include a grip portion 751 that may include one or more finger holes. The lever 750 can include a shaft portion 753 that includes a pivot 752. Pivot 752 can attach the lever 750 within the slot apertures 744. The lever 750 can be pivotally connected at the pivot 752. Alternatively, the lever 750 can be integrally formed with the grip body 740 (e.g., a living hinge). The lever 750 can include a pin 754. The pin 754 can engage within a slot 773 on a proximal end 772 of the catch member 770. The movement of the lever 750 can move the catch member 770 axially in line with the shaft 710.

Figure 27:
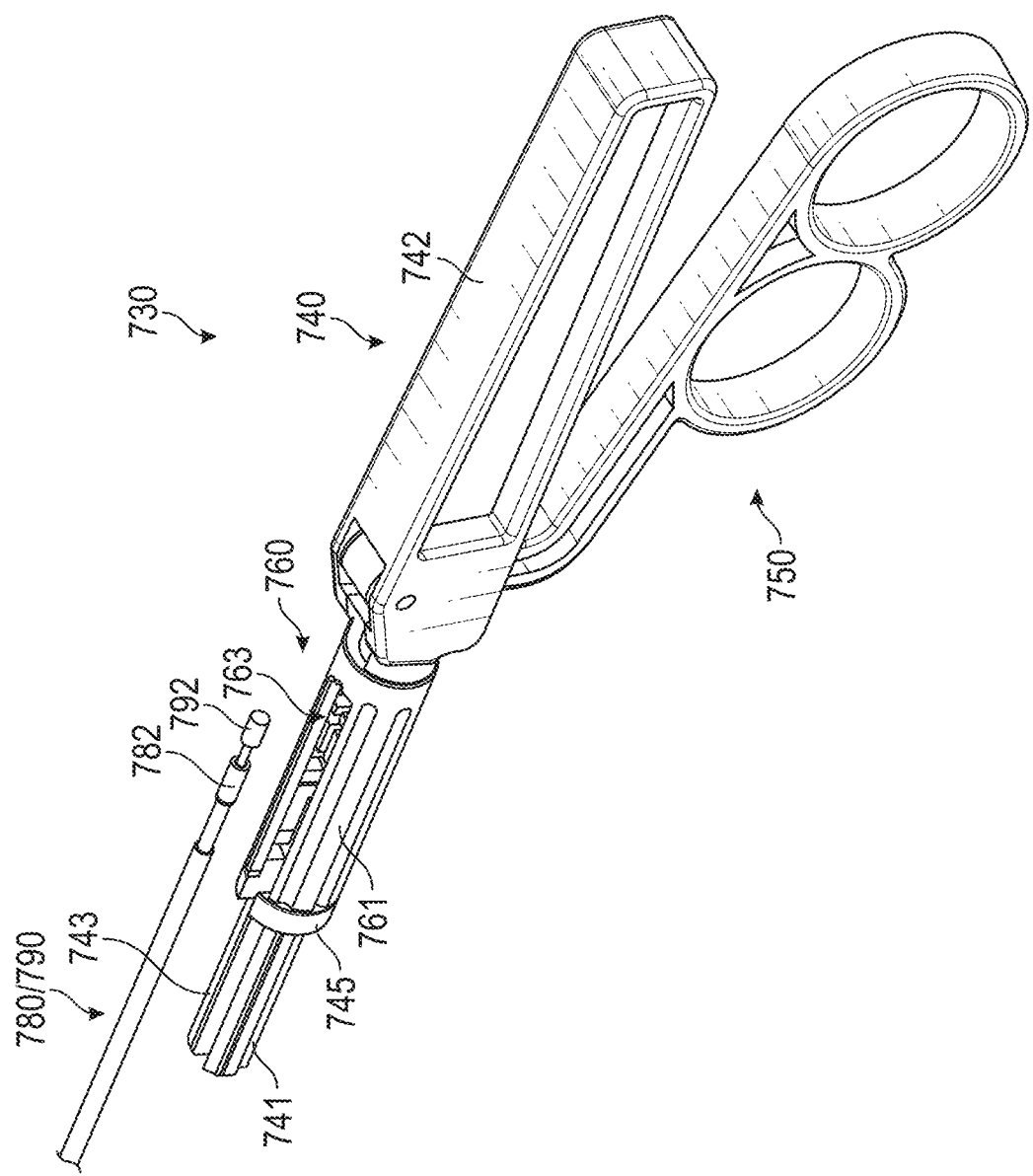
FIG. 27 shows the grip portion of the tool in an open configuration for assembling and disassembling a shaft of the tool, in accordance with implementations of the disclosure.

The assembly sleeve 760 can be assembled between the distal flange 745 and the proximal flange 746. The assembly sleeve 760 can be rotatable about the distal portion 741 of the grip body 740. The assembly sleeve 760 can be rotatable into and out of an assembly configuration in which a slot 763 of the assembly sleeve 760 aligns with the slot 743 on the grip body 740. The shafts 780, 790 can be assembled through the slot 743 when the slot 763 in the assembly configuration (FIG. 27). This arrangement can also provide for a quick assembly and disassembly configuration for the tool assembly 700. After the shafts 780, 790 have been inserted within the slot 743, the assembly sleeve 760 can be rotated to move the assembly slot 763 and cover the slot 743. This rotation can lock the proximal ends 782, 792 into place within the grip assembly 730.

Figure 28:
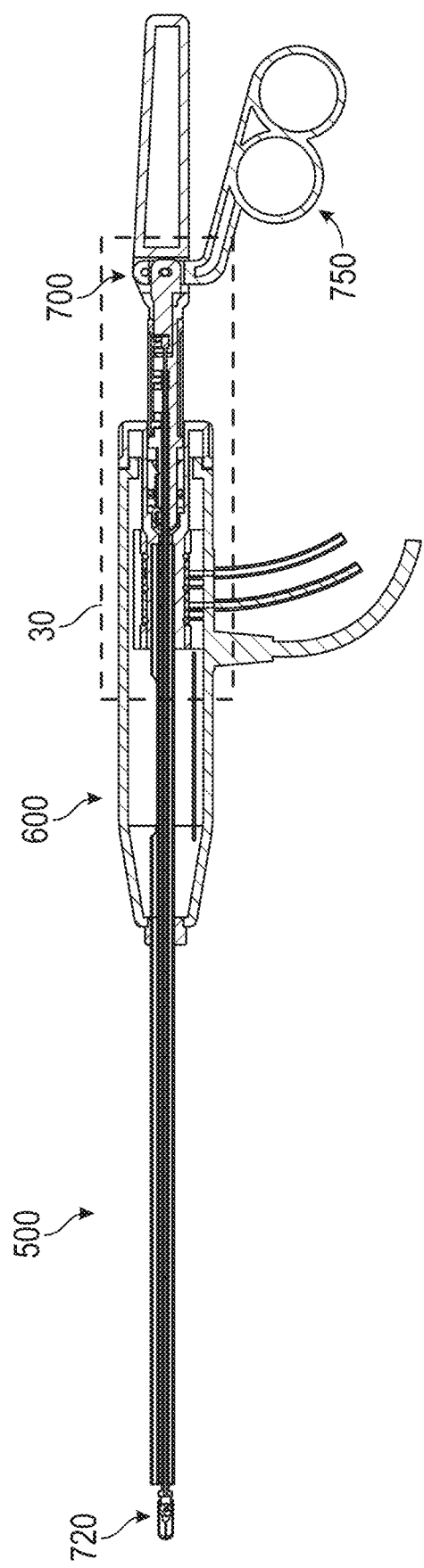
FIG. 28 shows a section view of optical cannula system of FIG. 14 in a first configuration, in accordance with implementations of the disclosure.
Figure 29:
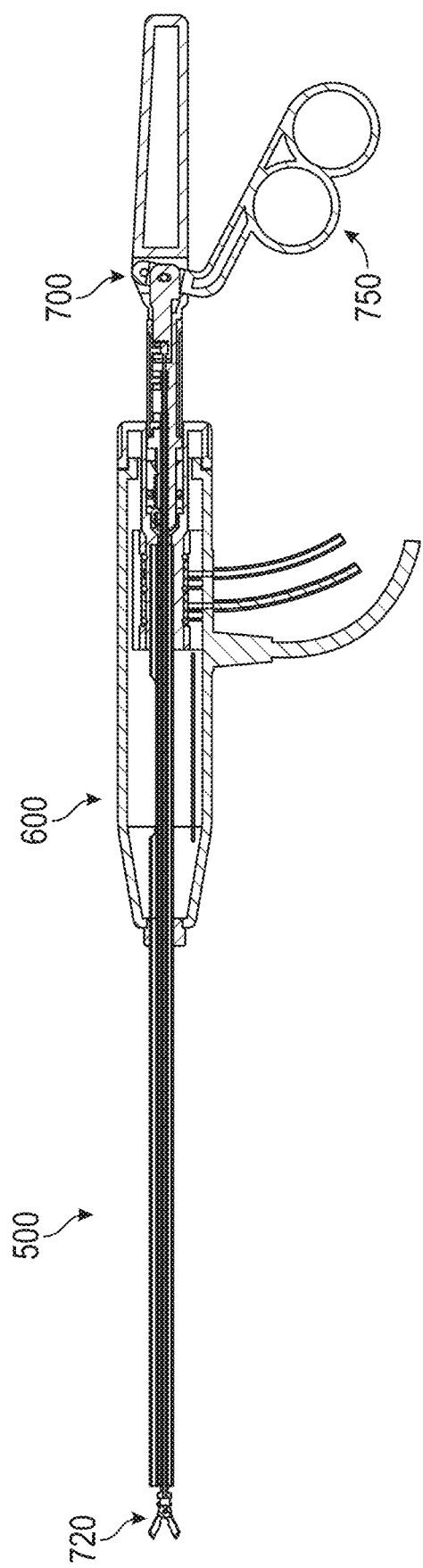
FIG. 29 shows a section view of optical cannula system of FIG. 14 in a second configuration, in accordance with implementations of the disclosure.
Figure 30:
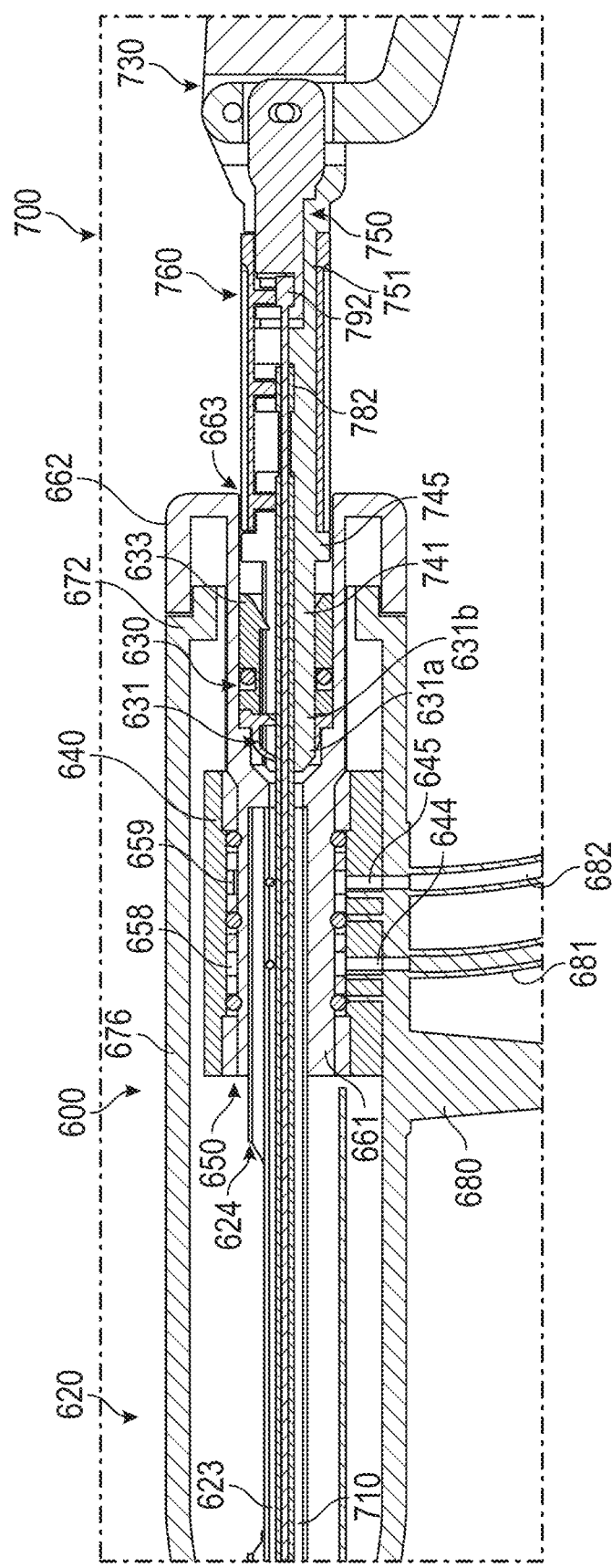
FIG. 30 shows a detail of FIG. 28, in accordance with implementations of the disclosure.
Figure 31:
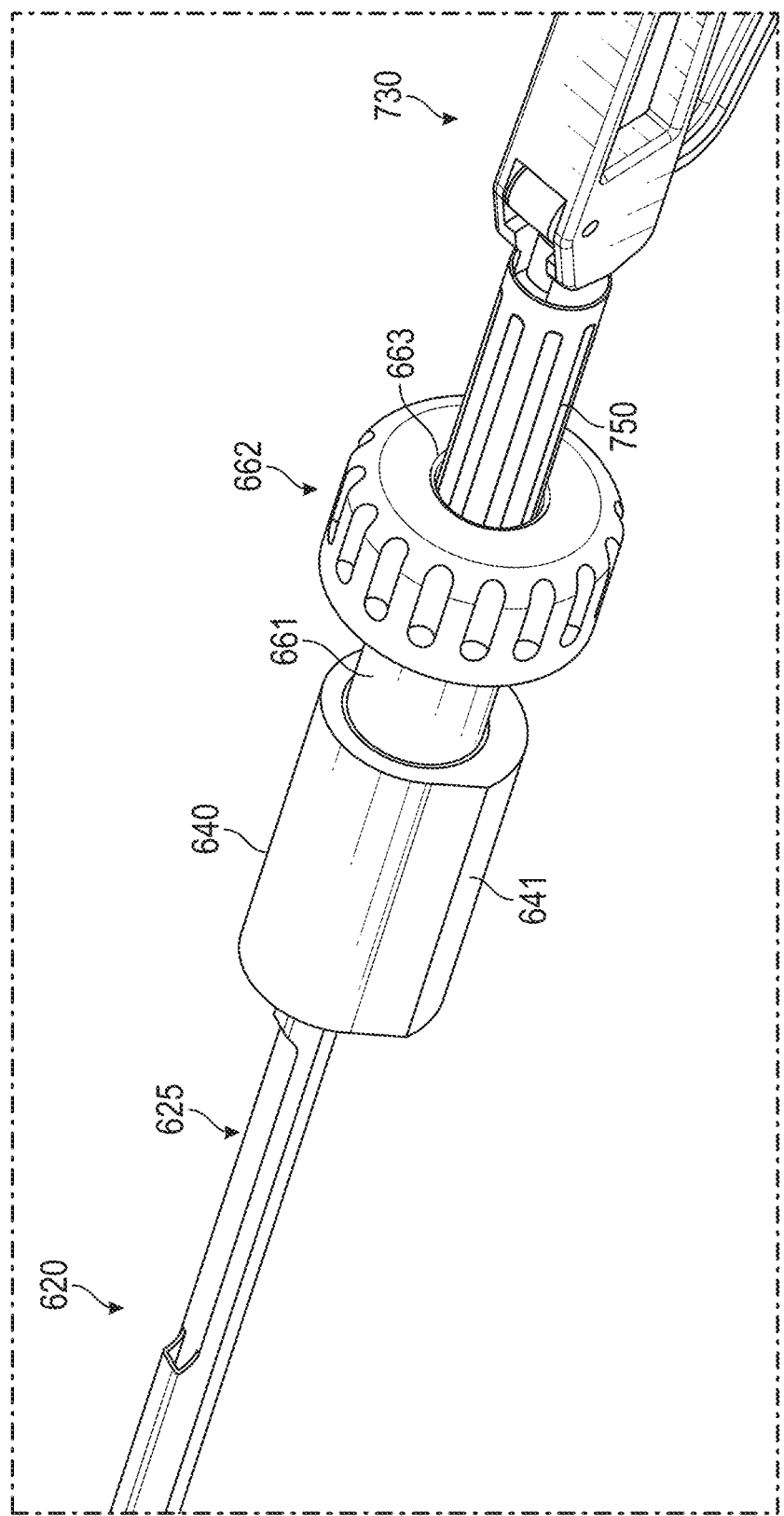
FIG. 31 shows the optical cannula system of FIG. 14 with a body of the endoscope removed for clarity, in accordance with implementations of the disclosure.

FIGS. 28-32 illustrates assembly the optical cannula system 500 with the tool assembly 700 received within the endoscope 600. FIG. 28 shows a first configuration with the jaws of the tool 720 and a first configuration (closed). FIG. 29 shows the tool 720 in a second configuration with the jaws of the tool 720 open. The lever 750 having been actuated to advance the catch member 770 and actuate the jaws through the shaft 790.

The shaft 710 is received within the cannula 620. When loaded proximally to distally, the shaft is inserted through the rotation assembly 660 (e.g., aperture 663) and into the first channel 623 of the cannula 620. The shaft 710 can be inserted through the tool seal 630. The seal member 631 of the tool seal 630 can seal against the passage of fluid back through the aperture 663. The first seal 631 can seal around the shaft 710. The first seal 631 can be positioned distally relative to the body 633.

When loaded distally-to-proximally, the tool assembly 700 can be at least partially disassembled. The shaft 710 is inserted within the proximal end 712 entering the distal end 621 of the cannula 620. The tool seal 630 can be removed from the aperture 663 and replaced in the reverse orientation. The proximal end 712 can be loaded into the rotation assembly 660 (e.g., aperture 663) from the first channel 623 of the cannula 620. The shaft 710 can be inserted through the tool seal 630. The seal member 631 of the tool seal 630 can seal against the passage of fluids back through the aperture 663. The first seal 631 can seal around the shaft 710. The first seal 631 can be positioned proximally relative to the body 633. The shaft 710 can then be reassembled with the grip assembly 730. Alternatively, to reverse the tool seal 630, a second seal in the reverse orientation can be installed within the aperture 663.

The distal portion 741 of the tool assembly 700 can be received at least partially within the aperture 663. The aperture 663 can include a length such that the distal portion 741 can be inserted to varying depths within the aperture 663 while still being engaged with the rotation assembly 660. In this manner, the tool portion 720 can be moved relative to the cannula 620 (e.g., the tool portion 720 can be extended and retracted relative to the distal end 621). Optionally, the distal portion 741 can be sized such that the tool assembly 700 can be rested within the rotation assembly 660. In this configuration, the tool assembly 700 can rotate with the rotation assembly 660. In this configuration, the surgeon can free one hand to attend to other tasks while the endoscope 600 and tool assembly 700 are held in the other hand. Otherwise, the tool assembly 700 can be rotated or otherwise moved independent of the cannula 620.

FIGS. 33-42B illustrate an optical cannula system 500' and components thereof. The optical cannula system 500' can include the same structures and functionalities as the optical cannula system 500 as shown and described in relation to FIGS. 14-32 with the differences noted below.

Thus, reference numerals used to designate various features or components of the optical cannula system 500 are identical to those used for identifying the corresponding features of the components of the optical cannula system 500', except that the numerical identifiers for the optical cannula system 500' include a "prime" symbol. The optical cannula system 500' can include an endoscope 600' and the tool assembly 700. The endoscope 600' can provide physical access to a surgical site for the surgical tool, visual images, irrigation, suction and/or other surgical functionalities. The tool assembly 700 can be insertable and removable from the endoscope 600' in a similar or identical manner as described with reference to the endoscope 600 of FIGS. 14-32.

Figure 33:
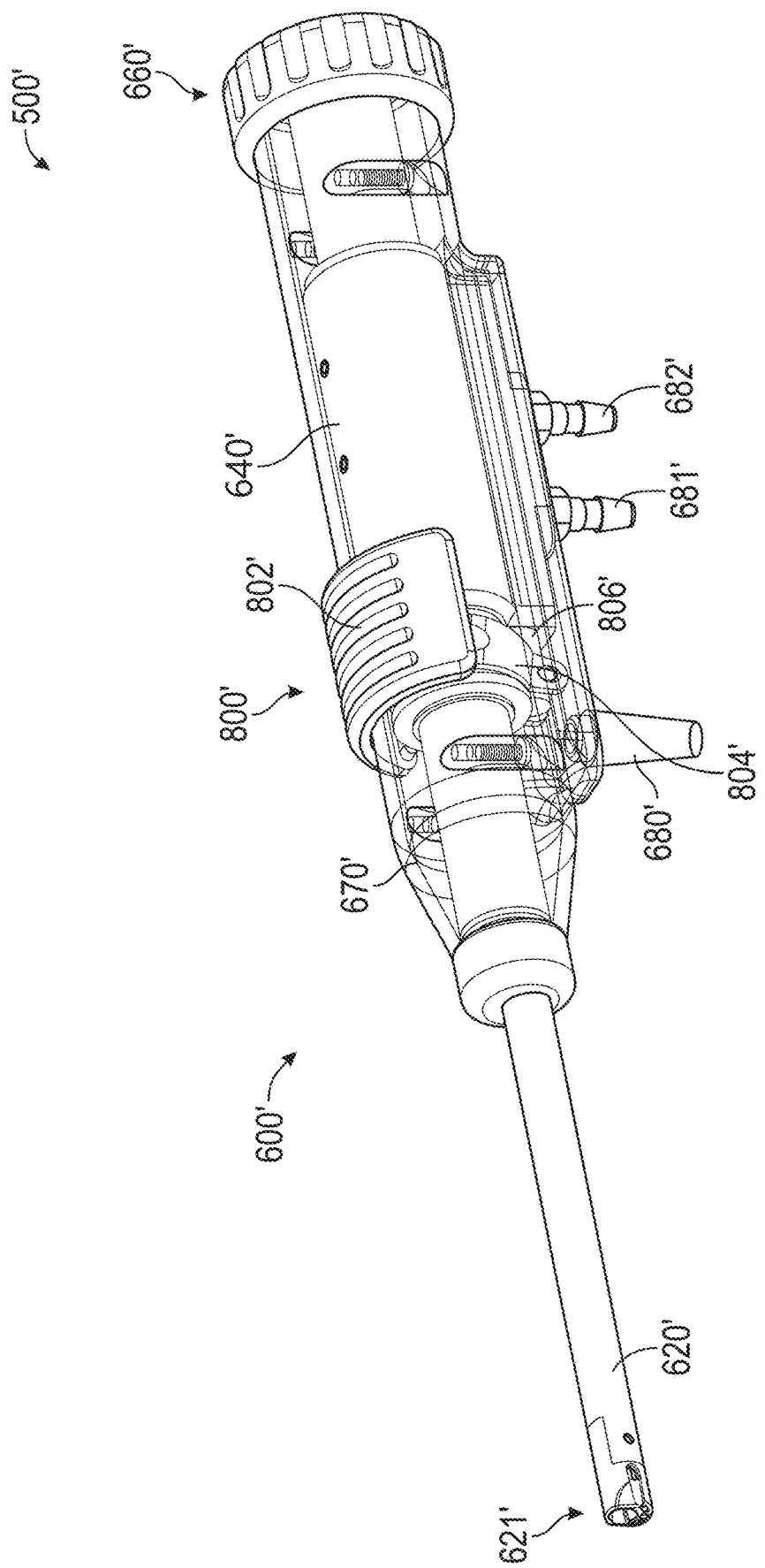
FIG. 33 illustrates an embodiment of an optical cannula system including an endoscope, in accordance with implementations of the disclosure.
Figure 34:
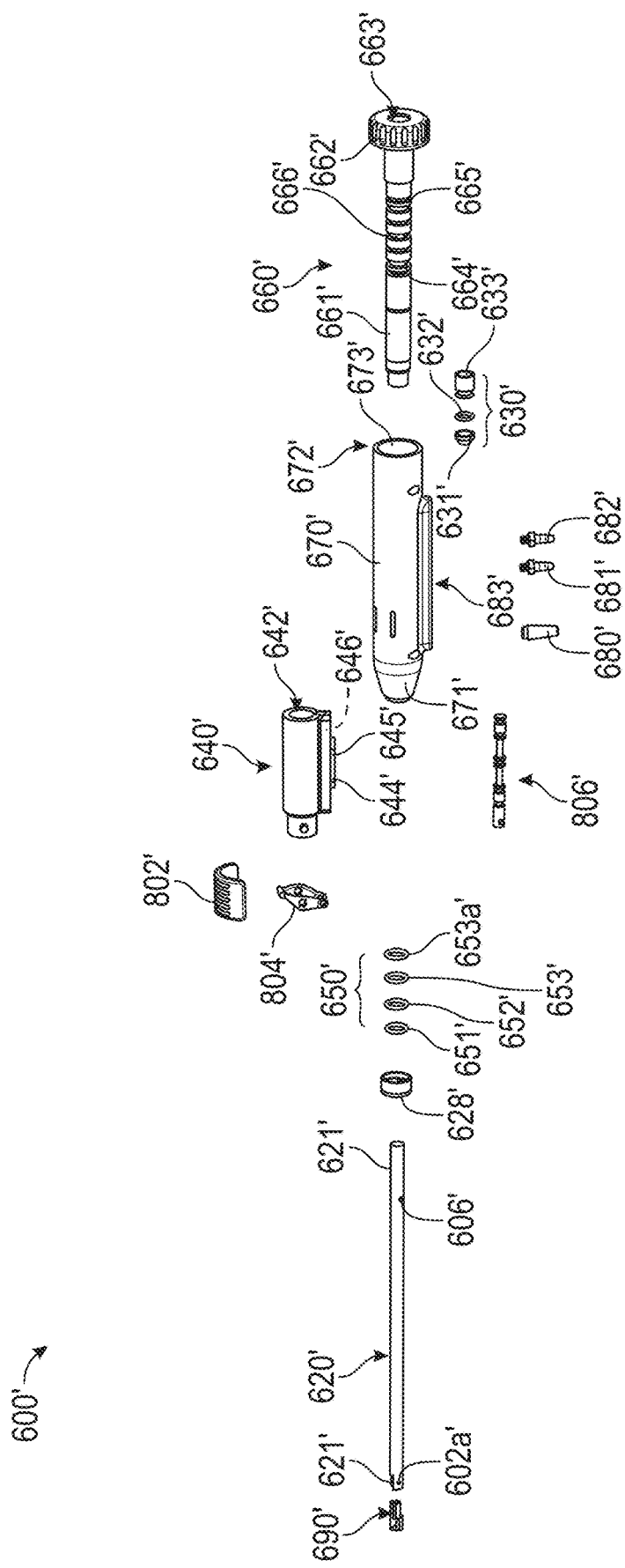
FIG. 34 shows an exploded view of the endoscope of FIG. 33, in accordance with implementations of the disclosure.

FIG. 33 illustrates a perspective view of the endoscope 600' and FIG. 34 illustrates an exploded view of the endoscope 600'. Like the endoscope 600 of at least FIG. 16, the endoscope 600' can include a handle or body 670', a cannula 620', a rotation assembly 660', an electrical cable 680', a first tube 681', and/or a second tube 682'. In FIG. 33, the body 670' is shown as transparent for illustrative purposes. The optical cannula system 500' differs from the optical cannula system 500 in that the optical cannula system 500' includes an alternative and/or additional channel (e.g., a third channel 601') in the cannula 620', and the endoscope 600' includes a valve assembly 800'. As such, various components of the optical cannula system 500' are modified to accommodate the valve assembly 800'. As explained herein, both the first channel 623' and the third channel 601' of the cannula 620' can be configured for both irrigation and suction. The valve assembly 800' can be used to alternate the function of both the first channel 623' and the third channel 601' between suction and irrigation selectively. For example, when the valve assembly 800' is in a first configuration, the third channel 601' can be configured for suction and the first channel 623' can be configured for simultaneous irrigation. When the valve assembly 800' is in a second configuration, the first channel 623' can be configured for suction and the third channel 601' can be configured for simultaneous irrigation. As explained herein, the operator can selectively transition between the first configuration and the second configuration while using the optical cannula system 500'.

As described further herein, the ability to alternate the suction and irrigation functions of the channels 601', 623' of the cannula 620' can provide certain advantages. For example, alternating between the suction and irrigation functions within the first working channel 623' can allow the operator to quickly and efficiently clear or unclog the first working channel 623' during a procedure. Additionally, selectively utilizing one channel (e.g., the first channel 623') for irrigation and the other channel (e.g., the third channel 601') for suction, or vice-versa, can allow the operator to control and direct the irrigation and suction of the optical cannula system 500' with greater precision, which is desirable. In another example, the channels 601', 623' can be different sizes (e.g., with different total cross-sectional areas), which can allow for different fluid pressures between the channels 601', 623'.

Figure 35A:
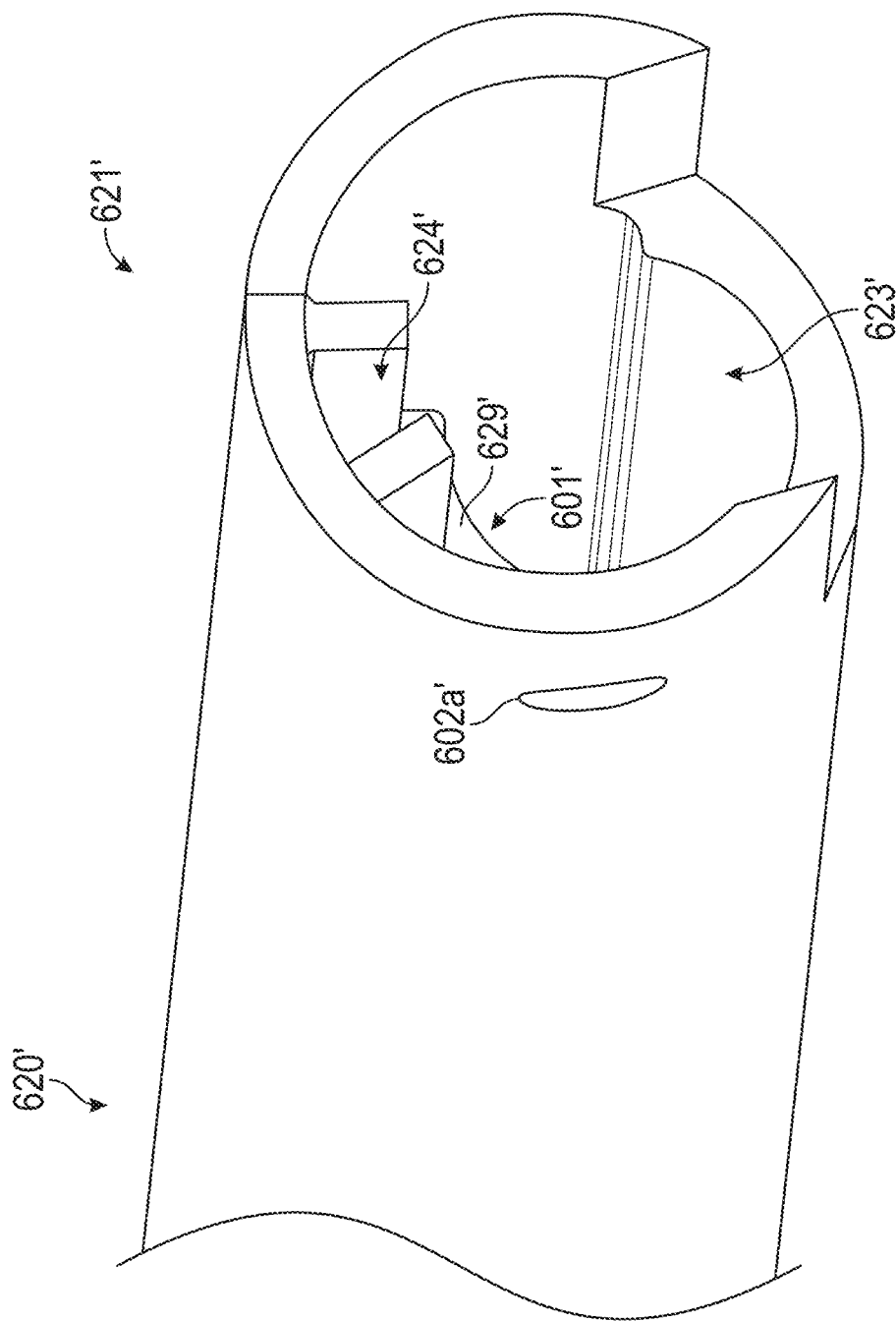
FIGS. 35A and 35B show a distal tip of a cannula of the endoscope of FIG. 33, in accordance with implementations of the disclosure.
Figure 35B:
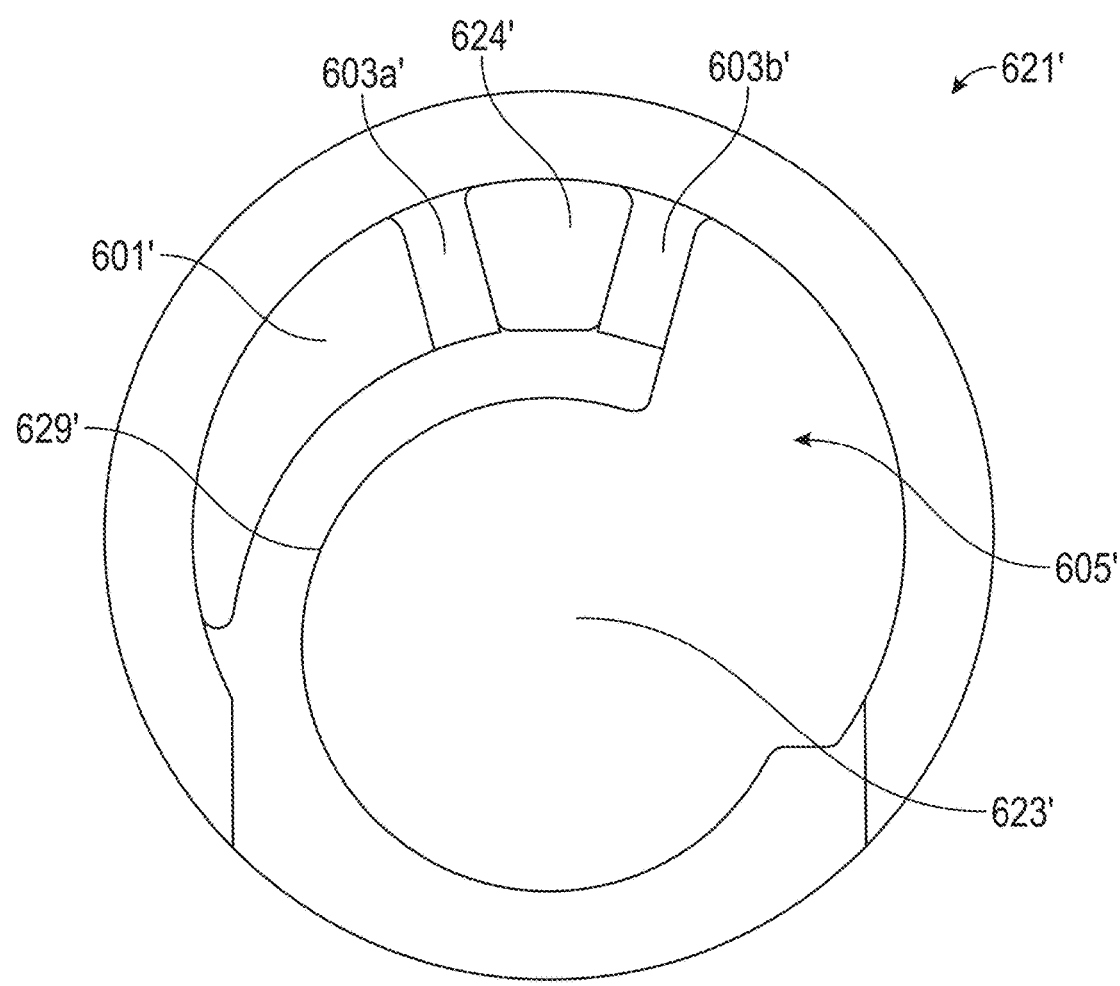

FIGS. 35A and 35B illustrate the distal end 621' of the cannula 620'. The cannula 620' can include the first channel 623', the second channel 624', and/or the third channel 601'. The first, second, and/or third channels 623', 624', 601' can be defined within an interior space defined by an outer wall of the cannula 620'. In some implementations, including the illustrated example, the outer wall of the cannula 620' can be curved or circularly shaped. In other implementations, other external geometries for the outer wall of the cannula 620' are possible. In some non-limiting examples, the outer wall of the cannula 620' can be octagonal, trapezoidal, ovoid, semilunar, a combination thereof, and/or the like. The shape of the outer wall of the cannula 620' may depend on the desired application and/or the internal channel configurations of the cannula 620'. The cannula 620' can include one or more internal or inner walls within the outer cannula wall that can divide the interior space into the first, second, and/or third channels 623', 624', 601'. For example, an inner wall 629' can separate the first channel 623' from the second channel 624' and the third channel 601'. For example, the first channel 623' can be substantially isolated from the other channels 624', 601' along the entire or a majority of the length of the cannula 620'.

The first, second, and third channels 623', 624', 601' can have substantially consistent cross-sectional shapes from the proximal end 622' to the distal end 621' of the cannula 620'. The first channel 623' can be located within a curved lower portion of the cannula 620'. In some implementations, the first channel 623' can include a main channel portion and one or more side channel portions extending from the main channel portion. One or more of the inner walls can at least partially define the main channel portion and the one or more side channel portions. For example, as shown in FIG. 35B, the first channel 623' can include a first side portion 605'. A main portion of the first channel 623' can be circularly shaped and configured to receive a shaft of a tool or instrument, such as the shaft 710 of the tool assembly 700. The shape of the main portion of the first channel 623' can be at least partially defined by the inner walls 629'. The first side portion 605' can extend radially outwardly from the main portion. The shape of the first side portion 605' can be at least partially defined by the inner walls 629', 603b', in the illustrated example. The first side portion 605' can be configured for suction/irrigation and can provide an enlarged portion (e.g., a clearance passage) of the first channel 623' for these functions. For example, the shaft 710 may generally fill the main portion of the first channel 623' (see e.g., FIG. 23). As such, suction and irrigation can occur in the first side portion 605' or otherwise around the shaft 710. For example, the first side portion 605' can promote (e.g., allow or direct) fluid communication around the main portion of the first channel 623' and the shaft of the tool (e.g., the shaft 710 of the tool assembly 700).

Including the side portion 605' in the first channel 623' can provide an advantage of defining a dedicated portion of the first channel 623' for suction and/or irrigation, as opposed to suction and irrigation only occurring around the shaft 710 of the tool assembly 700 when received in the first channel 623'. In the illustrated arrangement, suction and irrigation in the first channel 623' can occur both around the shaft 710 of the tool assembly 700 and in the dedicated side portion 605', which is desirable. Defining a side portion 605' in the first channel 623' can be particularly advantageous when the shaft 710 of the tool assembly 700 substantially occupies a majority of the main portion of the first channel 623'. For example, when the shaft 710 of the tool assembly 700 is in contact with the inner wall 629' of the cannula 620'.

As shown in FIG. 35B, the cannula 620' can include a plurality of inner walls that can separate the various channels along the length of the cannula 620'. For example, the first inner wall 629' can separate the first channel 623' from the second channel 624' and third channel 601'. A second inner wall 603a' can separate the third channel 601' from the second channel 624'. A third inner wall 603b' can extend from the first inner wall 629' to complete the separation of the first channel 623' from the second channel 624', and to partially define the shape of the first side portion 605'. The inner walls 629', 603a', 603b' can extend at least a majority of the length of the cannula 620' from the proximal end 622' to the distal end 621'. In some implementations, additional inner walls can be included to further divide the interior space of the cannula 620'. In some implementations, the second channel 624' can have a rectangular or trapezoidal cross-sectional shape. In some implementations, the second channel 624' can be configured to house at least a portion of the camera assembly 690' and/or associated components. The third channel 601' can be radially outward of the first channel 623'. The third channel 601' can be configured for suction, irrigation, or both. In the illustrated example, the third channel 601' is configured to alternate between suction and irrigation, depending on the configuration of the valve assembly 800'.

Figure 37A:
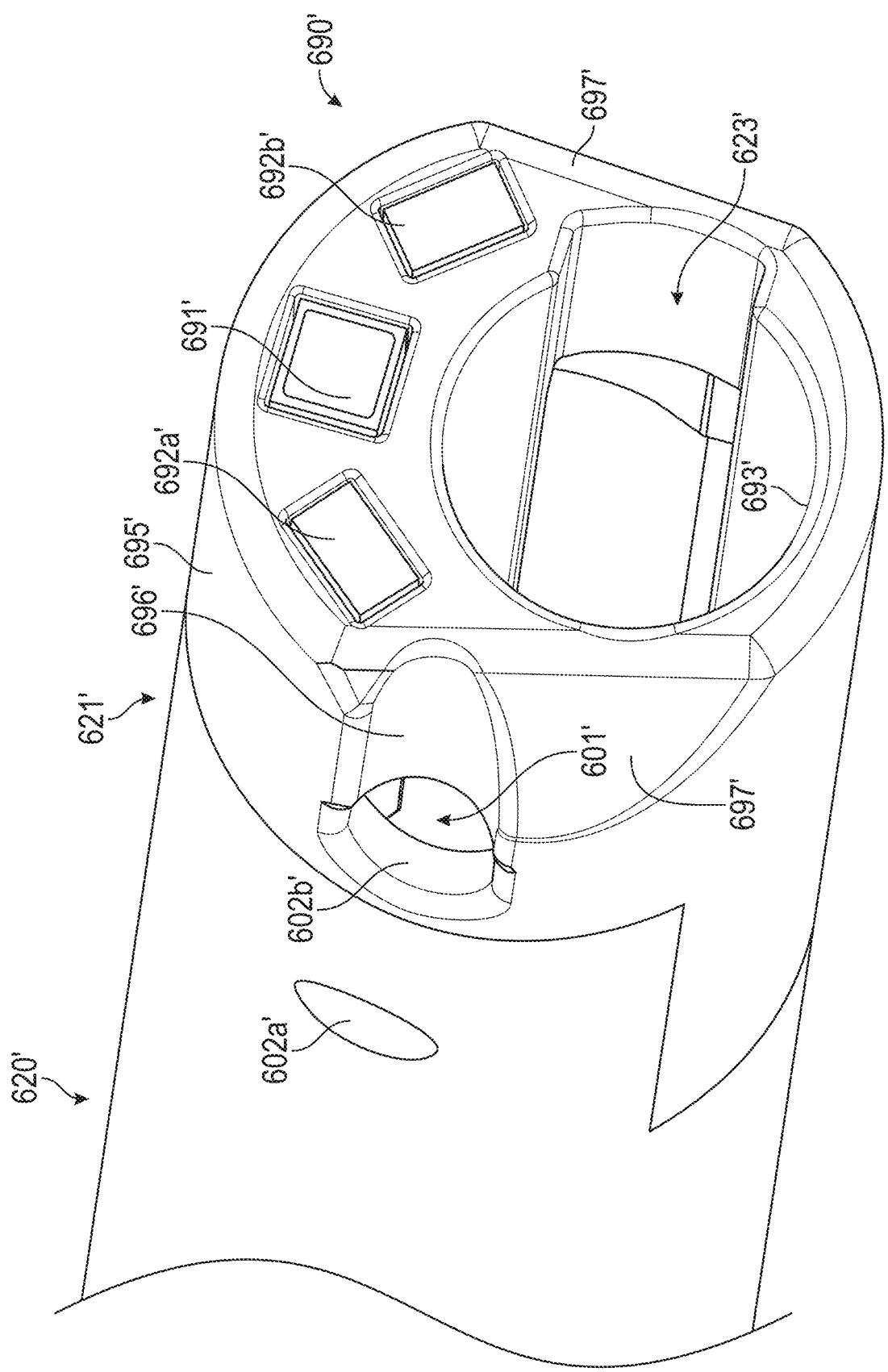
FIGS. 37A and 37B show a cannula cap portion the cannula of the endoscope of FIG. 33, in accordance with implementations of the disclosure.

As shown in FIG. 35A, the cannula 620' can include a first channel port 602a' that extends through the outer wall of the cannula 620' and into the third channel 601' near the distal end 621'. The first channel port 602a' can be configured to allow fluid communication between an environment external to the cannula 620' and the third channel 601'. The first channel port 602a' can be positioned on a substantially opposite side of the cannula 620' from the first side portion 605' of the first channel 623'. Spacing the first channel port 602a' opposite and away from the distal opening of first side portion 605' can provide a benefit of minimizing a circular flow of suction and irrigation at the tip of the cannula 620' (or the cannula cap portion 695') when inserted into an anatomic space. For example, as shown in FIG. 37A, the first channel port 602a' (and the second channel port 602b' when included) can both be proximal to the distal opening of the first channel 623'. Accordingly, flow through the ports 602a' and/or 602b' can be in a different direction and location than flow through the first channel 623', which may occur primarily through the distal end of the first side portion 605'.

In some implementations, the cannula 620' can be manufactured using extrusion (e.g., polymer extrusion). Extrusion manufacturing can allow for various configurations of the internal channels of the cannula 620' (e.g., the first channel 623', second channel 624', third channel 601', and/or the like). In some cases, the various inner walls 629', 603a', 603b' can be formed during the manufacturing of the cannula 620'. In some cases, the inner walls 629', 603a', 603b' can be connected to the inside of the cannula 620'. In other implementations, the inner walls 629', 603a', 603b' can be elevations or grooves incorporated into the shaft of a tool, such as the tool assembly 700, inserted into the cannula 620'.

In such an implementation, the cannula 620' may only include one main channel, such as the first channel 623', and the third channel 601' and/or the first side portion 605' may be defined by the elevations or grooves on the tool shaft (e.g., the shaft 710). Generally, the second channel 624' is isolated from the cannula 620', even in such an arrangement, to protect the camera assembly 690' and associated components. However, when the second channel 624' is configured for suction and/or irrigation, the second channel 624' may also be defined by the elevations or grooves on the tool shaft.

With continued reference to FIGS. 35A and 35B, the total cross-sectional area of the third channel 601' can be smaller than the total cross-sectional area of the first channel 623'. Such an arrangement can provide a benefit of increasing the fluid pressure of fluid traveling through the third channel 601' compared to the first channel 623'. For example, when connected to the same irrigation hose (e.g., via one of the harness ports 644', 645'), the velocity of fluid exiting the third channel 601' (e.g., through the channel port(s) 602a', 602b') can be greater than the velocity of fluid exiting the first channel 623' due to the smaller cross-sectional area of the third channel 601'. Configuring the third channel 601' to have a smaller size than the first channel 623' can allow for a more pressurized egress of the fluid from the tip of the cannula 620' and/or the cannula cap portion 695', which can be beneficial when clearing debris within or outside of the cannula 620'. In certain applications, a higher fluid pressure may be used to displace, alter, or otherwise manipulate tissue.

In some implementations, the total cross-sectional area of the third channel 601' can be smaller than the total cross-sectional area of the first side portion 605'. For example, even when the shaft 710 of the tool assembly 700 is received within the main portion of the first channel 623', the total cross-sectional area of the third channel 601' can be smaller than the remaining unoccupied total cross-sectional area of the first channel 623', which may be primarily or wholly defined by the first side portion 605'. In some implementations, the total cross-sectional area of the third channel 601' can be between 50% and 100% smaller than the total cross-sectional area of the first side portion 605'. In other implementations, the total cross-sectional area of the third channel 601' can be more than 50% smaller than the total cross-sectional area of the first side portion 605'.

Figure 36:
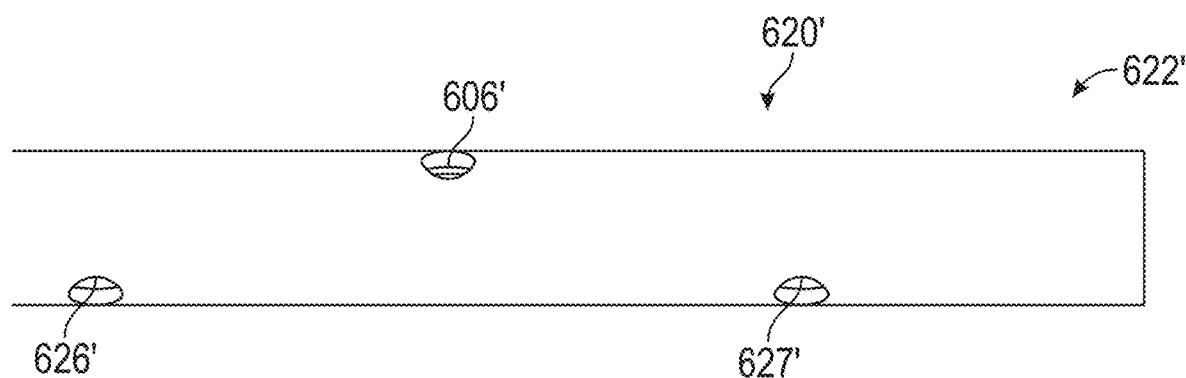
FIG. 36 show a proximal end the cannula of the endoscope of FIG. 33, in accordance with implementations of the disclosure.

FIG. 36 illustrates a side isolation view of the proximal end 622' of the cannula 620'. The cannula 620' can differ from the cannula 620 of at least FIG. 21 in that the cannula 620' can include a third port for communication with the third channel 601'. For example, the cannula 620' can include the first port 626', the second port 627', and a third port 606'. The ports 626', 627', 606' can extend through at least one side of the outer wall of the cannula 620'. The first port 626' can be in communication with the first channel 623'. The second port 627' can be in communication with the first channel 623'. The third port 606' can be in communication with the third channel 601'. The second port 627' can be spaced apart from the first port 626', with the third port 606' therebetween. The first port 626' and the second port 627' can be radially aligned about the central axis of the cannula 620', with the third port 606' being radially offset from the first and second ports 626', 627'. Arranging the ports 626', 627', 606' in this manner can facilitate the ability of the endoscope 600 to alternate between suction and irrigation in the first channel 623' and third channel 601', as described further with reference to at least FIGS. 38A-39B. For example, the valve assembly 800' can be used to selectively direct the first tube 681' to either the first port 626' or the third port 606'. Similarly, the valve assembly 800' can be used to selectively direct the second tube 682' to the third port 606' or the second port 627'. As such, one tube 681', 682' can be in fluid communication with one fluid channel 623', 601', while the other tube 681', 682' can be in fluid communication with the other fluid channel 623', 601'.

Figure 38A:
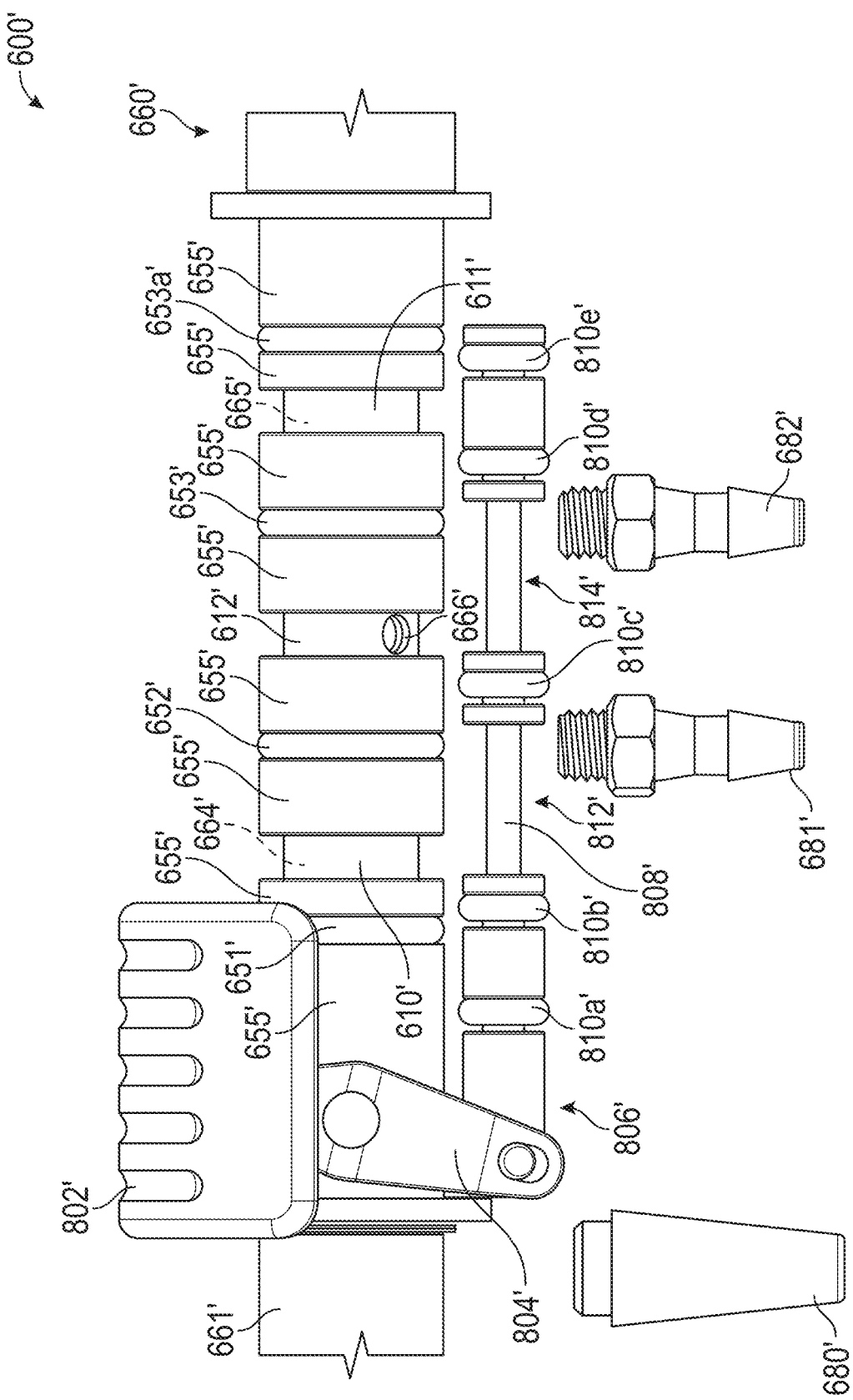
FIG. 38A shows a valve assembly of the endoscope of FIG. 33, in accordance with implementations of the disclosure.
Figure 38B:
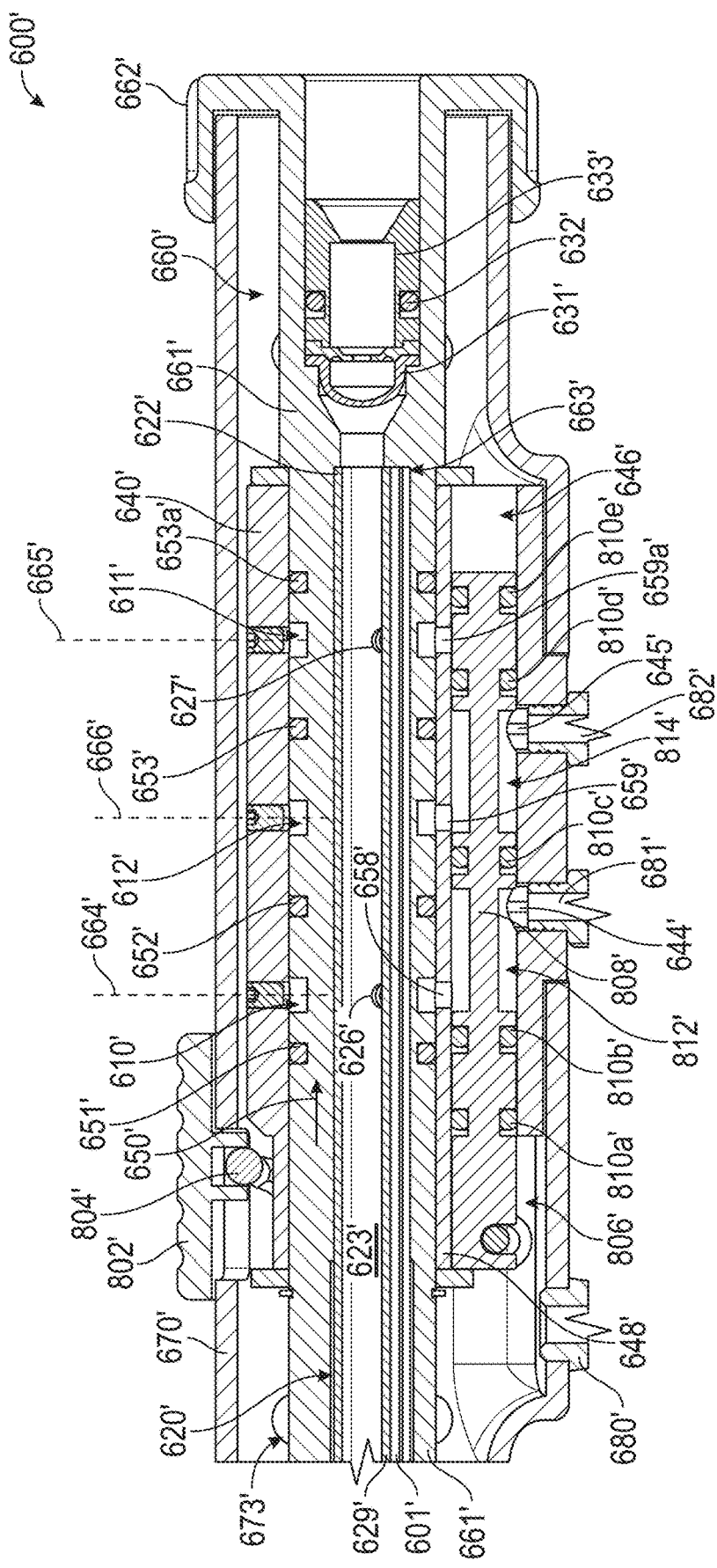
FIG. 38B shows a section view of a portion of the endoscope of FIG. 33, in accordance with implementations of the disclosure.

As shown in at least FIG. 38B, the proximal end 622' of the cannula 620' can be received within the interior 673' of the body 670' through the distal end 671' (see e.g., FIG. 34) of the body 670'. As shown in FIG. 33, the distal end 621' of the cannula 620' can protrude from the distal end 671' of the body 670'. The distal end 671' of the body 670' can include an aperture for receiving the cannula 620'. The body 670' may be gripped or held by the operator during use. Accordingly, the body 670' may also be referred to herein as the "handle 670'" of the endoscope 600'.

In some implementations, the cannula 620' can be removable from the body 670' of the endoscope 600'. For example, a first cannula 620' with a certain length and geometry may be removed and replaced in the endoscope 600' with a second cannula 620' with a different length and/or geometry. It can be desirable to have varied and interchangeable cannulas 620' in some use cases. Configuring the cannula 620' to be removable from the body 670' can provide certain advantages. For example, during a particular surgical case, it may be desirable to use multiple different cannulas 620' over the course of the surgery. For example, at certain points during the surgery, cannulas 620' with different lengths may be required or desired. Similarly, over the course of the surgery, cannulas 620' with different outer diameters, different channel configurations, different shapes/curvatures (see e.g., cannula 620' of FIG. 40), and/or the like can be utilized when the body 670' is configured to be removably connected to the cannulas 620'.

As shown in at least FIG. 34, the endoscope 600' can include a forward seal 628'. The forward seal 628' can be formed of an elastic material. Forward seal 628' can include a central aperture. The central aperture of the forward seal 628' can be sized to receive the cannula 620' and seal against the outer wall thereof. The forward seal 628' can include a portion that is at least partially received within the distal end 671' of the body 670'. The forward seal 628' can provide a liquid-tight seal between the cannula 620' and an inner wall of the central aperture of the forward seal 628'.

Figure 37B:
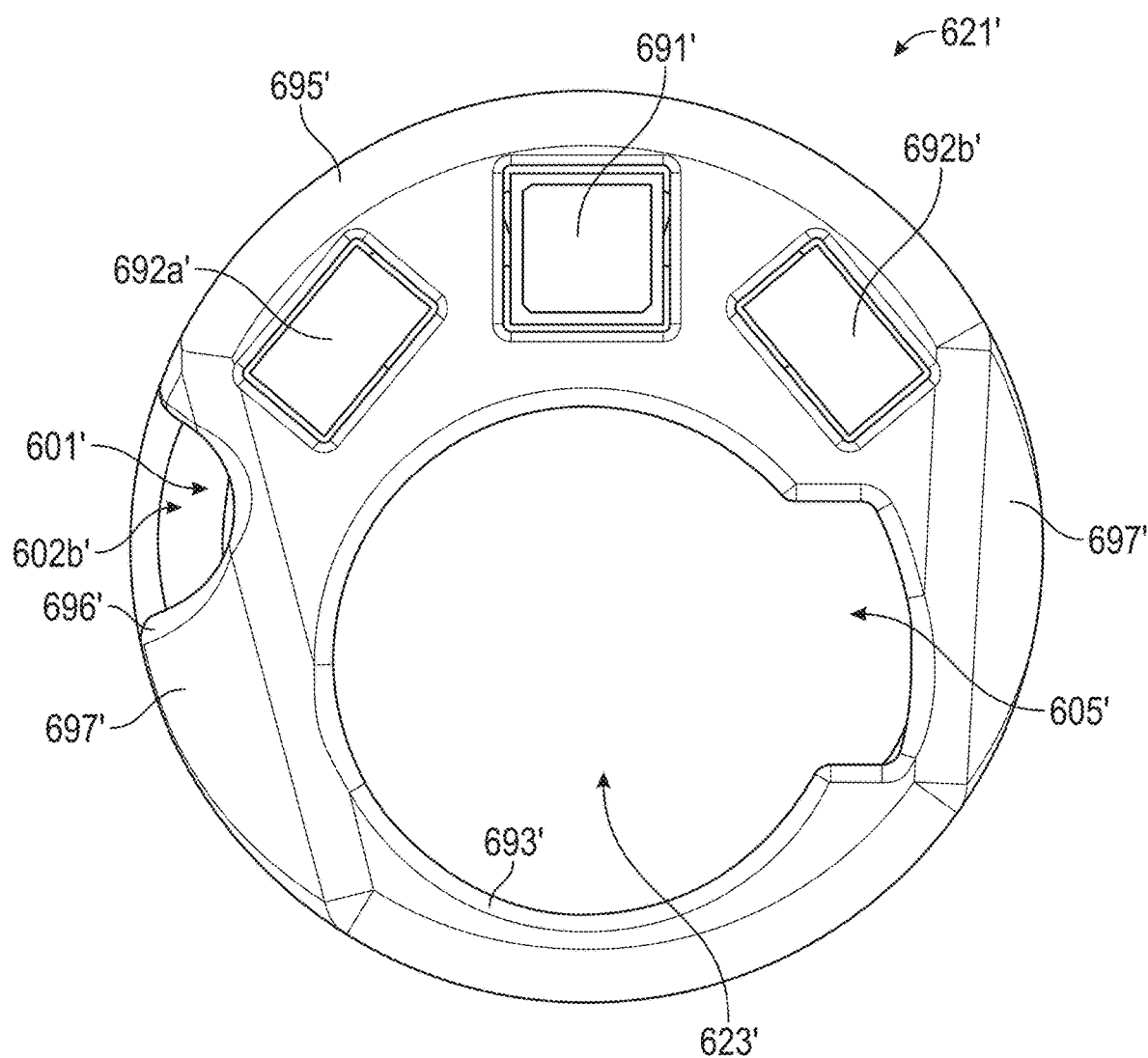

FIGS. 37A and 37B illustrate a perspective view and a front view respectively of the distal end 621' of the cannula 620' and a cannula cap portion 695' (also referred to herein as the "optical cap portion 695'"). The cannula cap portion 695' can extend from or be connected to the distal end 621' of the cannula 620'. In the illustrated example, the cannula cap portion 695' can be removably connected to the distal end 621' of the cannula 620'. In some implementations, the cannula cap portion 695' can be permanently or removably connected to the distal end 621' of the cannula 620'. The cannula cap portion 695' can house at least a portion of the camera assembly 690' (e.g., a first camera chip, a second camera chip, etc.). The camera assembly 690' may include one or more camera chips like the camera chip 200 and/or additional/alternative camera chips. The camera assembly 690' can be similar or identical to the camera assembly 690 of the optical cannula system 500.

The external contour of the optical cap 695' may be tapered distally. For example, the outer surface of the optical cap 695' can include one or more tapered portions 697' extending towards the distal end. The tapered portions 697' can allow the cannula 620' to present a more narrowed tip compared to a cannula with a consistent cylindrical outer surface, which can facilitate improved passage through tissue in operation. For example, the one or more tapered portions 697' can at least partially define a distally narrowing outer surface of the optical cap 695'.

In some implementations, a removable pointed obturator (not shown) can be utilized with the endoscope 600'. For example, the obturator could be inserted distally into working channel 623' or over the distal end 621' of the cannula 620' to help facilitate tissue insertion and cannula passage. In this example, the cannula 620' could then be removed from the tissue, the obturator removed, and the cannula 620' reinserted through the opened tissue incision/space.

The cannula cap portion 695' can include a central cutout or opening 693' that can be at least partially aligned with the first channel 623' and the first side portion 605'. The opening 693' can allow the first channel 623' (and the first side portion 605') to communicate with the external environment through the cannula cap portion 695'.

The cannula cap portion 695' can include openings/holes to receive components of the camera assembly 690'. For example, the cannula cap portion 695' can house one or more camera chip(s) 691' and/or one or more lights sources (e.g., a first light source 692a' and/or a second light source 692b'). When the cannula cap portion 695' houses multiple camera chips 691' (e.g., two or more camera chips 691'), the camera chips 691' can be positioned beside each other (e.g., within the same opening or in adjacent openings of the cannula cap portion 695'). In some cases, the positions or orientations of the two camera chips 691' can be different to provide different viewing angles. For example, the multiple camera chips 691' may be congruent or divergent from one another thereby overlapping and improving resolution or expanding the field of view. In some implementations, two camera chips 691' can be divergent between 0 degrees and 90 degrees. For example, an angle between the optical axis of the first camera chip 691' can be offset from the optical axis of the second camera chip 691' by between 0 and 90 degrees (e.g., between 0 degrees and 90 degrees, between 15 degrees and 75 degrees, between 30 degrees and 60 degrees, between 40 degrees and 50 degrees, values between the foregoing, etc.). As explained herein, images from the two camera chips 691' can be digitally combined to create a panoramic field of view. In some cases, images of the cannula cap portion 695', the distal end 621' of the cannula 620', portions of the tool assembly 700, and/or the like can be digitally removed or reduced from the combined panoramic field of view. For example, computer processing of the various images from the multiple camera chips 691' can be digitally enhanced or manipulated as might be required to digitally "erase" an instrument shaft (e.g., the outer shaft 710 and/or inner shaft 790 of tool assembly 700) or portions of a tool tip (e.g., the tool 720 of the tool assembly 700) from the image(s) once the instrument exits the associated distal cannula lumen (e.g., the first channel 623') of the cannula 620'.

As noted above, camera assembly 690' can be similar or identical to the camera assembly 690 of the optical cannula system 500. For example, a camera signal wire (not shown) can be positioned within the second channel 624' and can be electrically connected with the camera assembly 690' (e.g., the one or more camera chips 691', light sources 692', and/or the like). The camera signal wire can be electrically connected with an electrical coupler (not shown). The electrical coupler may be housed within the body 670' of the endoscope 600'. As explained herein, in some cases, an external electrical cable including an external coupler can be configured to electrically connect with the electrical coupler. In some implementations, the camera assembly 690' (including the one or more camera chips 691'), the external electrical cable, and/or the external coupled can be removeable from the endoscope 600' (e.g., from the body 670'). Such an arrangement can allow the body 670' to be reusable in some cases.

The cannula cap portion 695' can include a second channel port 602b'. The cannula cap portion 695' can include a recessed portion 696'. The second channel port 602b' can at least partially extend through the recessed portion 696', in some implementations. The recessed portion 696' can be formed in one of the tapered portions 697' and can allow improved access to the second channel port 602b', as shown in the front view of FIG. 37B. For example, the recessed portion 696' can increase the accessibility of the second channel port 602b' from the distal end of the optical cannula system 500'. The second channel port 602b' can be formed in the side of the cannula cap portion 695' and may be referred to herein as a "side port 602b'" of the cannula cap portion 695'. The second channel port 602b' can extend through the outer wall of the cannula 620' into the third channel 601'. As such, the second channel port 602b' can allow for fluid communication between the third channel 601' and an external environment through the cannula cap portion 695'. The second channel port 602b' can be distal to the first channel port 602a'.

Communication (e.g., fluid communication) between the third channel 601' and the external environment can occur through one or both of the first channel port 602a' and the second channel port 602b'. For example, the suction function of the third channel 601' can occur at both the ports 602a', 602b' and the irrigation function of the third channel 601' can occur at both the ports 602a', 602b'. Including multiple spaced apart ports 602a', 602b' in communication with the third channel 601' can provide a benefit of allowing continued operation of at least one of the ports 602a', 602b' in case the other becomes clogged. For example, if one port 602a', 602b' becomes clogged, the other port 602a', 602b' can remain functional (e.g., providing suction or irrigation) until the port is unclogged (e.g., by alternating between suction and irrigation in the third channel 601'). In some implementations, the cannula 620' can include additional channel ports along the length of the cannula 620' that are in fluid communication with either the third channel 601' or the first channel 623' and/or the first side portion 605'.

In some implementations, the cannula cap portion 695' can be configured to be used with a plurality of different cannulas with a variety of features. The cannula cap portion 695' can provide a benefit of housing the camera assembly 690' within a small component. Additionally, because the camera assembly 690' is housed within the cannula cap portion 695', the fluid channels (e.g., first channel 623', third channel 601', etc.) within the cannula 620' can have narrower tolerances and thin channel walls, while maintaining sufficient structural integrity. For example, having thinner channel walls (e.g., inner wall 629', inner wall 603a', inner wall 603b', and/or the like) in the cannula 620' can provide a benefit of maximizing the portions of the cannula 620' that can be utilized for suction and fluid transfer. For example, decreasing the size (e.g., thickness) of the channel walls of the cannula 620' can allow the cross-sectional areas of the channels utilized for fluid communication (e.g., channels 623', 601') to be increased without requiring an increase in the overall diameter of the cannula 620', which can be desirable.

Separating the camera assembly 690' within the cannula cap portion 695', as opposed to within the cannula 620', can allow the cannula 620' to be economically efficient to mass produce. For example, removing the camera assembly 690' can facilitate easier mass production of the cannula 620' using conventional manufacturing techniques, such as extrusion.

Having the camera assembly 690' within a removable cannula cap portion 695' can also provide a benefit of allowing easier modifications to the cannula cap portion 695'. For example, some camera and light (e.g., LED) configurations may be larger than others, particularly when multiple camera chips 691' and lights 692' are desired or required. Accordingly, configuring the cannula cap portion 695' separately from the cannula 620' can allow easier changes to the endoscope 600' for different applications by switching out the cannula cap portion 695' for the same cannula 620'.

Various implementations of the cannula cap portion 695' with different configurations can be utilized with the endoscope 600'. For example, implementations of the cannula cap portion 695' can differ from the illustrated example with changes in how the tip is tapered, where the fluid and suction ports (e.g., first channel port 602a', second channel port 602b', etc.) exit the cannula 620' walls and cannula cap portion 695', how the camera chips 691' and LED lights 692a', 692b' are positioned within the cannula cap portion 695', and/or the like. In some implementations, the camera chip(s) 691' and light sources 692a', 692b' may be housed within the cannula cap portion 695' side-by-side in a single opening.

In some implementations, the cannula cap portion 695' can include a channel port that extends through the side wall and through the cannula 620' into the first channel 623' (e.g., similar to the second channel port 602b'). For example, this channel port may allow for fluid communication between the first channel 623' and the external environment through the side wall of the cannula cap portion 695'. In this implementation, the channel port of the first channel 623' may be positioned on a substantially opposite side of the of the cannula cap portion 695' than the second channel port 602b' for the third channel 601'. In such an implementation, the opening 693' of the cannula cap portion 695' may be substantially circularly shaped and may not include a portion configured to align with the first side portion 605' of the first channel 623'. For example, fluid communication through the first channel 623' may occur primarily through the additional channel port and the shaft 710 of the tool assembly 700 may occupy all or a majority of the opening 693' when positioned within the cannula cap portion 695'.

In some implementations, the first channel 623' may include a second side portion similar to the first side portion 605'. The second side portion may be positioned on an opposite side as the first side portion 605'. In such an implementation, the opening 693' of the cannula cap portion 695' may be shaped accommodate and allow flow through the cannula cap portion 695' from both the first side portion 605' and the second side portion.

Referring back to FIG. 34, the rotation assembly 660' of the endoscope 600' can include a rotation handle 662', an insertion portion 661', and/or a channel 663'. The rotation assembly 660' can be configured to control the rotation of the cannula 620' relative to the body 670'. The rotation handle 662' can be configured to be accessible outside of the body 670', as shown in at least FIG. 38B. The insertion portion 661' can be connected to the rotation handle 662'. The rotation assembly 660' can differ from the rotation assembly 660 of FIG. 17 in the overall length of the insertion portion 661'. For example, the insertion portion 661' can extend further into the body 670' than the insertion portion 661 of the rotation assembly 660 extends into the body 670, in some implementations. As shown in FIG. 38B, the insertion portion 661' can be received within the interior 673' of the body 670'. In the illustrated example, the insertion portion 661' can extend through the entire length of the body 670' and out the proximal end 672' of the body 670'. In some cases, the forward seal 628' may be at least partially disposed around the insertion portion 661'.

With continued reference to FIG. 38B, the channel 663' of the rotation assembly 660' can include an inner wall sized to receive the proximal end 622' of the cannula 620'. The insertion portion 661' can include a first aperture 664', a second aperture 665', and a third aperture 666'. Each of the apertures 664', 665', 666' can be spaced apart from each other along the length of the insertion portion 661'. The third aperture 666' can be disposed between the first aperture 664' and the second aperture 665'. The apertures 664', 665', 666' can extend through the outer wall of the insertion portion 661' to provide communication (e.g., fluid communication) within the channel 663'.

The rotation assembly 660' can be assembled with the body 670'. The rotation assembly 660' can be assembled with the proximal portion 672' of the body 670'. The insertion portion 661' can be inserted within the interior space 673'. The rotation handle 662' can abut the proximal end 672' of the body 670'. The rotation assembly 660' can be rotatable relative to the body 670', similar to the rotation assembly 660 of the system 500. The proximal end 622' of the cannula 620' can be received within the insertion portion 661'. For example, The proximal end 622' of the cannula 620' can be received within the channel 663'. The proximal end 622' of the cannula 620' can be rotationally fixed with the insertion portion 661' such that rotation of the rotation handle 662' causes corresponding rotation of the cannula 620'.

The apertures 664', 665', 666' of the rotation assembly 660' can align with and/or be in communication with the ports 626', 627', 606' of the cannula 620', respectively. For example, the first aperture 664' can be aligned with the first port 626', the second aperture 665' can be aligned with the second port 627', and the third aperture 666' can be aligned with the third port 606'. As such, the first and second apertures 664', 665' can be configured to facilitate fluid communication through the rotation assembly 660' with the first channel 623', and the third aperture 666' can be configured to facilitate fluid communication through the rotation assembly 660' with the third channel 601'.

As shown in FIG. 38A, the rotation assembly 660' can also differ from the rotation assembly 660 of FIG. 17 in that the external surface of the insertion portion 661' can include a plurality of spacer portions 655' along its length. The spacer portions 655' can be cylindrical portions of the insertion portion 661' having an enlarged diameter relative to the outer diameter of the channel 663'. Gaps between the spacer portions 655' can define a plurality of grooves. For example, the spacer portions 655' can define a first groove 610', a second groove 611', and/or a third groove 612'. The third groove 612' can be positioned between the first groove 610' and the second groove 611'. The apertures 664', 665', 666' can be formed in the grooves 610', 611', 612' respectively. The other grooves defined by the spacer portions 655' can be configured to receive seals, at explained further herein. The spacer portions 655' can serve a similar function as the spacers 654, 655, 656, 657 of the endoscope 600 shown in at least FIG. 21. In some implementations, the spacer portions 655' can be integral with the insertion portion 661' (e.g., formed as a single unit). In other implementations, the spacer portions 655' can be separate from the insertion portion 661' and can be configured to be disposed on the outer surface of the insertion portion 661'. In such an implementation, the spacer portions 655' may be considered part of a harness assembly 650' of the endoscope 600'.

As shown in at least FIGS. 34 and 38B, the endoscope 600' can include a harness assembly 650'. The harness assembly 650' can provide communication between the tubes 681', 682' and the cannula 620', including when the cannula 620' is rotated. The harness assembly 650' can include a harness block 640' and a plurality of seals. For example, the plurality of seals can include a first seal 651', a second seal 652', a third seal 653', and/or a fourth seal 653a' (collectively "seals 651'-653a'"). The seals 651'-653a' can be in the form of O-rings, in one example. The harness block 640' and the seals 651'-653a' can create one or more fluid pathways for providing irrigation and/or suction to the cannula 620' (e.g., through the ports 626', 627', 606' as discussed further below).

The harness block 640' can differ from the harness block 640 of the endoscope 600 of FIG. 17 in that the harness block 640' can be configured to receive at least a portion of the valve assembly 800'. For example, the harness block 640' can include a central channel 642' and a second channel 646'. The second channel 646' can be configured to receive at least a portion of a spool valve 806' of the valve assembly 800', as explained further herein. For example, a valve shaft 808' of the spool valve 806' can be at least partially disposed within the second channel 646'. An internal wall 648' can separate the central channel 642' from the second channel 646'. The internal wall 648' can also at least partially define the walls of central channel 642' and/or the second channel 646. The central channel 642' can have an inner diameter and inner surface. The central channel 642' can be configured to receive the insertion portion 661' of the rotation assembly 660'. As such, the proximal end 622' of the cannula 620' can also be received within the central channel 642' when connected to the insertion portion 661'. For example, the inner surface of the central channel 642' can be disposed about the proximal portion 622' of the cannula 620'.

The harness block 640' can be configured to be rotationally fixed within the body 670'. For example, the insertion portion 661' can be configured to rotate within the central channel 642' without causing corresponding rotation of the harness block 640'.

The seals 651'-653a' of the harness assembly 650' can be assembled within the central channel 642' of the harness block 640'. The seals 651'-653a' can engage with and/or seal against the inner surface of the central channel 642'. Accordingly, when the proximal portion 622' of the cannula 620' is received within the central channel 642', the seals 651'-653a' can be disposed between the outer cannula wall and the inner surface of the central channel 642'.

As shown in FIG. 38B, when the proximal portion 622' of the cannula 620' is received within the insertion portion 661' of the rotation assembly 660', the insertion portion 661' can be positioned between the outer wall of the cannula 620' and the seals 651'-653a'. For example, the seals 651'-653a' can be disposed within the plurality of grooves defined by the spacer portions 655'. The seals 651'-653a' can be circumferential seals. In the illustrated example, a pair of seals are disposed on each side of the grooves 610', 611', 612'. For example, the first seal 651' and the second seal 652' can be disposed on either side of the first groove 610', the second seal 652' and the third seal 653' can be disposed on either side of the third groove 612', and the third seal 653' and the fourth seal 653a' can be disposed on either side of the second groove 611'. When arranged in such a manner, the seals 651'-653a' can prevent fluid communication between the grooves 610', 611', 612' and their associated apertures 664', 665', 666'. For example, each aperture 664', 665', 666' of the insertion portion 661' can be fluidly isolated from each other. This arrangement can also allow the ports 626', 627', 606' of the cannula 620' to be fluidly isolated from each other, because the ports 626', 627', 606' can be aligned with the apertures 664', 665', 666' of the insertion portion 661'. The arrangement can also allow the seals 651'-653a' to define fluid channels between the outer cannula wall and the inner surface of the central channel 642'.

With continued reference to FIG. 38B, the harness block 640' can include a first harness port 644' and/or a second harness port 645'. The harness ports 644', 645' can be openings or apertures extending through an outer wall of the harness block 640'. The harness ports 644', 645' may partially extend through the body 670'. The harness ports 644', 645' can provide or allow for fluid communication with the second channel 646'. For example, the harness ports 644', 645' can define fluid passageways into the second channel 646'. The first harness port 644' can be configured to receive the first tube 681'. The second harness port 645' can be configured to receive the second tube 682'. Accordingly, the second channel 646' can be in fluid communication with the first tube 681' via the first harness port 644' and the second tube 682' via the second harness port 645'. When connected, the first tube 681' can be aligned with the first harness port 644' and the second tube 682' can be aligned with the second harness port 645'.

To provide fluid communication between the second channel 646' and the central channel 642' of the harness block 640', the internal wall 648' can include one or more internal apertures. For example, the harness block 640' can include a first internal aperture 658', a second internal aperture 659a', and/or a third internal aperture 659' extending through the internal wall 648'. The third internal aperture 659' can be positioned between the first internal aperture 658' and the second internal aperture 659a'. As such, the fluid channels can be defined within the harness block for communication with the first and second harness ports 644', 645'.

As shown in FIG. 38B, the first internal aperture 658' can be aligned with the first groove 610' and the first aperture 664' of the insertion portion 661'. The first internal aperture 658' can be aligned with the first port 626' of the cannula 620'. This arrangement can provide a fluid pathway between the first channel 623' of the cannula 620' and the second channel 646' of the harness block 640', which can be in fluid communication with the tubes 681', 682'. Similarly, the second internal aperture 659a' can be aligned with the second groove 611' and second aperture 665' of the insertion portion 661'. The second internal aperture 659a' can be aligned with the second port 627' of the cannula 620'. This arrangement can provide a fluid pathway between the first channel 623' of the cannula 620' and the second channel 646' of the harness block 640', which can be in fluid communication with the tubes 681', 682'. Similarly, the third internal aperture 659' can be aligned with the third groove 612' and the third aperture 666' of the insertion portion 661'. The third internal aperture 659' can be aligned with the third port 606' of the cannula 620'. This arrangement can provide a fluid pathway between the third channel 601' of the cannula 620' and the second channel 646' of the harness block 640', which can be in fluid communication with the tubes 681', 682'. As explained herein, the valve assembly 800' can be used to selectively provide fluid communication between one of the tubes 681', 682' and the first channel 623' and the other of the of the tubes 681', 682' and the third channel 601'.

FIG. 38A illustrates a side view of select components of the endoscope 600', including the valve assembly 800'. As shown in FIGS. 38A and 38B, the valve assembly 800' can include a valve handle 802', a valve hinge 804', and a spool valve 806'. As shown in FIG. 33, the valve handle 802' can be connected to the valve hinge 804' at a first end of the valve hinge 804'. The valve handle 802' can be moveable relative to the body 670'. Similarly, the spool valve 806' can be connected to the valve hinge 804' at a second end of the valve hinge 804'. The valve hinge 804' can be pivotably connected to the harness block 640' between its first and second ends. As such, movement of the valve handle 802' in the proximal or distal direction along the body 670' can cause movement of the spool valve 806' in the opposite direction.

The spool valve 806' can extend through the second channel 646' in the harness block 640'. The spool valve 806' can include a valve shaft 808', a plurality of seals 810', a first recessed portion 812', and/or a second recessed portion 814'. The plurality of seals 810' can be disposed on the valve shaft 808'. The plurality of seals 810' can be configured to seal against the valve shaft 808' and/or against an inner wall of the second channel 646' under axial movement. The plurality of seals 810' can include a first seal 810a', a second seal 810b', a third seal 810c', a fourth seal 810d', and/or a fifth seal 810e'. The seals 810' can be arranged along the valve shaft 808' to create the first and second recessed portions 812', 814'. For example, the first and second seals 810a', 810b' can be distal to the third seal 810c' to form the first recessed portion 812'. Similarly, the fourth and fifth seals 810d', 810e' can be proximal to the third seal 810c' to form the second recessed portion 814'. The first tube 681' can be aligned with the first recessed portion 812' and the second tube 682' can be aligned with the second recessed portion 814'.

Figure 39A:
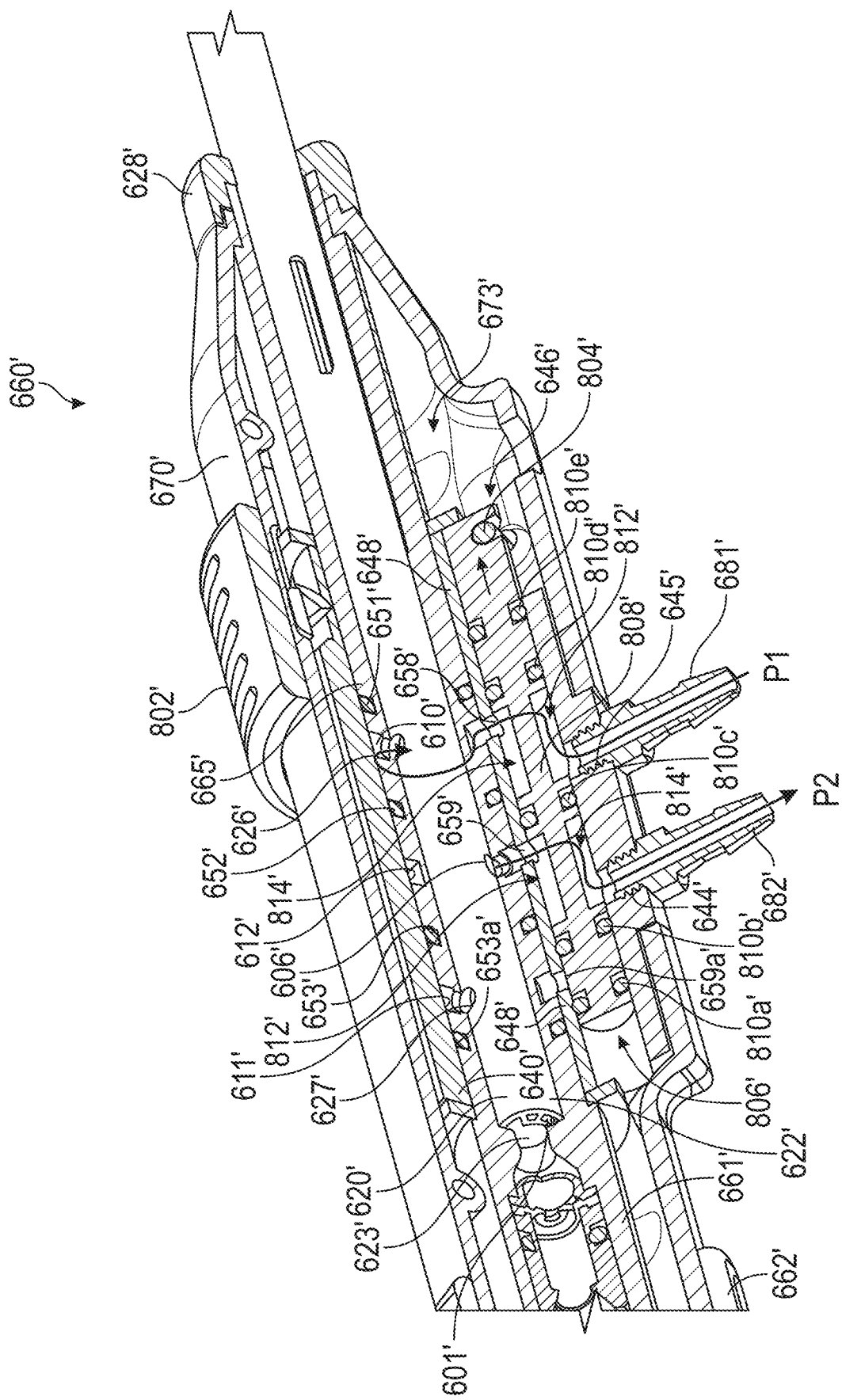
FIGS. 39A and 39B show cross-sectional views of the endoscope of FIG. 33 in a first valve configuration and a second valve configuration respectively, in accordance with implementations of the disclosure.
Figure 39B:
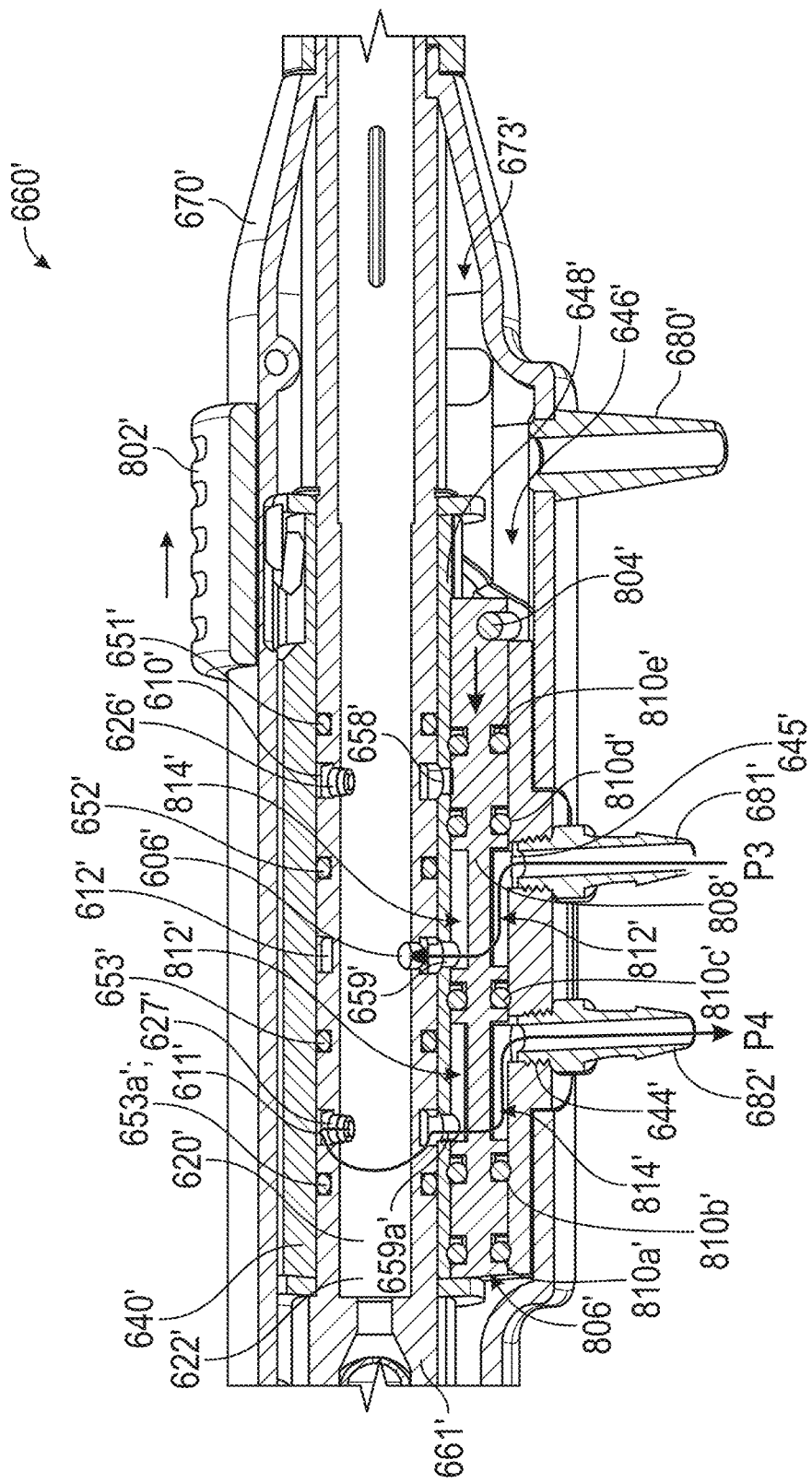

As shown in FIGS. 39A and 39B, the tubes 681', 682' can maintain alignment with the respective recessed portions 812', 814' as the valve assembly 800' transitions between configurations. As such, fluid traveling through the tubes 681', 682' can pass freely over the respective recessed portions (e.g., around the valve shaft 808') and to and from the ports 626', 627', 606' in the cannula 620'.

The optical cannula system 500' can move between configurations to selectively utilize the first channel 623' and the third channel 601' for suction and irrigation. For example, the valve assembly 800' can be moved or transition between a first valve configuration and a second valve configuration. The valve handle 802' can be configured to move the valve assembly 800' between the first configuration and the second configuration. Moving the valve handle 802' can cause the position of the valve shaft 808' within the second channel 646' of the harness block 640' to change. The position of the valve shaft 808' within the second channel 646' can define which internal apertures of the plurality of internal apertures 658', 659', 659a' the first harness port 644' and the second harness port 645' are in fluid communication with.

FIGS. 39A and 39B show cross-sectional views of the endoscope 600' in the first valve configuration and second valve configuration respectively. In the first valve configuration (shown in at least FIGS. 38A, 38B and 39A), the first tube 681' is in fluid communication with the first port 626' and the first channel 623'. In this arrangement, the third seal 810c' prevents the first tube 681' from being in fluid communication with the third port 606'. For example, the third seal 810c' can ensure that the first tube 681' is only in fluid communication with the first internal aperture 658' of the harness block 640'. In the first valve configuration, the second tube 682' is in fluid communication with the third port 606' and the third channel 601'. In this arrangement, the fourth seal 810d' prevents the second tube 682' from being in fluid communication with the second port 627'. In this arrangement, the third seal 810c' prevents the second tube 682' from being in fluid communication with the first port 626'. For example, the third seal 810c' and the fourth seal 810d' can ensure that the second tube 682' is only in fluid communication with the third internal aperture 659' of the harness block 640'. As such, when one of the tubes 681', 682' is configured for suction and the other for irrigation, one of the channels 623', 601' can be configured for suction, while the other is configured for irrigation. For example, FIG. 39A shows fluid pathways through the tubes 681', 682'.

As explained herein, in some implementations, the first tube 681' is configured for irrigation and the second tube 682' is configured for suction. For example, the first tube 681' can form the distal end of an irrigation hose and the second tube 682' can form the distal end of a suction hose. In other implementations, the first tube 681' is configured for suction and the second tube 682' is configured for irrigation. For example, the first tube 681' can form the distal end of a suction hose and the second tube 682' can form the distal end of an irrigation hose. In either implementation, the irrigation hose and suction hose can be configured to be removably connected to the body 670' of the endoscope 600'. In some implementations, the first tube 681' and the second tube 682' can extend from the body in a parallel configuration.

As shown via the arrow P1, in the first configuration, the first tube 681' can be used to provide irrigation through the first channel 623' via the first port 626' of the cannula 620'. For example, a first fluid pathway can extend from the first tube 681' through the first harness port 644', around the first recessed portion 812' of the valve shaft 808', through the first internal aperture 658' of the harness block 640', into the first groove 610' and through the first aperture 664' of the insertion portion 661', through the first port 626' of the cannula 620', and into the first channel 623' of the cannula 620'.

As shown via the arrow P2, in the first configuration, the second tube 682' can be used to provide suction through the third channel 601' via the third port 606' of the cannula 620'. For example, a second fluid pathway can extend from third channel 601' of the cannula 620', through the third port 606' of the cannula 620', through the third aperture 666' and into the third groove 612' of the insertion portion 661', through the third internal aperture 659' of the harness block 640', around the second recessed portion 814' of the valve shaft 808', through the second harness port 645', and into the second tube 682'.

While FIG. 39A shows a configuration where both channels 623', 601' are operating for irrigation and suction respectively at the same time, it is recognized that the valve assembly 800' can be in the first configuration with only one of the first channel 623' or the third channel 601' operating. For example, in the first configuration, the first channel 623' may be providing irrigation while the third channel 601' is not providing suction (e.g., by controlling the second tube 682'). In another example, the third channel 601' may be providing suction while the first channel 623' is not being utilized for irrigation (e.g., by controlling the first tube 681').

As shown in FIG. 39B, the valve assembly 800' can transition from the first configuration (shown in FIG. 39A) to the second configuration. To move the valve assembly 800' to the second configuration, the valve handle 802' can be moved relative to the body 670' (e.g., the valve handle 802' can be slid distally). Distal movement of the valve handle 802' can cause the spool valve 806' to move proximally, changing the location of the plurality of seals 810' relative to the cannula ports 626', 627', 606'. In the second configuration of FIG. 39B, the location of the third seal 810c' has changed relative to the first configuration such that the first tube 681' is in fluid communication with the third port 606' and the third channel 601'. In this arrangement, the second seal 810b' prevents the first tube 681' from being in fluid communication with the first port 626'. In this arrangement, the third seal 810c' prevents the first tube 681' from being in fluid communication with the second port 627'. For example, the fourth seal 810d' and the third seal 810c' can ensure that the first tube 681' is only in fluid communication with the third internal aperture 659' of the harness block 640'. In the second valve configuration, the location of the fourth seal 810d' has changed such that the second tube 682' is in fluid communication with the second port 627' and the first channel 623'. In this arrangement, the third seal 810c' prevents the second tube 682' from being in fluid communication with the third port 606'. For example, the third seal 810c' can ensure that the second tube 682' is only in fluid communication with the second internal aperture 659a' of the harness block 640'. For example, FIG. 39B shows fluid pathways through the tubes 681', 682'.

As shown via the arrow P3, the first tube 681' can be used to provide irrigation through the third channel 601' via the third port 606' of the cannula 620'. For example, a third fluid pathway can extend from the first tube 681' through the first harness port 644', around the first recessed portion 812' of the valve shaft 808', through the third internal aperture 659' of the harness block 640', around the third groove 612' and through the third aperture 666' of the insertion portion 661', through the third port 606' of the cannula 620', and into the third channel 601' of the cannula 620'.

As shown via the arrow P4, the second tube 682' can be used to provide suction through the first channel 623' via the second port 627' of the cannula 620'. For example, a fourth fluid pathway can extend from the first channel 623' of the cannula 620', through the second port 627' of the cannula 620', through the second aperture 665' and into the second groove 611' of the insertion portion 661', through the second internal aperture 659a' of the harness block 640', around the second recessed portion 814' of the valve shaft 808', through the second harness port 645', and into the second tube 682'.

While FIG. 39B shows a configuration where both channels 623', 601' are operating for suction and irrigation respectively at the same time, it is recognized that the valve assembly 800' can be in the second configuration with only one of the first channel 623' or the third channel 601' operating. For example, in the second configuration, the first channel 623' may be providing suction while the third channel 601' is non-operational (e.g., by controlling the second tube 682'). In another example, the third channel 601' may be providing irrigation while the first channel 623' is not being utilized for suction (e.g., by controlling the first tube 681').

In some implementations, tubes 681', 682' can be used for suction and irrigation. In other implementations, tubes 681', 682' can be used to enable air/CO2 insufflation or an alternative fluid substance to flow through the cannula 620. In some implementations, the endoscope 600 may include one or more additional tubes similar to tubes 681', 682'. For example, the endoscope 600 may include three or more tubes. In this implementation, the cannula 620 may include one or more additional channels and/or cannula ports to fluidly communicate with the three or more tubes. In such an implementation, the valve assembly 800' may be configured to have three or more configuration. For example, the valve assembly 800' may be configured such that each channel in the cannula 620' can be configured for suction, irrigation, and air/CO2/fluid insufflation. In some implementations, each channel in the cannula 620' can be in a configuration for one of: suction, irrigation, and air/CO2/fluid insufflation simultaneously.

Including the valve assembly 800' in the optical cannula system 500' can provide a benefit of allowing the system operator to selectively alternate the function (e.g., suction or irrigation) of the first working channel 623' and the third channel 601' simultaneously. Advantageously, the changing between configurations can be achieved by the operator with one hand in some cases. For example, the valve handle 802' can be moved proximally and distally relative to the body 670' by the operator with one hand to change configuration while the operator's other hand supports the optical cannula system 500' via the body 670' for example. This arrangement beneficially allows the operator to perform a procedure without relying on support to change the configuration of the optical cannula system 500'. In one example, alternating the function of the channels 623', 601' can allow the operator to selectively clear a clogged channel 623', 601' or channel port (e.g., channel ports 602a', 602b'), which may be a result of occlusion related to tissue debris. Additionally, as either the first channel 623' or the third channel 601' can be selectively used for suction and irrigation, the operator can control and direct the irrigation and suction of the optical cannula system 500' with greater precision.

In some implementations, the cannula 620' can be removable from the body 670'. As such, an operator can select different cannulas 620' for the optical cannula system 500', depending on the desired features of the cannula 620'. For example, different cannulas 620' may have different lengths, geometries, dimensions, optical performance, compatibility with tools, and/or the like. For example, FIG. 40 shows an implementation of the cannula 620' that includes a curved distal end 621'. As shown in FIG. 40, the cannula 620' can include a transition or curved region 699' positioned along the length of the cannula 620' between the distal end 621' and the proximal end 622'. The curved region 699' is shown with lines between the other portions of the cannula 620' for illustrative purposes. In some implementations, the cannula 620' can be manufactured to comprise a single component including the curved region 699'. The curved region 699' can allow the distal end 621' to be axially offset from the remainder of the cannula 620'. For example, a central axis of the distal end 621' can be at a non-zero angle between 0 degrees and 90 degrees (e.g., between 5 degrees and 80 degrees, between 10 degrees and 70 degrees, between 15 degrees and 60 degrees, between 20 degrees and 50 degrees, between 25 degrees and 40 degrees, values between the foregoing, etc.) relative to a central axis of the proximal end 622'. In the illustrated example, the distal end 621' is at an angle of approximately 30 degrees relative to the proximal end 622'. In some cases, an angle of between 15 degrees and 45 degrees between the central axis of the distal end 621' and the proximal end 622' may be desirable.

Utilizing a cannula 620' with a curved distal end 621' in the optical cannula system 500' can provided certain benefits, depending on the implementation. For example, the curved design may allow the operator to reach areas that would be challenging to access with a straight cannula. In one example, a curved design can allow for improved visualizing aspects of the posterior knee compartment, intercondylar notch, etc. For example, a 30-degree curved cannula, such as the cannula 620' shown in FIG. 40, would more closely mimic the angled view from a 30-degree straight arthroscope and thus be more familiar to the operator. In another example, a curved cannula would allow for safer passage through and around tissue as the curved cannula can better follow the contour of a bone, cartilage, tendon, or ligament in order to see and work around or behind a bend without the need to overly retract tissue as would generally be required with an angled straight endoscope. A surgeon working through a curved cannula could then operate directly on tissue in an otherwise difficult to access area without the need to create a separate operative portal for visualization. Accordingly, the curved design can help avoid unnecessary contact with surrounding tissue and provide for improved viewing during use.

Figure 41A:
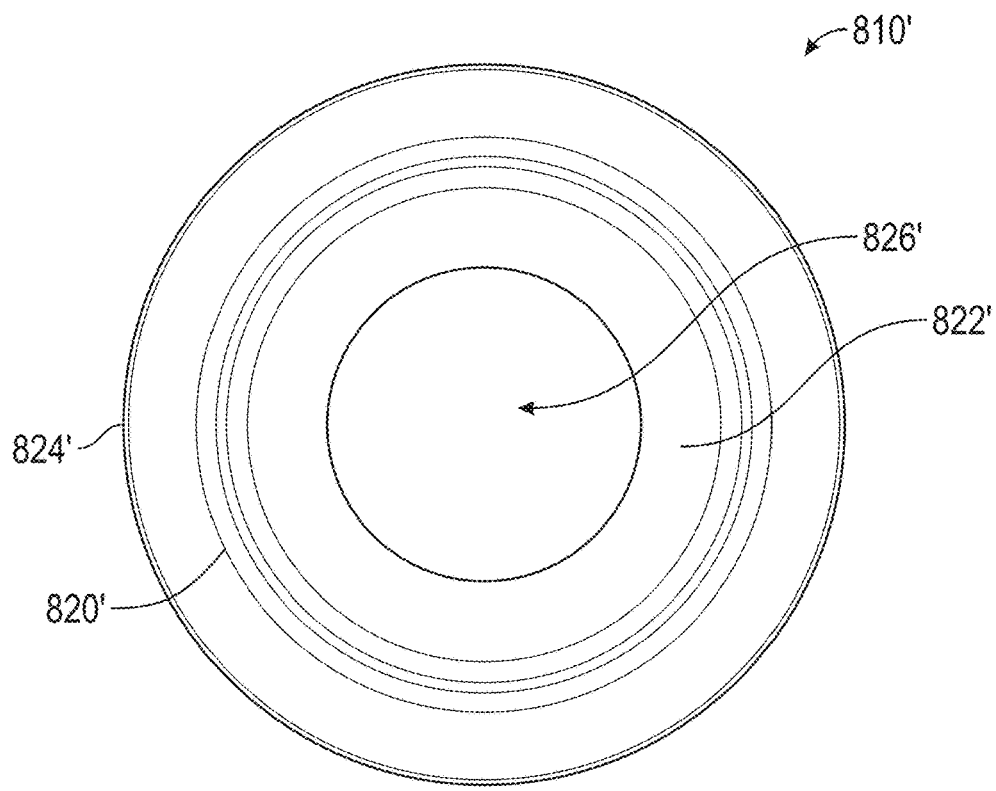
FIGS. 41A-41D show various views of seals that can be used in the endoscope of FIG. 33, in accordance with implementations of the disclosure.
Figures 41B, 41C:
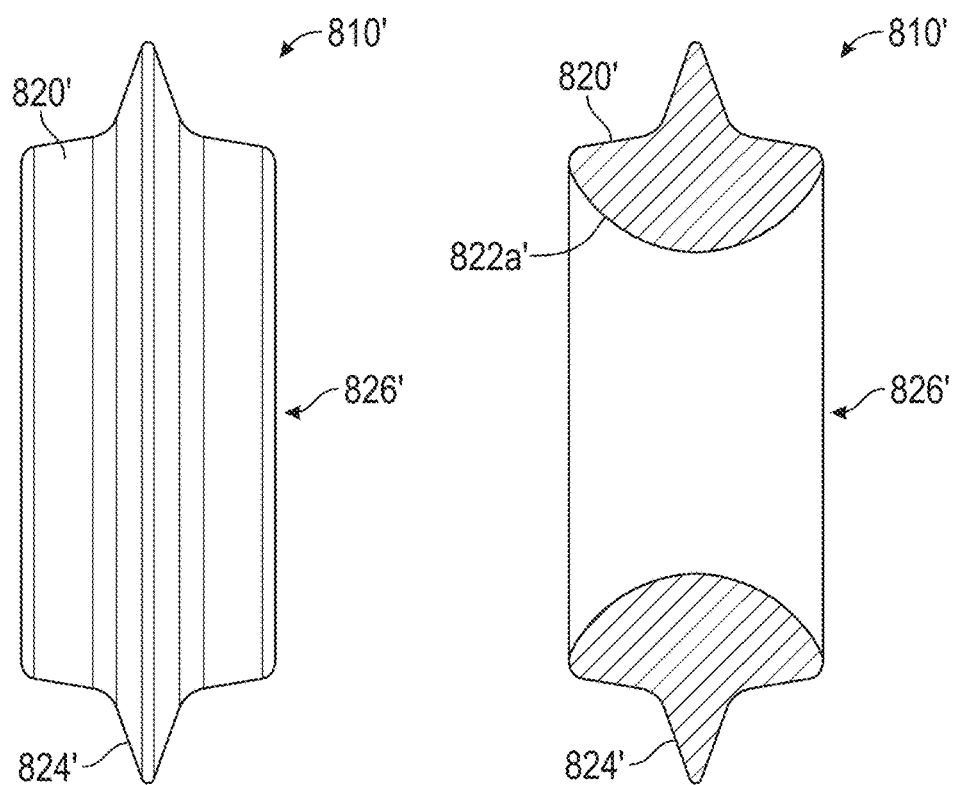
Figure 41D:
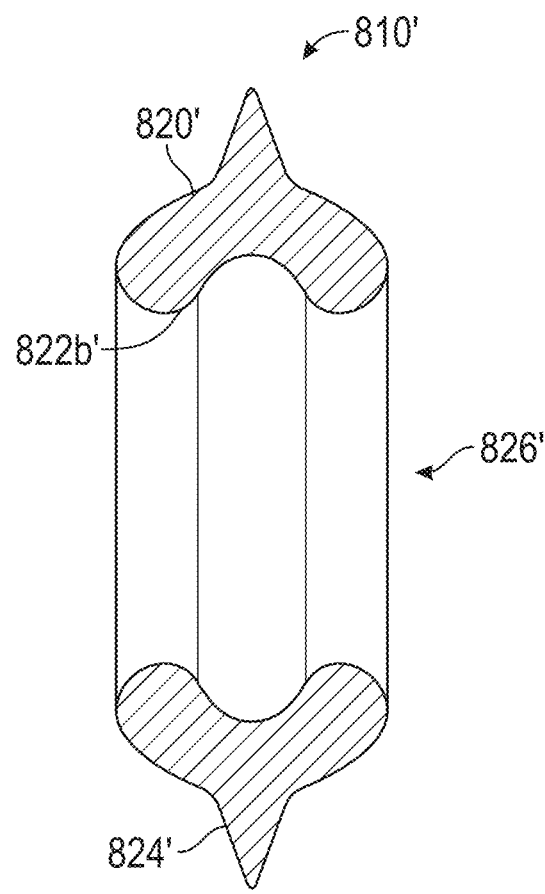

FIG. 41A-41D illustrate various views of example implementations of a seal 810' that can be utilized in the spool valve 806' of the optical cannula system 500'. FIG. 41C shows a cross-sectional view of the seal 810' with an inner surface 822a' having a first shape and FIG. 41D shows a cross-sectional view of the seal 810' with an inner surface 822b' having a second shape (collectively referred to as the "inner surface 822"). The seal 810' can include an outer surface 820' and the inner surface 822'. The outer surface 820' can include a circumferential ridge 824'. The circumferential ridge 824' can extend outwardly from a central axis of the 810'. The circumferential ridge 824' can be tapered. The inner surface 822' can define a central opening 826' extending axially through the seal 810'. The central opening 826' can be configured to receive a shaft, such as the valve shaft 808' of the spool valve 806', and to seal against the shaft. The inner surface 822' can taper or curve inwardly towards the central opening 826'. As shown in the section view of FIG. 41C, the inner surface 822a' can have a rocker shape, in a first implementation. As shown in the section view of FIG. 41D, in a second implementation, the inner surface 822b' may be arched shaped around the central opening 826'. In this configuration, the inner surface 822b' may not taper towards the central opening 826'.

The circumferential ridge 824' can be configured to have a larger outer diameter than an inner diameter of a channel (e.g., the second channel 646' of the harness block 640' of FIG. 38B) the seal 810' (and associated shaft) are received in. As such, the circumferential ridge 824' can be at least partially compressed inwardly during operation. The seal 810' can be configured to maintain a consistent fluid seal against the shaft and the channel during axial motion (e.g., along the axis of the channel). As the shaft moves relative to the channel, or vice-versa, the circumferential ridge 824' can be configured to move axially back and forth relative to the outer surface 820' while maintaining the seal. For example, the circumferential ridge 824' can move like a windshield wiper against the inner surface of the channel during axial movement relative to the outer surface 820'. The shape of the inner surface 822' (e.g., rocker bottom or arched) can facilitate the movement of the circumferential ridge 824'. As such, the seal 810' can act as a "self-lubricating" seal because the circumferential ridge 824' allows for axial movement against the inner surface of the channel, even in the absence of lubrication. Accordingly, the seal 810' can be ideal for applications where axial movement is required and lubrication is undesirable.

The shape of the inner surface 822' of the seal 810' can be selected for particular applications, with the seals 810' of FIGS. 41C and 41D each providing unique benefits. In some implementations, an arched-shaped inner surface 822b' can provide or allow for tighter tolerances. For example, the arched nature of the seal 810' when configured as shown in FIG. 41D can allow for easier compressibility of the seal 810' during axial motion. Easier compressibility can provide a benefit of decreased surface tension or friction during axial movement. Accordingly, when the seal 810' of FIG. 41D is utilized in the valve assembly 800', the back and forth movement of the of the valve handle 802' may be smoother because of the decreased friction between the seals 810' and the inner wall of the second channel 646' of the harness block 640'. In some implementations, the rocker-shaped inner surface 822a' of the seal 810' of FIG. 41C can provide for improved sealing under increased fluid pressure compared to an arched-shaped inner surface 822*b*'. Accordingly, the seal 810' of FIG. 41C may provide benefits when high fluid pressure is required.

Figure 42A:
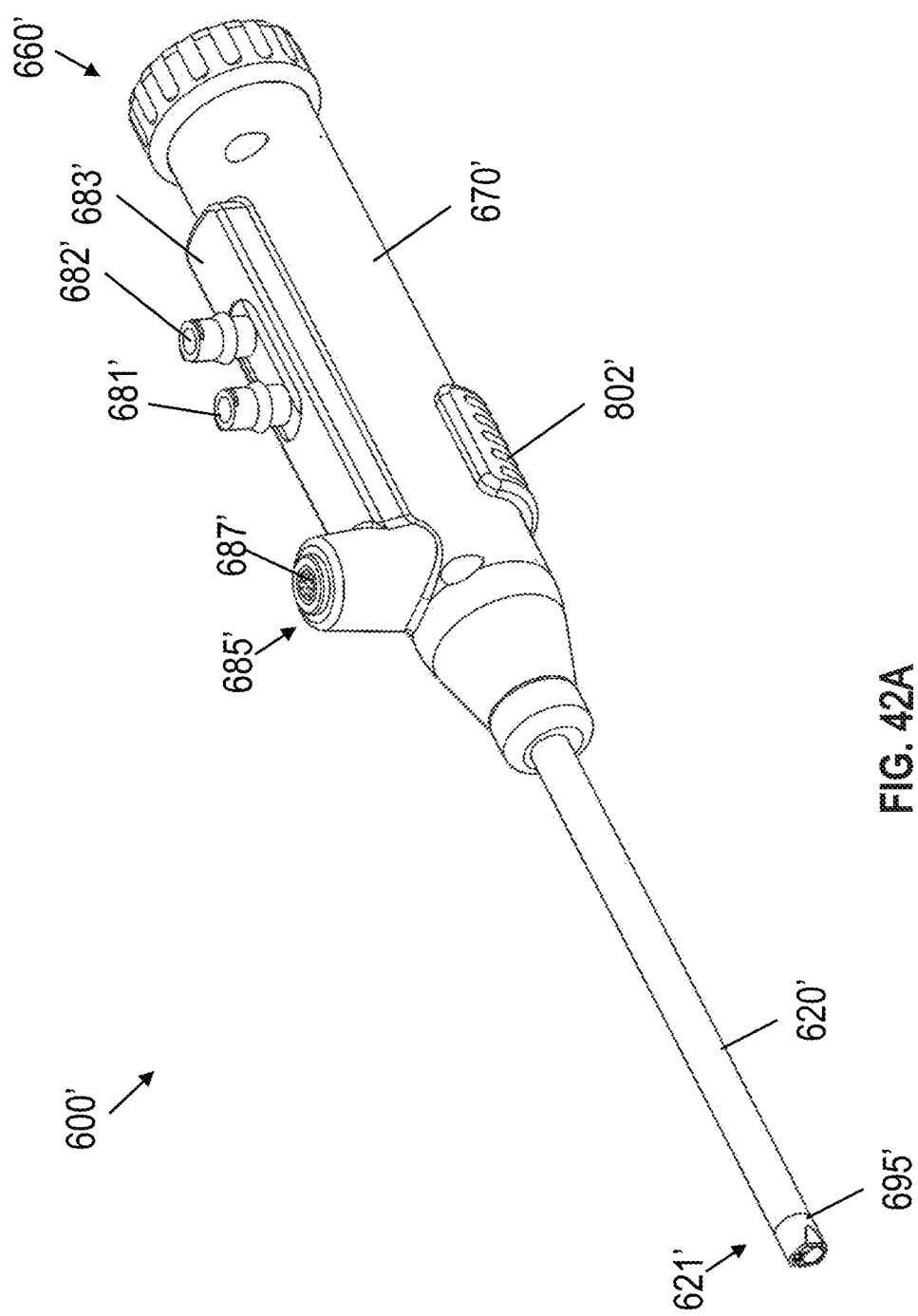
FIGS. 42A and 42B show a perspective view and a perspective section view respectively of an implementation of the endoscope of FIG. 33 configured for use with a removable electrical cable.
Figure 42B:
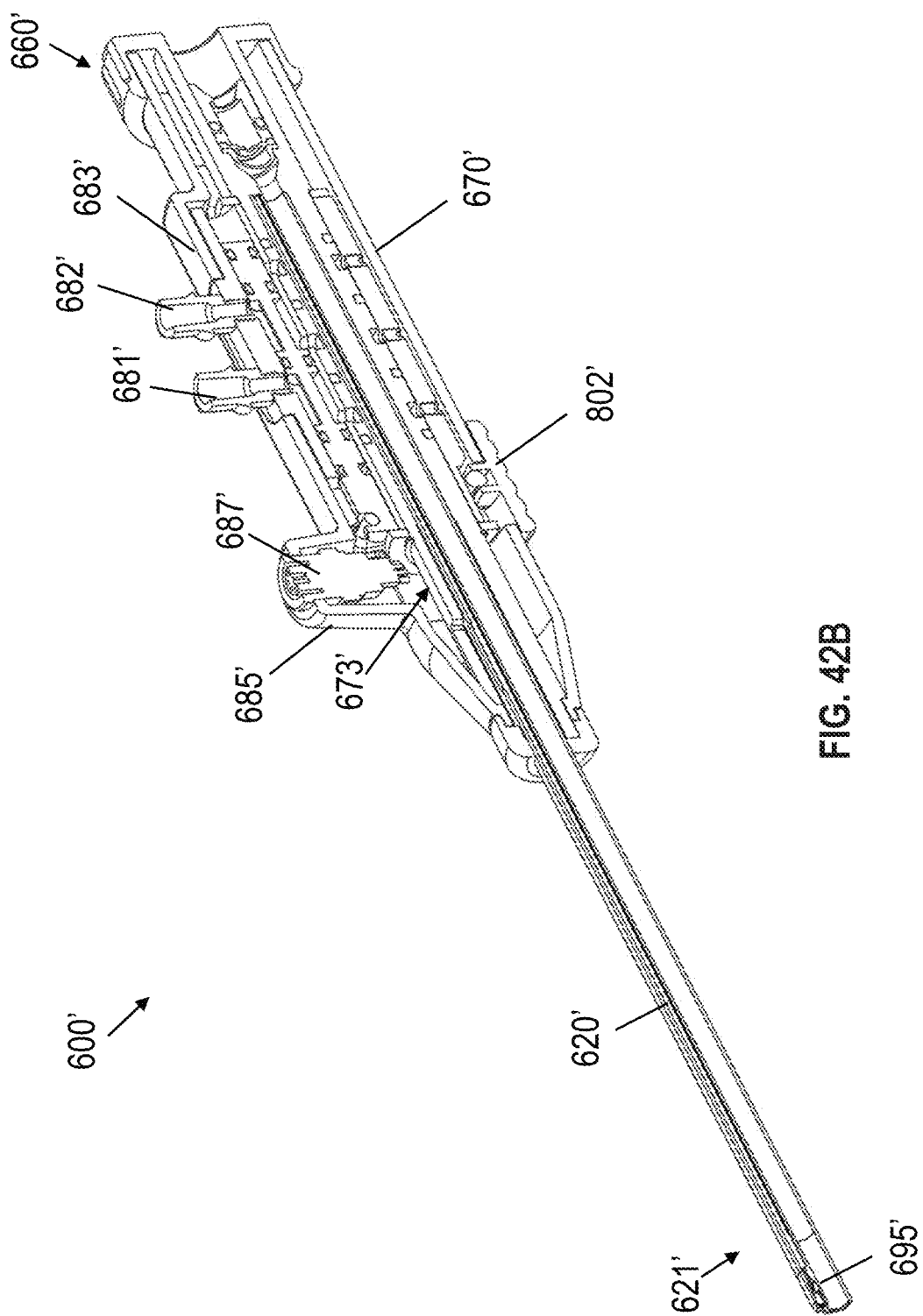

FIGS. 42A and 42B show a perspective view and a perspective section view respectively of an implementation of the endoscope 600' configured for use with a removable electrical cable. The endoscope 600' of FIGS. 42A and 42B can include an electrical coupler 687'. The body 670' can include an electrical entry hub 685' configured to house the electrical coupler 687'. The electrical coupler 687' can be configured to electrically, and in some instances magnetically, connect with an external electrical cable (not shown). For example, an external coupler of the external electrical cable can electrically and mechanically connect to the electrical coupler 687'. The electrical coupler 687' can be disposed within the electrical entry hub 685' and can at least partially extend into the body 670'. The electrical coupler 687' can be electrically connected to a camera signal wire (not shown). The camera signal wire may be electrically connected to the camera assembly 690', such as the one or more camera chips 691', the light sources 692', and/or the like, and may be positioned within the third channel 624'.

Having the external electrical cable configured to be removably connected to endoscope 600' (e.g., via the electrical coupler 687' in the electrical entry hub 685') can provide advantages, such as facilitating transportation and sterilization of the handle 670' with the external electrical cable detached. In another example, such a configuration can allow the endoscope 600' be independently maneuverable before connecting the external electrical cable.

The particular implementations disclosed above are illustrative only, as the application may be modified and practiced in different but equivalent manners apparent to those skilled in the art having the benefit of the teachings herein. It is therefore evident that the particular implementations disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

Additional Embodiments

Clause 1. An optical cannula system, comprising: a cannula, comprising: a proximal portion; a distal end; an axis extending between the proximal portion and the distal end; an outer cannula wall defining an interior space extending along the axis; an inner cannula wall within the outer cannula wall extending along the axis, the inner cannula wall dividing the interior space into a first channel and a second channel; a body configured to receive the proximal portion of the cannula; a first camera chip positioned at the distal end within the first channel; wherein the cannula is rotatable within body.

Clause 2. The optical cannula system of clause 1, further comprising: a harness, comprising: an inner surface disposed about the proximal portion of the cannula; a first circumferential seal disposed between the outer cannula wall and the inner surface of the harness; a second circumferential seal disposed between the outer cannula wall and the inner surface of the harness, the second circumferential seal spaced from the first circumferential seal to define a first fluid channel between the outer cannula wall and the inner surface; and a first harness port in fluid communication with the first fluid channel; and a first cannula port disposed through the outer cannula wall into the interior space; wherein first fluid channel is in fluid communication with the interior space through the first cannula port.

Clause 3. The optical cannula system of clause 2, the harness further comprising: a third circumferential seal disposed between the outer cannula wall and the inner surface of the harness, the third circumferential seal spaced from the second circumferential seal to define a second fluid channel between the outer cannula wall and the inner surface; and a second harness port in fluid communication with the second fluid channel; and a second cannula port disposed through the outer cannula wall into the interior space; wherein second fluid channel is in fluid communication with the interior space through the second cannula port.

Clause 4. The optical cannula system of clauses 3, wherein the first and second fluid channels are in fluid communication with the respective first and second cannula ports during rotation of the cannula relative to the harness.

Clause 5. The optical cannula system of clauses 4, wherein: the harness is rotationally fixed within the body; and the first and second cannula ports are in fluid communication with respective first and second hoses through the first and second fluid channels and the first and second harness ports.

Clause 6. The optical cannula system of clauses 5, wherein: the harness includes a harness block, the harness block comprising: a central aperture defined by the inner wall; and the first and second harness ports; wherein the harness block is rotationally fixed within the body.

Clause 7. The optical cannula system of clause 6, further comprising: an insertion portion attached with a rotation mechanism, the insertion portion positioned between the outer cannula wall and the first, second and third circumferential seals of the harness such that the first and second fluid channels are positioned between an outer wall of the insertion portion and the inner wall of the harness block; wherein the insertion portion includes first and second insertion portion ports aligned with the respective first and second fluid channels, and the first and second cannula ports, are in fluid communication with the first and second hoses during rotation of the cannula relative to the harness through the first and second fluid channels, the first and second harness ports, and the first and second insertion portion ports.

Clause 8. The optical cannula system of clause 7, wherein the insertion portion is attached with a dial of the rotation mechanism and configured to rotate the cannula relative to the body.

Clause 9. The optical cannula system of clauses 5, wherein the first and second hoses depart the body in a parallel configuration.

Clause 10. The optical cannula system of clauses 5, wherein the first hose is an irrigation hose and the second hose is a suction hose.

Clause 11. The optical cannula system of clauses 10, wherein the first and second cannula ports are in fluid communication with the second channel of the cannula.

Clause 12. The optical cannula system of clauses 11, wherein an instrument shaft is disposed within the second channel and divides a first side of the second channel from a second side of the second channel, the first cannula port is in communication with the first side of the second channel and the second cannula port is in communication with the second side of the second channel.

Clause 13. The optical cannula system of clauses 10, wherein the first and second cannula ports are in fluid communication with the first channel of the cannula.

Clause 14. The optical cannula system of clauses 10, wherein the first cannula port is in communication with the first channel of the cannula and the second cannula port is in communication with the second channel of the cannula.

Clause 15. The optical cannula system of clause 2, further comprising: a camera signal wire within the first channel connected with the first camera chip, the camera signal wire being electrically connected with an electrical coupler by a service loop or electrical commutator; an external electrical cable including an external coupler configured to electrically connect with the electrical coupler; wherein the cannula, the first camera chip, the harness and any attached tubes, the external electrical cable, and the external coupler are removable from the body such that the body can be reusable.

Clause 16. The optical cannula system of clause 1, further comprising: a camera signal wire within the first channel connected with the first camera chip, the camera signal wire being electrically connected with an electronic control board within the body by a service loop or electrical commutator, the electronic control board coupled with an external electrical cable.

Clause 17. The optical cannula system of clause 1, further comprising: a turn dial engaged with the outer cannula wall and configured to transmit a torque to the cannula.

Clause 18. The optical cannula system of clause 1, further comprising: a tool, comprising: an instrument shaft configured to be inserted within the outer cannula; and a surgical tool at a distal end of the instrument shaft.

Clause 19. The optical cannula system of clause 18, wherein the instrument shaft includes an inner shaft and an outer shaft, a distal end of the inner shaft is coupled with the surgical tool, a proximal end of the inner shaft is coupled with a lever, and squeezing the lever actuates the surgical tool.

Clause 20. The optical cannula system of clause 19, wherein the lever is on the body.

Clause 21. The optical cannula system of clause 19, wherein the tool further comprises a grip portion attached with a proximal end the instrument shaft, the lever attached with the grip portion.

Clause 22. The optical cannula system of clause 21, wherein the tool further comprises: a catch coupled with the lever, wherein the outer shaft is coupled with the grip portion and the proximal end of the inner shaft is coupled with the catch such that squeezing the lever actuates the surgical tool.

Clause 23. The optical cannula system of clause 22, further comprising: an assembly sleeve including a first slot; the grip portion including a second slot; wherein alignment of the first slot with the second slot permits the assembly or disassembly of the outer shaft with the grip portion and the inner shaft with the catch and misalignment of the first slot with the second slot locks the outer shaft within the grip portion and the inner shaft within the catch.

Clause 24. The optical cannula system of clause 23, wherein the instrument shaft includes a collar and the grip portion includes a turn dial, the collar insertable within an aperture of the turn dial such that the instrument shaft rotates with the cannula.

Clause 25. The optical cannula system of clause 23, further comprising: an instrument seal disposed within the grip portion; wherein the instrument seal includes a central aperture aligned with the second channel of the cannula and configured to receive the instrument shaft.

Clause 26. The optical cannula system of clause 25, wherein the instrument seal is removable and reversible to accommodate either distal-to-proximal or proximal-to-distal loading of the instrument shaft.

Clause 27. The optical cannula system of clause 23, wherein rotation of the instrument shaft is independent of rotation of the cannula.

Clause 28. The optical cannula system of clause 27, wherein the instrument shaft is coupled with a first turn dial for rotating the surgical tool.

Clause 29. The optical cannula system of clause 1, further comprising: a second camera chip positioned at the distal end within the first channel, the first camera chip positioned on a first side of the first channel and the second camera chip positioned on a second side of the first channel.

Clause 30. The optical cannula system of clause 29, wherein the first and second camera chips are in a divergent orientation to provide different viewing angles.

Clause 31. The optical cannula system of clause 29, wherein images from the first and second camera chips digitally combined to create a panoramic field of view and images of the distal end of the cannula are digitally removed or reduced from combined panoramic field of view.

Clause 32. The optical cannula system of clause 1, further comprising: a light source at the distal end of the first channel.

Clause 33. The optical cannula system of clause 1, wherein the outer cannula wall of the cannula has a circular cross-sectional shape, the first channel has a crescent cross-sectional shape and the second channel has a circular cross-sectional shape.

Clause 34. The optical cannula system of clause 1, wherein the first channel has a rectangular or trapezoidal cross-sectional shape.

Clause 35. An optical cannula system, comprising: a reusable or disposable cannula; an outer turn dial; an endoscope handle; an irrigation/suction harness; an electrical coupler; and a camera chip within a distal tip of the cannula; wherein a proximal end of the cannula is received within the endoscope handle, the suction/irrigation harness is attached to the proximal end of the cannula, and the suction/irrigation harness is secured to the endoscope handle; wherein the outer turn dial is coupled with the cannula such that rotation of the outer turn dial causes the cannula to turn either clockwise or counterclockwise within the irrigation harness;

Clause 36. The optical cannula system of clause 35, further comprising: a first port within an outer cannula wall aligned with a first fluid channel within an interior circumference of the suction/irrigation harness; a second port within the outer cannula wall aligned with a second fluid channel within the interior circumference of the suction/irrigation harness; wherein the first and second fluid channels are separated by seals that maintain a watertight seal with the outer cannula wall and the first and second ports maintain communication with the respective first and second fluid channels during rotation of the cannula relative to the irrigation/suction harness.

Clause 37. The optical cannula system of clause 36, wherein the first port drains a first fluid channel within the cannula and the second port drains a second fluid channel within the cannula.

Clause 38. The optical cannula system of clause 36 or 37, wherein the first port is offset longitudinally and circumferentially from the second port along the outer cannula wall.

Clause 39. The optical cannula system of clause 36 or 37, further comprising suction and irrigation tubes and an electrical cable that depart the endoscope handle in a parallel, streamlined orientation.

Clause 40. The optical cannula system of clause 39, wherein the suction and irrigation tubes pass through a cutout in the endoscope handle to couple with the irrigation/suction harness.

Clause 41. The optical cannula system of clause 36 or 37, further comprising: a lever is attached to the endoscope handle; an instrument shaft including an inner instrument shaft within an outer instrument; and a tool tip attached to an end of the instrument shaft; wherein the lever is coupled with the endoscope handle and the inner shaft such that movement of the lever against the endoscope handle causes the inner instrument shaft to move in a direction opposite from the outer instrument shaft and causes mechanized movement of the tool tip.

Clause 42. The optical cannula system of clause 41, further comprising: a removable locking key that integrates with a proximal end of the instrument shaft and couples the inner instrument shaft with at least on endoscope handle lever extension.

Clause 43. The optical cannula system of clause 41, further comprising: a shaft turn dial coupled with the endoscope handle configured to independently rotate the instrument shaft relative to the cannula.

Clause 44. The optical cannula system of clause 36 or 37, wherein the endoscope handle includes an elongate semicircular indention on a top surface thereof for receiving the cannula.

Clause 45. The optical cannula system of clause 36 or 37, wherein the outer turn dial includes a collar extension that snaps within a molded indentation within the endoscope handle.

Clause 46. The optical cannula system of clause 36 or 37, further comprising: an optical light fiber; wherein borders of the first fluid channel that drains at the first port and the second fluid channel that drains at the second port are formed by an instrument working channel internally, the outer cannula wall externally, and the camera chip and optical light fiber centrally.

Clause 47. The optical cannula system of clause 36 or 37, further comprising: an electrical wire carrying a camera signal along the camera from the camera chip in the distal tip of the cannula through a length of the cannula to interface with the electrical coupler.

Clause 48. The optical cannula system of clause 47, further comprising a circumferential contact lead or band about the outer cannula wall to allow free rotation of the cannula while carrying the camera signal to interface with the electrical coupler.

Clause 49. The optical cannula system of clause 47, further comprising a slack wire to connect the electrical coupler with the electrical wire.

Clause 50. The optical cannula system of clause 36 or 37, wherein the cannula and any instrument shaft, the camera chip, the irrigation/suction harness and any attached tube, and the electrical coupler and any attached electrical cable are removable from the endoscope handle such that the endoscope handle can be reusable.

Clause 51. An optical cannula system, comprising: a cannula, comprising: a proximal portion; a distal end; an axis extending between the proximal portion and the distal end; an outer cannula wall defining an interior space extending along the axis; one or more inner cannula walls within the outer cannula wall extending along the axis, the one or more inner cannula walls dividing the interior space into a first channel, a second channel, and a third channel; and a body configured to receive the proximal portion of the cannula; wherein the cannula is rotatable within the body.

Clause 52. The optical cannula system of clause 51, further comprising an optical cap comprising a camera chip, the optical cap configured to be coupled to the distal end of the cannula.

Clause 53. The optical cannula system of clause 51 or clause 52, wherein the cannula further comprises: a first cannula port disposed through the outer cannula wall into the second channel; a second cannula port disposed through the outer cannula wall into the second channel; and a third cannula port disposed through the outer cannula wall into the third channel.

Clause 54. The optical cannula system of clause 53, further comprising: a harness, comprising: a first harness port; and a second harness port; and a valve assembly comprising: a handle; and a valve shaft, the valve assembly having a first configuration and a second configuration, the handle configured to move the valve shaft between the first configuration and the second configuration; wherein in the first configuration, the first harness port is in fluid communication with the first cannula port and the second harness port is in fluid communication with the third cannula port, wherein in the second configuration, the first harness port is in fluid communication with the third cannula port and the second harness port is in fluid communication with the second cannula port.

Clause 55. The optical cannula system of clause 54, wherein the second channel and the third channel are in fluid communication with the respective first harness port and second harness port during rotation of the cannula relative to the harness.

Clause 56. The optical cannula system of clause 54 or clause 55, wherein the first harness port is configured for irrigation and the second harness port is configured for suction.

Clause 57. The optical cannula system of clause 54 or clause 55, wherein the first harness port is configured for suction and the second harness port is configured for irrigation.

Clause 58. The optical cannula system of any of clauses 51 to 57, wherein the second channel comprises a first portion configured to receive a shaft of a tool and a second portion configured to promote fluid communication around the first portion and the shaft of the tool.

Clause 59. The optical cannula system of any of clauses 54 to 58, further comprising: a camera signal wire within the first channel connected with the camera chip, the camera signal wire being electrically connected with an electrical coupler by a service loop or electrical commutator; and an external electrical cable including an external coupler configured to electrically connect with the electrical coupler.

Clause 60. The optical cannula system of clause 59, wherein the cannula, the camera chip, the harness and any attached tubes, the external electrical cable, and the external coupler are removable from the body such that the body can be reusable.

Clause 61. An optical cannula system, comprising: a cannula, comprising: a proximal portion; a distal end; an axis extending between the proximal portion and the distal end; an outer cannula wall defining an interior space extending along the axis; and one or more inner cannula walls within the outer cannula wall extending along the axis, the one or more inner cannula walls dividing the interior space into a first channel and a second channel; a body configured to receive the proximal portion of the cannula; a first tube extending from the body; a second tube extending from the body; and a valve assembly connected to the body, the valve assembly having a first configuration in which the first tube is in fluid communication with the first channel and the second tube is in fluid communication with the second channel, the valve assembly having a second configuration in which the first tube is in fluid communication with the second channel and the second tube is in fluid communication with the first channel.

Clause 62. The optical cannula system of clause 61, wherein in the first configuration, the first tube is not in fluid communication with the second channel, wherein in the second configuration, the first tube is not in fluid communication with the first channel.

Clause 63. The optical cannula system of clause 61 or clause 62, wherein in the first configuration, the second tube is not in fluid communication with the first channel, wherein in the second configuration, the second tube is not in fluid communication with the second channel.

Clause 64. The optical cannula system of any of clauses 61 to 63, wherein the cannula is rotatable within the body.

Clause 65. The optical cannula system of any of clauses 61 to 64, wherein the valve assembly comprises: a handle moveable relative to the body, the handle configured to move the valve assembly between the first configuration and the second configuration; and a valve shaft connected to the handle, in the first configuration, the valve shaft configured to allow fluid communication between the first tube and the first channel and between the second tube and the second channel, and in the second configuration, the valve shaft configured to allow fluid communication between the first tube and the second channel and between the second tube and the first channel.

Clause 66. The optical cannula system of clause 65, wherein the valve assembly further comprises a plurality of valve seals disposed on the valve shaft, the plurality of valve seals configured to seal against the valve shaft under axial movement.

Clause 67. The optical cannula system of clause 65, wherein the handle is configured to be moved relative to the body using one hand.

Clause 68. The optical cannula system of any of clauses 61 to 67, wherein: the first tube is configured for irrigation and the second tube is configured for suction; or the first tube is configured for suction and the second tube is configured for irrigation.

Clause 69. The optical cannula system of any of clauses 61 to 68, wherein the first tube forms a distal end of an irrigation hose and the second tube forms a distal end of a suction hose, the irrigation hose and the suction hose configured to be removably connected to the body.

Clause 70. The optical cannula system of any of clauses 61 to 69, wherein a first total cross-sectional area of the first channel is larger than a second total cross-sectional area of the second channel.

Clause 71. The optical cannula system of any of clauses 61 to 70, wherein the first channel comprises a main channel portion and a side channel portion extending from the main channel portion, the one or more inner cannula walls at least partially defining the main channel portion and the side channel portion, the main channel portion configured to receive a shaft of a tool, the side channel portion configured to allow fluid communication around the main channel portion and the shaft of the tool.

Clause 72. The optical cannula system of clause 71, wherein a third total cross-sectional area of the side channel portion is larger than the second total cross-sectional area of the second channel.

Clause 73. The optical cannula system of any of clauses 61 to 72, wherein the cannula further comprises a second channel port, the second channel port extending through the outer cannula wall near the distal end and into the second channel, the second channel port configured to allow fluid communication between an environment external to the cannula and the second channel.

Clause 74. The optical cannula system of clause 73, wherein the second channel port is located on an opposite side of the cannula than the side channel portion.

Clause 75. The optical cannula system of any of clauses 61 to 74, wherein the one or more inner cannula walls further divide the interior space of the outer cannula wall into a third channel.

Clause 76. The optical cannula system of any of clauses 61 to 75, further comprising an optical cap housing a camera chip, the optical cap configured to be connected to the distal end of the cannula.

Clause 77. The optical cannula system of clause 76, wherein the optical cap further comprises a central opening configured to be at least partially aligned with the first channel, the central opening allowing fluid communication between the first channel and an external environment through the optical cap.

Clause 78. The optical cannula system of clause 76 or clause 77, wherein the optical cap further comprise a side port extending through a side wall thereof, the side port configured to allow fluid communication between the second channel and an external environment through the optical cap.

Clause 79. The optical cannula system of clause 78, wherein the side port extends through a recessed portion of the optical cap.

Clause 80. The optical cannula system of any of clauses 76 to 79, wherein the optical cap further comprises one or more tapered portions, the one or more tapered portions at least partially defining a distally narrowing outer surface of the optical cap.

Clause 81. The optical cannula system of any of clauses 76 to 80, further comprising a second side port extending through a side wall thereof, the second side port configured to allow fluid communication between the first channel and an external environment through the optical cap.

Clause 82. The optical cannula system of clause 81, wherein the side port and the second side port are located on substantially opposite sides of the optical cap.

Clause 83. The optical cannula system of any of clauses 76 to 82, further comprising: a camera signal wire positioned within the third channel, the camera signal wire electrically connected with the camera chip, the camera signal wire being electrically connected with an electrical coupler; and an external electrical cable including an external coupler configured to electrically connect with the electrical coupler.

Clause 84. The optical cannula system of clause 83, wherein the cannula, the camera chip, the first tube, the second tube, the external electrical cable, and the external coupler are removable from the body such that the body can be reusable.

Clause 85. The optical cannula system of any of clauses 76 to 84, further comprising a second camera chip housed within the optical cap, the camera chip positioned beside the second camera chip.

Clause 86. The optical cannula system of clause 85, wherein the camera chip and the second camera chip are in different positions to provide different viewing angles.

Clause 87. The optical cannula system of clause 85, wherein images from the camera chip and the second camera chip are digitally combined to create a panoramic field of view and images of the optical cap and/or the distal end of the cannula are digitally removed or reduced from the panoramic field of view.

Clause 88. The optical cannula system of any of clauses 76 to 87, wherein the optical cap houses one or more light sources, the one or more light sources electrically connected to the camera signal wire or one or more electrical wires.

Clause 89. The optical cannula system of any of clauses 61 to 88, wherein the cannula further comprises: a first cannula port disposed through the outer cannula wall into the first channel; a second cannula port disposed through the outer cannula wall into the first channel; and a third cannula port disposed through the outer cannula wall into the second channel.

Clause 90. The optical cannula system of clause 89, further comprising a harness assembly comprising a first harness port and a second harness port, the first harness port aligned with the first tube, the second harness port aligned with the second tube, wherein in the first configuration, the first harness port is in fluid communication with the first cannula port and the second harness port is in fluid communication with the third cannula port, wherein in the second configuration, the first harness port is in fluid communication with the third cannula port and the second harness port is in fluid communication with the second cannula port.

Clause 91. The optical cannula system of clause 90, wherein the first channel and the second channel are in fluid communication with the respective first harness port and second harness port during rotation of the cannula relative to the harness assembly.

Clause 92. The optical cannula system of clause 90 or clause 91, wherein the harness assembly further comprises: an inner surface disposed about the proximal portion of the cannula; and a plurality of circumferential seals disposed between the outer cannula wall and the inner surface to define fluid channels between the outer cannula wall and the inner surface.

Clause 93. The optical cannula system of clause 92, wherein the harness assembly further comprises: a harness block; a central channel extending through the harness block and defined by the inner surface; the first harness port; and the second harness port, the first harness port and the second harness port extending at least partially through the harness block to define fluid channels through the harness block to the central channel, wherein the harness block is rotationally fixed within the body.

Clause 94. The optical cannula system of clause 93, wherein the harness assembly further comprises a second channel extending through the harness block, an internal wall of the harness block at least partially separating the second channel from the central channel, wherein the valve shaft is at least partially disposed within the second channel.

Clause 95. The optical cannula system of clause 94, wherein the internal wall of the harness block comprises a plurality of internal apertures configured to allow fluid communication between the second channel and the central channel.

Clause 96. The optical cannula system of clause 94 or clause 95, wherein the first harness port and the second harness port define fluid passageways into the second channel.

Clause 97. The optical cannula system of clause 95 or clause 96, wherein a position of the valve shaft within the second channel defines which internal apertures of the plurality of internal apertures the first harness port and the second harness port are in fluid communication with.

Clause 98. The optical cannula system of any of clauses 95 to 97, wherein in the first configuration, the first harness port is in fluid communication with a first aperture of the plurality of internal apertures and the second harness port is in fluid communication with a third aperture of the plurality of internal apertures, wherein in the second configuration, the first harness port is in fluid communication with the third aperture of the plurality of internal apertures and the second harness port is in fluid communication with a second aperture of the plurality of internal apertures.

Clause 99. The optical cannula system of any of clauses 92 to 98, further comprising a rotation assembly configured to control rotation of the cannula relative to the body, the rotation assembly comprising: a rotation handle configured to be accessible outside of the body; and an insertion portion connected to the rotation handle, the insertion portion extending at least partially into the body, wherein the insertion portion is positioned between the outer cannula wall and the plurality of circumferential seals.

Clause 100. The optical cannula system of any of clauses 61 to 99, wherein the first tube and the second tube extend from the body in a parallel configuration.

Clause 101. The optical cannula system of any of clauses 61 to 100, wherein the cannula further comprises a curved region between the distal end and the proximal portion such that a central axis of the distal end is at a non-zero angle relative to a central axis of the proximal portion.

Clause 102. The optical cannula system of clause 101, wherein the non-zero angle is between 15 degrees and 45 degrees.

Clause 103. An optical cannula system, comprising: a cannula, comprising: an outer cannula wall having a proximal portion and a distal end; a first channel within the outer cannula wall, the first channel configured for suction in a first configuration of the optical cannula system and configured for irrigation in a second configuration of the optical cannula system; a second channel within the outer cannula wall, the second channel configured for irrigation in the first configuration and suction in the second configuration; and one or more internal walls within the outer cannula wall, the one or more internal walls extending at least partially along a length of the outer cannula wall between the proximal portion and the distal end, the one or more internal walls at least partially defining the first channel and the second channel; and a body configured to receive the proximal portion of the cannula.

Clause 104. The optical cannula system of clause 103, further comprising: a first tube extending from the body; a second tube extending from the body; and a valve assembly connected to the body, the valve assembly configured to transition the optical cannula system between the first configuration and the second configuration.

Clause 105. The optical cannula system of clause 104, wherein in the first configuration, the first tube is not in fluid communication with the second channel, wherein in the second configuration, the first tube is not in fluid communication with the first channel.

Clause 106. The optical cannula system of clause 104 or clause 105, wherein in the first configuration, the second tube is not in fluid communication with the first channel, wherein in the second configuration, the second tube is not in fluid communication with the second channel.

Clause 107. The optical cannula system of any of clauses 103 to 106, wherein the cannula is rotatable within the body.

Clause 108. The optical cannula system of any of clauses 104 to 107, wherein the valve assembly comprises: a handle moveable relative to the body, the handle configured to move the optical cannula system between the first configuration and the second configuration; and a valve shaft connected to the handle, in the first configuration, the valve shaft configured to allow fluid communication between the first tube and the first channel and between the second tube and the second channel, and in the second configuration, the valve shaft configured to allow fluid communication between the first tube and the second channel and between the second tube and the first channel.

Clause 109. The optical cannula system of clause 108, wherein the valve assembly further comprises a plurality of valve seals disposed on the valve shaft, the plurality of valve seals configured to seal against the valve shaft under axial movement.

Clause 110. The optical cannula system of clause 109, wherein the plurality of valve seals are compressible.

Clause 111. The optical cannula system of clause 109 or clause 110, wherein each valve seal of the plurality of valve seals has an inner surface having a rocker bottom shape.

Clause 112. The optical cannula system of clause 109 or clause 110, wherein each valve seal of the plurality of valve seals has an inner surface having an arch shape.

Clause 113. The optical cannula system of any of clauses 108 to 112, wherein the handle is configured to be moved relative to the body using one hand.

Clause 114. The optical cannula system of any of clauses 104 to 113, wherein the first tube forms a distal end of an irrigation hose and the second tube forms a distal end of a suction hose, the irrigation hose and the suction hose configured to be removably connected to the body.

Clause 115. The optical cannula system of any of clauses 103 to 114, wherein a first total cross-sectional area of the first channel is larger than a second total cross-sectional area of the second channel.

Clause 116. The optical cannula system of any of clauses 103 to 115, wherein the first channel comprises a main channel portion and a side channel portion extending from the main channel portion, the one or more internal walls at least partially defining the main channel portion and the side channel portion, the main channel portion configured to receive a shaft of a tool, the side channel portion configured to allow fluid communication around the main channel portion and the shaft of the tool.

Clause 117. The optical cannula system of clause 116, wherein a third total cross-sectional area of the side channel portion is larger than the second total cross-sectional area of the second channel.

Clause 118. The optical cannula system of any of clauses 103 to 117, wherein the cannula further comprises a second channel port, the second channel port extending through the outer cannula wall near the distal end and into the second channel, the second channel port configured to allow fluid communication between an environment external to the cannula and the second channel.

Clause 119. The optical cannula system of clause 118, wherein the second channel port is located on an opposite side of the cannula than the side channel portion.

Clause 120. The optical cannula system of any of clauses 103 to 119, further comprising a third channel, the one or more internal walls at least partially defining the third channel.

Clause 121. The optical cannula system of any of clauses 103 to 120, further comprising an optical cap housing a camera chip, the optical cap configured to be connected to the distal end of the cannula.

Clause 122. The optical cannula system of clause 121, wherein the optical cap further comprises a central opening configured to be at least partially aligned with the first channel, the central opening allowing fluid communication between the first channel and an external environment through the optical cap.

Clause 123. The optical cannula system of clause 121 or clause 122, wherein the optical cap further comprise a side port extending through a side wall thereof, the side port configured to allow fluid communication between the second channel and an external environment through the optical cap.

Clause 124. The optical cannula system of clause 123, wherein the side port extends through a recessed portion of the optical cap.

Clause 125. The optical cannula system of any of clauses 121 to 124, wherein the optical cap further comprises one or more tapered portions, the one or more tapered portions at least partially defining a distally narrowing outer surface of the optical cap.

Clause 126. The optical cannula system of any of clauses 121 to 125, further comprising a second side port extending through a side wall thereof, the second side port configured to allow fluid communication between the first channel and an external environment through the optical cap.

Clause 127. The optical cannula system of clause 126, wherein the side port and the second side port are located on substantially opposite sides of the optical cap.

Clause 128. The optical cannula system of any of clauses 121 to 127, further comprising: a camera signal wire positioned within the third channel, the camera signal wire electrically connected with the camera chip, the camera signal wire being electrically connected with an electrical coupler; and an external electrical cable including an external coupler configured to electrically connect with the electrical coupler.

Clause 129. The optical cannula system of clause 128, wherein the cannula, the camera chip, the first tube, the second tube, the external electrical cable, and/or the external coupler are removable from the body such that the body can be reusable.

Clause 130. The optical cannula system of any of clauses 121 to 129, further comprising a second camera chip housed within the optical cap, the camera chip positioned beside the second camera chip.

Clause 131. The optical cannula system of clause 130, wherein the camera chip and the second camera chip are in different positions to provide different viewing angles.

Clause 132. The optical cannula system of clause 130, wherein images from the camera chip and the second camera chip are digitally combined to create a panoramic field of view and images of the optical cap and/or the distal end of the cannula are digitally removed or reduced from the combined panoramic field of view.

Clause 133. The optical cannula system of any of clauses 121 to 132, wherein the optical cap houses one or more light sources.

Clause 134. The optical cannula system of any of clauses 103 to 133, wherein the cannula further comprises: a first cannula port disposed through the outer cannula wall into the first channel; a second cannula port disposed through the outer cannula wall into the first channel; and a third cannula port disposed through the outer cannula wall into the second channel.

Clause 135. The optical cannula system of clause 134, further comprising a harness assembly comprising a first harness port and a second harness port, the first harness port aligned with the first tube, the second harness port aligned with the second tube, wherein in the first configuration, the first harness port is in fluid communication with the first cannula port and the second harness port is in fluid communication with the third cannula port, wherein in the second configuration, the first harness port is in fluid communication with the third cannula port and the second harness port is in fluid communication with the second cannula port.

Clause 136. The optical cannula system of clause 135, wherein the first channel and the second channel are in fluid communication with the respective first harness port and second harness port during rotation of the cannula relative to the harness assembly.

Clause 137. The optical cannula system of clause 135 or clause 136, wherein the harness assembly comprises: an inner surface disposed about the proximal portion of the cannula; and a plurality of circumferential seals disposed between the outer cannula wall and the inner surface to define fluid channels between the outer cannula wall and the inner surface.

Clause 138. The optical cannula system of clause 137, wherein the harness assembly further comprises a harness block, the harness block comprising: a central channel defined by the inner surface; the first harness port; and the second harness port, wherein the harness block is rotationally fixed within the body.

Clause 139. The optical cannula system of clause 138, wherein the harness block further comprises a second channel, an internal wall of the harness block at least partially separating the second channel from the central channel, wherein the valve shaft is at least partially disposed within the second channel.

Clause 140. The optical cannula system of clause 139, wherein the internal wall of the harness block comprises a plurality of internal apertures configured to allow fluid communication between the second channel and the central channel.

Clause 141. The optical cannula system of clause 139 or clause 140, wherein the first harness port and the second harness port define fluid passageways into the second channel.

Clause 142. The optical cannula system of clause 140 or clause 141, wherein a position of the valve shaft within the second channel defines which internal apertures of the plurality of internal apertures the first harness port and the second harness port are in fluid communication with.

Clause 143. The optical cannula system of any of clauses 140 to 142, wherein in the first configuration, the first harness port is in fluid communication with a first aperture of the plurality of internal apertures and the second harness port is in fluid communication with a third aperture of the plurality of internal apertures, wherein in the second configuration, the first harness port is in fluid communication with the third aperture of the plurality of internal apertures and the second harness port is in fluid communication with a second aperture of the plurality of internal apertures.

Clause 144. The optical cannula system of any of clauses 137 to 143, further comprising a rotation mechanism configured to control rotation of the cannula relative to the body, the rotation mechanism comprising: a rotation handle configured to be accessible outside of the body; and an insertion portion connected to the rotation handle, the insertion portion extending at least partially into the body, wherein the insertion portion is positioned between the outer cannula wall and the plurality of circumferential seals.

Clause 145. The optical cannula system of any of clauses 104 to 144, wherein the first tube and the second tube extend from the body in a parallel configuration.

Clause 146. The optical cannula system of any of clauses 103 to 145, wherein the cannula further comprises a curved region between the distal end and the proximal portion such that a central axis of the distal end is at a non-zero angle relative to a central axis of the proximal portion.

Clause 147. The optical cannula system of clause 146, wherein the non-zero angle is between 15 degrees and 45 degrees.

Clause 148. The optical cannula system of any of clauses 61 to 102 or clauses 103 to 147, further comprising: a tool, comprising: an instrument shaft configured to be inserted within the first channel; and a surgical tool at a distal end of the instrument shaft.

Clause 149. The optical cannula system of clause 148, wherein the instrument shaft comprises an inner shaft and an outer shaft, a distal end of the inner shaft connected with the surgical tool, a proximal end of the inner shaft connected with a lever, wherein squeezing the lever actuates the surgical tool.

Clause 150. The optical cannula system of clause 149, wherein the lever is on the body.

Clause 151. The optical cannula system of clause 149, wherein the tool further comprises a grip portion attached with a proximal end the instrument shaft, the lever attached with the grip portion.

Clause 152. The optical cannula system of clause 151, wherein the tool further comprises: a catch connected with the lever, wherein the outer shaft is connected with the grip portion and the proximal end of the inner shaft is connected with the catch such that squeezing the lever actuates the surgical tool.

Clause 153. The optical cannula system of clause 152, further comprising: an assembly sleeve including a first slot; and the grip portion including a second slot, wherein alignment of the first slot with the second slot permits assembly or disassembly of the outer shaft with the grip portion and the inner shaft with the catch and wherein misalignment of the first slot with the second slot locks the outer shaft within the grip portion and the inner shaft within the catch.

Clause 154. The optical cannula system of clause 153, wherein the instrument shaft includes a collar, and the grip portion includes a turn dial, the collar insertable within an aperture of the turn dial such that the instrument shaft rotates with the cannula.

Clause 155. The optical cannula system of clause 153, further comprising: an instrument seal disposed within the grip portion; wherein the instrument seal includes a central aperture aligned with the second channel of the cannula and configured to receive the instrument shaft.

Clause 156. The optical cannula system of clause 155, wherein the instrument seal is removable and reversible to accommodate either distal-to-proximal or proximal-to-distal loading of the instrument shaft.

Clause 157. The optical cannula system of any of clauses 148 to 156, wherein rotation of the instrument shaft is independent of rotation of the cannula.

Clause 158. The optical cannula system of clause 157, wherein the instrument shaft is connected with a first turn dial for rotating the surgical tool.

Clause 159. An optical cannula system, comprising: a handle comprising: a body; a first port extending at least partially through the body, the first port configured to connect to a first hose; and a second port extending at least partially through the body, the second port configured to connect to a second hose; and a cannula, comprising: an outer cannula wall having a proximal portion and a distal end, the proximal portion configured to be disposed within the body; a first channel within the outer cannula wall, the first channel configured to be in fluid communication with the first port in a first configuration and the second port in a second configuration; and a second channel within the outer cannula wall, the second channel configured to be in fluid communication with the second port in the first configuration and the first port in the second configuration.

Clause 160. The optical cannula system of clause 159, further comprising any features of any of clauses 1-158.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

SUMMARY

Several illustrative examples of optical cannula systems have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of optical cannula systems and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

What is claimed is:

1. An optical cannula system, comprising:
   a cannula, comprising:
      a proximal portion;
      a distal end;
      an axis extending between the proximal portion and the distal end;
      an outer cannula wall defining an interior space extending along the axis;
      one or more inner cannula walls within the outer cannula wall extending along the axis, the one or more inner cannula walls dividing the interior space into a first channel and a second channel;
      a first cannula port disposed through the outer cannula wall into the first channel;
      a second cannula port disposed through the outer cannula wall into the first channel; and
      a third cannula port disposed through the outer cannula wall into the second channel;
   a body configured to receive the proximal portion of the cannula;
   a first tube extending from the body;
   a second tube extending from the body;
   a valve assembly connected to the body, the valve assembly having a first configuration in which the first tube is in fluid communication with the first channel and the second tube is in fluid communication with the second channel, the valve assembly having a second configuration in which the first tube is in fluid communication with the second channel and the second tube is in fluid communication with the first channel; and
   a harness assembly comprising a first harness port and a second harness port, the first harness port aligned with the first tube, the second harness port aligned with the second tube, wherein in the first configuration, the first harness port is in fluid communication with the first cannula port and the second harness port is in fluid communication with the third cannula port, wherein in the second configuration, the first harness port is in fluid communication with the third cannula port and the second harness port is in fluid communication with the second cannula port.

2. The optical cannula system of claim 1, wherein the valve assembly comprises:
   a handle moveable relative to the body, the handle configured to move the valve assembly between the first configuration and the second configuration; and
   a valve shaft connected to the handle, in the first configuration, the valve shaft configured to allow fluid communication between the first tube and the first channel and between the second tube and the second channel, and in the second configuration, the valve shaft configured to allow fluid communication between the first tube and the second channel and between the second tube and the first channel.

3. The optical cannula system of claim 2, wherein the valve assembly further comprises a plurality of valve seals disposed on the valve shaft, the plurality of valve seals configured to seal against the valve shaft under axial movement.

4. The optical cannula system of claim 1, wherein a first total cross-sectional area of the first channel is larger than a second total cross-sectional area of the second channel.

5. The optical cannula system of claim 1, wherein the first channel and the second channel are in fluid communication with the respective first harness port and second harness port during rotation of the cannula relative to the harness assembly.

6. The optical cannula system of claim 5, wherein the harness assembly further comprises:
   an inner surface disposed about the proximal portion of the cannula; and
   a plurality of circumferential seals disposed between the outer cannula wall and the inner surface to define fluid channels between the outer cannula wall and the inner surface.

7. The optical cannula system of claim 6, wherein the harness assembly further comprises:
   a harness block;
   a central channel extending through the harness block and defined by the inner surface;
   the first harness port; and
   the second harness port, the first harness port and the second harness port extending at least partially through the harness block to define fluid channels through the harness block to the central channel,
   wherein the harness block is rotationally fixed within the body.

8. The optical cannula system of claim 7, wherein the harness assembly further comprises a second channel extending through the harness block, an internal wall of the harness block at least partially separating the second channel from the central channel, wherein a valve shaft of the valve assembly is at least partially disposed within the second channel.

9. The optical cannula system of claim 8, wherein the first harness port and the second harness port define fluid passageways into the second channel.

10. The optical cannula system of claim 8, wherein the internal wall of the harness block comprises a plurality of internal apertures configured to allow fluid communication between the second channel and the central channel.

11. The optical cannula system of claim 10, wherein a position of the valve shaft within the second channel defines which internal apertures of the plurality of internal apertures the first harness port and the second harness port are in fluid communication with.

12. The optical cannula system of claim 10, wherein in the first configuration, the first harness port is in fluid communication with a first aperture of the plurality of internal apertures and the second harness port is in fluid communication with a third aperture of the plurality of internal apertures, wherein in the second configuration, the first harness port is in fluid communication with the third aperture of the plurality of internal apertures and the second harness port is in fluid communication with a second aperture of the plurality of internal apertures.

13. An optical cannula system, comprising:
a cannula, comprising:
an outer cannula wall having a proximal portion and a distal end;
a first channel within the outer cannula wall, the first channel configured for suction in a first configuration of the optical cannula system and configured for irrigation in a second configuration of the optical cannula system;
a second channel within the outer cannula wall, the second channel configured for irrigation in the first configuration and suction in the second configuration;
one or more internal walls within the outer cannula wall, the one or more internal walls extending at least partially along a length of the outer cannula wall between the proximal portion and the distal end, the one or more internal walls at least partially defining the first channel and the second channel;
a first cannula port disposed through the outer cannula wall into the first channel;
a second cannula port disposed through the outer cannula wall into the first channel; and
a third cannula port disposed through the outer cannula wall into the second channel;
a harness assembly comprising a first harness port and a second harness port, wherein in the first configuration, the first harness port is in fluid communication with the first cannula port and the second harness port is in fluid communication with the third cannula port, wherein in the second configuration, the first harness port is in fluid communication with the third cannula port and the second harness port is in fluid communication with the second cannula port; and
a body configured to receive the proximal portion of the cannula, wherein the harness assembly is disposed at least partially within the body.

14. The optical cannula system of claim 13, further comprising:
a first tube extending from the body;
a second tube extending from the body; and
a valve assembly connected to the body, the valve assembly configured to transition the optical cannula system between the first configuration and the second configuration.

15. The optical cannula system of claim 13, wherein the first channel comprises a main channel portion and a side channel portion extending from the main channel portion, the one or more internal walls at least partially defining the main channel portion and the side channel portion, the main channel portion configured to receive a shaft of a tool, the side channel portion configured to allow fluid communication around the main channel portion and the shaft of the tool.

16. The optical cannula system of claim 15 wherein a first total cross-sectional area of the side channel portion is larger than a second total cross-sectional area of the second channel.

17. The optical cannula system of claim 15, wherein the cannula further comprises a second channel port, the second channel port extending through the outer cannula wall near the distal end and into the second channel, the second channel port configured to allow fluid communication between an environment external to the cannula and the second channel.

18. The optical cannula system of claim 17, wherein the second channel port is located on an opposite side of the cannula than the side channel portion.

19. The optical cannula system of claim 13, further comprising an optical cap housing a camera chip, the optical cap configured to be connected to the distal end of the cannula.

20. The optical cannula system of claim 19, wherein the optical cap further comprises a central opening configured to be at least partially aligned with the first channel, the central opening allowing fluid communication between the first channel and an external environment through the optical cap.

21. The optical cannula system of claim 19, wherein the optical cap further comprises one or more tapered portions, the one or more tapered portions at least partially defining a distally narrowing outer surface of the optical cap.

22. The optical cannula system of claim 19, wherein the optical cap further comprises a side port extending through a side wall thereof, the side port configured to allow fluid communication between the second channel and an external environment through the optical cap.

23. The optical cannula system of claim 22, wherein the side port extends through a recessed portion of the optical cap.

24. The optical cannula system of claim 22, wherein the optical cap further comprising a second side port extending through a side wall thereof, the second side port configured to allow fluid communication between the first channel and an external environment through the optical cap.

25. The optical cannula system of claim 24, wherein the side port and the second side port are located on substantially opposite sides of the optical cap.

26. The optical cannula system of claim 13, wherein the cannula further comprises a curved region between the distal end and the proximal portion such that a central axis of the distal end is at a non-zero angle relative to a central axis of the proximal portion.

27. The optical cannula system of claim 26, wherein the non-zero angle is between 15 degrees and 45 degrees.

28. An optical cannula system, comprising:
a handle comprising:
   a body;
   a first port extending at least partially through the body, the first port configured to connect to a first hose; and
   a second port extending at least partially through the body, the second port configured to connect to a second hose;
a cannula, comprising:
   an outer cannula wall having a proximal portion and a distal end, the proximal portion configured to be disposed within the body;
   a first channel within the outer cannula wall, the first channel configured to be in fluid communication with the first port in a first configuration and the second port in a second configuration;
   a second channel within the outer cannula wall, the second channel configured to be in fluid communication with the second port in the first configuration and the first port in the second configuration;
   a first cannula port disposed through the outer cannula wall into the first channel;
   a second cannula port disposed through the outer cannula wall into the first channel; and
   a third cannula port disposed through the outer cannula wall into the second channel; and
a harness assembly comprising a first harness port and a second harness port, the first harness port aligned with the first port, the second harness port aligned with the second port, wherein in the first configuration, the first harness port is in fluid communication with the first cannula port and the second harness port is in fluid communication with the third cannula port, wherein in the second configuration, the first harness port is in fluid communication with the third cannula port and the second harness port is in fluid communication with the second cannula port.

29. The optical cannula system of claim 28, further comprising a valve assembly connected to the body, the valve assembly configured to move the optical cannula system between the first configuration and the second configuration.

30. The optical cannula system of claim 29, wherein the valve assembly comprises:
   a handle moveable relative to the body, the handle configured to move the optical cannula system between the first configuration and the second configuration; and
   a valve shaft connected to the handle, in the first configuration, the valve shaft configured to allow fluid communication between the first hose and the first channel and between the second hose and the second channel, and in the second configuration, the valve shaft configured to allow fluid communication between the first hose and the second channel and between the second hose and the first channel.

* * * * *